US012062458B2

(12) United States Patent
Morris et al.

(10) Patent No.: US 12,062,458 B2
(45) Date of Patent: *Aug. 13, 2024

(54) SYSTEM AND METHOD FOR SECURE, PRIVATE, AND TRUSTED MEDICAL INFORMATION MONITORING AND SEMI-AUTONOMOUS PRESCRIPTION MANAGEMENT

(71) Applicant: Singapore Ministry of Heath Office for Healthcare Transformation, Singapore (SG)

(72) Inventors: Robert John Tasman Morris, Singapore (SG); Praveen Deorani, Singapore (SG); Nikola Vouk, Singapore (SG)

(73) Assignee: Singapore Ministry of Health Office of Healthcare Transformation, Singapore (SG)

( * ) Notice: Subject to any disclaimer, the term of this patent is extended or adjusted under 35 U.S.C. 154(b) by 726 days.

This patent is subject to a terminal disclaimer.

(21) Appl. No.: 16/905,784

(22) Filed: Jun. 18, 2020

(65) Prior Publication Data
US 2021/0118579 A1 Apr. 22, 2021

Related U.S. Application Data

(60) Provisional application No. 62/923,640, filed on Oct. 21, 2019.

(51) Int. Cl.
*G06F 21/62* (2013.01)
*G06F 21/32* (2013.01)
(Continued)

(52) U.S. Cl.
CPC ............. *G16H 80/00* (2018.01); *G06F 21/32* (2013.01); *G06F 21/575* (2013.01);
(Continued)

(58) Field of Classification Search
CPC ......... G16H 80/00; G16H 10/65; G16H 20/10
See application file for complete search history.

(56) References Cited

U.S. PATENT DOCUMENTS

| 2005/0201345 A1* | 9/2005 | Williamson | G16H 40/63 370/338 |
| 2010/0082367 A1* | 4/2010 | Hains | G16H 20/10 705/2 |

(Continued)

*Primary Examiner* — Reginald R Reyes

(57) ABSTRACT

A patient identity and information manager (PIIM) is configured for establishing direct trust relationships between itself and (i) a particular patient; (ii) a biomarker monitoring device corresponding to the patient; and (iii) a medical care provider associated with the patient. The PIIM establishes: a first direct trust relationship corresponding to the patient by way of communication between the PIIM and a patient identification/biometrics module and establishment of a validated currently active patient identity; a second direct trust relationship corresponding to the biomarker data monitoring device by way of communication between the PIIM and the biomarker data monitoring device under the currently active patient identity; and a third direct trust relationship corresponding to the care provider by way of validating the care provider and providing the validated care provide with a biomarker data encryption key corresponding to each of the currently active patient identity and the biomarker monitoring device.

20 Claims, 27 Drawing Sheets

(51) Int. Cl.
　　　*G06F 21/57*　　　(2013.01)
　　　*G06K 19/06*　　　(2006.01)
　　　*G16H 10/65*　　　(2018.01)
　　　*G16H 20/10*　　　(2018.01)
　　　*G16H 80/00*　　　(2018.01)
　　　*H04L 9/32*　　　(2006.01)
　　　*H04L 9/40*　　　(2022.01)

(52) U.S. Cl.
　　　CPC ... *G06F 21/6245* (2013.01); *G06K 19/06037* (2013.01); *G16H 10/65* (2018.01); *G16H 20/10* (2018.01); *H04L 9/3247* (2013.01); *H04L 63/0838* (2013.01)

(56) References Cited

U.S. PATENT DOCUMENTS

| | | | | |
|---|---|---|---|---|
| 2014/0304505 | A1* | 10/2014 | Dawson | G06F 21/6227 713/165 |
| 2017/0124727 | A1* | 5/2017 | Amat Roldan | G01B 11/14 |
| 2018/0268726 | A1* | 9/2018 | Kaleal, III | G09B 19/00 |
| 2020/0319015 | A1* | 10/2020 | Kamiyama | G01G 19/50 |

\* cited by examiner

SYSTEM AND METHOD FOR SECURE, PRIVATE, AND TRUSTED MEDICAL INFORMATION MONITORING AND SEMI-AUTONOMOUS PRESCRIPTION MANAGEMENT

CROSS-REFERENCE TO RELATED APPLICATION

This application claims priority to U.S. Provisional Patent Application No. 62/923,640, filed 21 Oct. 2019, which is incorporated by reference herein in its entirety.

TECHNICAL FIELD

Aspects of the present disclosure relate to systems and methods for security-enhanced or secure, privacy-enhanced or private, and trust-enhanced or trusted medical data communication. Aspects of the present disclosure also relate to systems and methods for semi-autonomous medical treatment plan or prescription management.

BACKGROUND

Home monitoring of vital signs or biomarkers is known to be a valuable adjunct in the treating of chronic diseases such as diabetes, hypertension, hyperlipidemia, respiratory disease, congestive heart failure, etc., by allowing the disease to be monitored and managed at home by the patient. Patients increasingly have at their disposal a variety of devices to measure relevant vital signs or biomarkers, which can give them an awareness of their present condition as well as enable them to understand their personal response to various lifestyle choices such as food intake, activity, sleep, smoking, etc. . . . . Vital signs and clinical biomarkers include, but are not limited to, blood pressure, pulse rate, blood glucose, blood oxygen, forced expiratory volume (spirometry), weight, lipid levels, etc. Home monitoring systems and devices are also commonly used for monitoring of patients after discharge from hospital. These systems and devices may be acquired over-the-counter, provided by the patient's healthcare provider, or obtained from another party (e.g., third party) or source.

In the past, such vital sign or biomarker measurements have been stored locally in these devices, and the only way to share them with a healthcare provider has been for the patient to note them down manually and bring them to the healthcare provider who then can provide advice, further diagnosis, revision of medications, etc. Recently, systems and devices have emerged that transmit the readings directly to a clinic or clinician computing device, such as in a manner shown in FIG. 1, thus allowing more reliable recording of data as well as allowing the care provider to stay in touch with the patient telephonically, or via messaging, thereby providing as-needed advising or coaching on patient behavior. In many cases, the care provider follows a script that may involve reminders to take readings, or enquiries about why readings might be out of range. It has been shown in multiple studies that the time to get chronic diseases under control, and the amount of hospital readmission, can be improved with various forms of home monitoring. In recent years, these interactions have become automated by automatons commonly referred to as "bots," for example, Resmed, which monitor the patient's vital sign or biomarker readings, compute feedback that is delivered to the patient, and only communicate escalations on an as-needed basis to clinical staff.

Nevertheless, existing home monitoring systems and devices need to provide higher or improved levels of security and privacy so that (a) patients can be assured of secure, private transmission and storage of data; and (b) the healthcare provider can trust the integrity and authenticity of the home monitoring systems or devices, and that the readings obtained thereby are coming from the intended or correct patient.

Commercial cloud services are also becoming increasingly used as they have the advantage of offloading both the smaller and larger clinical provider from the burden of information technology (IT) management. The one downside of cloud services, and one that is limiting their adoption, is the concern or fear that with the outsourcing of IT management, a risk to the security and privacy of sensitive patient data will accrue. This concern has been particularly amplified by numerous recent data breaches, particularly in the healthcare industry. Breach of patient privacy can have devastating effects on individuals in terms of insurability as well as personal privacy, stigma etc., as well as providing fertile soil for fraudulent healthcare claims.

Healthcare systems may impose strict limitations as to what patient data is allowed to be transmitted, and how it may be stored on shared facilities or computing resources such as public clouds (e.g., available from Amazon Web Services, Microsoft Azure, etc. . . . ). It is sometimes mandated that even "anonymized" data (e.g., personal health data for which identifiers such as Patient IDs, Medical Record Numbers, etc. . . . have been removed or pseudonymized) has to be handled in a special manner, since it is known that patients' data can sometimes be re-identified from particular patterns it contains.

A further risk emerges in home monitoring of patient data. The actual pattern of the taking of certain health-related measurements could unintentionally disclose the patterns of movement or travel of the patient, for example their daily routine could be ascertained, or it could be deduced that they are away from home or in a different time zone (which could entail personal safety risks or potential for privacy invasion). Readings of a particular kind or at a certain time of day could allow inference that the patient is suffering from a specific form of chronic disease. Repeated readings could allow inference that an abnormal reading, or one of concern, has been obtained.

In view of the foregoing, a need exists for ensuring individuals using health monitoring technology maintain the integrity of data, ensure integrity of home monitoring technology, ensure that the individual's personal data privacy is appropriately safeguarded or maintained, and that the data received by the healthcare provider may be trusted to provide home monitoring of healthcare vital signs and use their results to improve health outcomes.

SUMMARY

In accordance with an aspect of the present disclosure, an automated data processing process or method for secure, private, and trusted monitoring, management, and communication of medical information corresponding to a patient includes: (a) providing a data communication network; (b) providing a set of provider-side data processing resources corresponding to a medical care provider associated with the patient, the set of provider-side data processing resources coupled to the data communication network, the set of provider-side data processing resources including a provider-side computing system; (c) providing a set of patient-side data processing resources, the set of patient-side data processing resources coupled to the data communication network, the set of patient-side data processing resources including: (i) a patient identification/biometrics module configured for generating patient identification/biometrics data corresponding to the patient in response to patient input; (ii) a biomarker monitoring device associated with the patient, the biomarker monitoring device configured to monitor a set of patient biomarkers and store corresponding patient biomarker data in a biomarker data store; and (iii) a Personal Identity and Information Manager (PIIM) corresponding to the patient, the PIIM including data processing resources configured for establishing direct trust relationships between the PIIM and each of the patient, the biomarker monitoring device, and the care provider; (d) establishing a first direct trust relationship between the PIIM and the patient by way of: communication between the PIIM and the patient identification/biometrics module following patient input directed to the patient identification/biometrics module, performing patient validation operations, and establishment of a currently active patient identity; (e) establishing a second direct trust relationship between the PIIM and the biomarker data monitoring device by way of communication between the PIIM and the biomarker data monitoring device under the currently active patient identity, and validation of the biomarker data monitoring device; and (f) establishing a third direct trust relationship between the PIIM and the care provider by way of communication between the care provider computing system and the PIIM, PIIM validation of the care provider, and provision of a biomarker data decryption key corresponding to the currently active patient identity and the biomarker monitoring device to the care provider computing system or a set of network-based data processing resources couplable or coupled to the set of provider-side computing resources by way of the data communication network, wherein the biomarker data decryption key enables decryption of encrypted biomarker data corresponding to the currently active patient identity and the biomarker monitoring device.

In such a process or method, establishing the first direct trust relationship can include: generating patient identification data by way of the patient identification/biometrics module in response to patient interaction therewith; provision of the patient identification data to the PIIM; PIIM performance of the patient validation operations using the patient identification data, during which the PIIM attempts to validate the patient identification data; PIIM generation and storage of a new unique patient identity corresponding to the patient in response to unsuccessful validation of the patient identification data; and PIIM retrieval of a previously generated and stored unique patient identity as the currently active patient identity in response to successful validation of the patient identification data.

Establishing the second direct trust relationship can include: establishing communication between the PIIM and the biomarker monitoring device under the currently active patient identity; PIIM performance of biomarker monitoring device validation operations in which the PIIM attempts to validate a hardware identity and/or a software identity of the biomarker monitoring device; and following successful PIIM validation of the hardware identity and/or the software identify of the biomarker monitoring device: PIIM generation and storage, or PIIM retrieval, of a unique code corresponding to the biomarker monitoring device; and PIIM generation of an ephemeral biomarker data encryption key by which patient biomarker data can be encrypted during a biomarker monitoring session corresponding to the currently active patient identity. As part of the biomarker monitoring device validation operations, the PIIM can attempt to validate secure boot protocol data generated by the biomarker monitoring device.

Establishing the third direct trust relationship can include: PIIM generation of a biomarker data decryption code corresponding to the active patient identity and the biomarker monitoring device; PIIM association of the biomarker data decryption code with a unique one-time use code; communication of the unique one-time use code to the set of provider-side data processing resources; attempted validation of the one-time use code by way of communication between the set of provider-side data processing resources and the PIIM; and in response to successful validation of the one-time use code, generating the biomarker data decryption key corresponding to the currently active patient identity and the biomarker monitoring device.

The set of patient-side data processing resources can further include a patient computing device corresponding to the patient, and communication of the one-time code to the set of provider-side data processing resources can include: communicating the one-time use code from the PIIM to the patient computing device; and subsequently communicating the one-time use code from the patient computing device to the set of provider-side data processing resources. The one-time use code can be encoded in a matrix barcode or a Quick Response (QR) code.

Attempted validation of the one-time use code can include: communication of an assertion signed by the care provider's digital signature to the PIIM; and PIIM determination of whether the assertion was digitally signed by a trusted authority or an approved delegate of the trusted authority.

The PIIM can include one of: (a) integrated circuitry provided as part of the biomarker monitoring device; (b) integrated circuitry carried by a smart card or a patient identification card belonging to the patient; (c) integrated circuitry associated with a customized Subscriber Identity Module (SIM) card, wherein customized SIM card is carried by a smartphone corresponding to the patient and which forms a portion of the patient-side data processing resources; and (d) a set of program instructions stored in a memory of and executable by a processing unit of a patient computing device corresponding to the patient and which forms a portion of the patient-side data processing resources.

The provider computing system can be configured for executing a patient management application by which a current prescription including a current prescription protocol corresponding to the patient is definable by the care provider, wherein the current prescription protocol specifies a biomarker that the patient is to monitor by way of the biomarker monitoring device and a corresponding biomarker monitoring schedule; the set of patient-side data processing resources can further include a patient computing device executing an automated prescription management agent; and the process or method can further include: communicating the current prescription protocol to the PIIM; and, by way of execution of the prescription management agent, at least one of automatically: presenting instructions, coaching, guidance, reminders, or recommendations relating to the current prescription protocol to the patient; performing biomarker data analysis upon biomarker data generated by the biomarker monitoring device in relation to the current prescription protocol; performing prescription compliance analysis indicating patient compliance with the current prescription protocol; adaptively providing the patient with feedback based on patient input, the biomarker data analysis, and/or the prescription compliance analysis; and adaptively adjusting the current prescription protocol based on patient input, the biomarker data analysis, and/or the prescription compliance analysis.

The prescription management agent can be communicated from the set of provider-side data processing resources to the patient computing device by way of the data communication network.

The prescription management agent can include a state machine executable by a processing unit of the patient computing device.

The PIIM can include a prescription checkbot, and the process or method can further include prescription checkbot analysis of prescription management agent state transitions corresponding to execution of the current prescription protocol, and prescription checkbot determination of whether aspects of the current prescription protocol fall outside of or too closely approach recognized or established guidelines or contraindications for patient safety.

The process or method can further include prescription checkbot limiting, restricting, or preventing (a) the presentation of particular instructions, recommendations, or information to the patient, and/or (b) the prescription management agent's adaptive adjustment of particular prescription protocol parameters based on the prescription checkbot's analysis of one or more current prescription protocol state transitions corresponding to execution of the current prescription protocol.

A patient computing device can include or be a smartphone having a memory in which the prescription management agent resides, and a processing unit configured for executing the prescription management agent.

In accordance with a further aspect of the present disclosure, such a process or method can further include: acquiring patient biomarker data by way of the biomarker monitoring device; encrypting, storing, and processing the patient biomarker data; selectively communicating at random times each of dummy data and actual patient data including at least one of patient biomarker data, summary data corresponding to patient biomarker data, and an emergency alert to a destination external to the set of patient-side data processing resources and which includes one of the set of provider-side data processing resources and a set of network based data processing resources couplable or coupled to the set of provider-side data processing resources, wherein the communication of the dummy data to the external destination occurs at least 50% more frequently than the communication of actual patient data to the external destination. In various embodiments, communication of actual patient data corresponding to normal, non-emergency medical situations to the external destination is avoided.

In accordance with another aspect of the present disclosure, a process or method for privately communicating medical data corresponding to a patient includes: providing a set of patient-side data processing resources corresponding to the patient, the set of patient-side data processing resources including a set of biomarker monitoring devices; acquiring patient biomarker data corresponding to the patient by way of the set of biomarker monitoring devices; encrypting, storing, and processing the patient biomarker data within the set of patient-side data processing resources; and selectively communicating each of dummy data and actual patient data including at least one of patient biomarker data, summary data corresponding to patient biomarker data, and an emergency alert to a destination external to the set of patient-side data processing resources by way of a computer network, wherein the communication of the dummy data to the destination external to the set of patient-side data processing resources occurs at least 50% more frequently than the communication of actual patient data to the destination external to the set of patient-side data processing resources.

Such a process or method can further include avoiding communication of actual patient data corresponding to normal, non-emergency medical situations to the destination external to the set of patient-side data processing resources.

DETAILED DESCRIPTION

Figure 1:
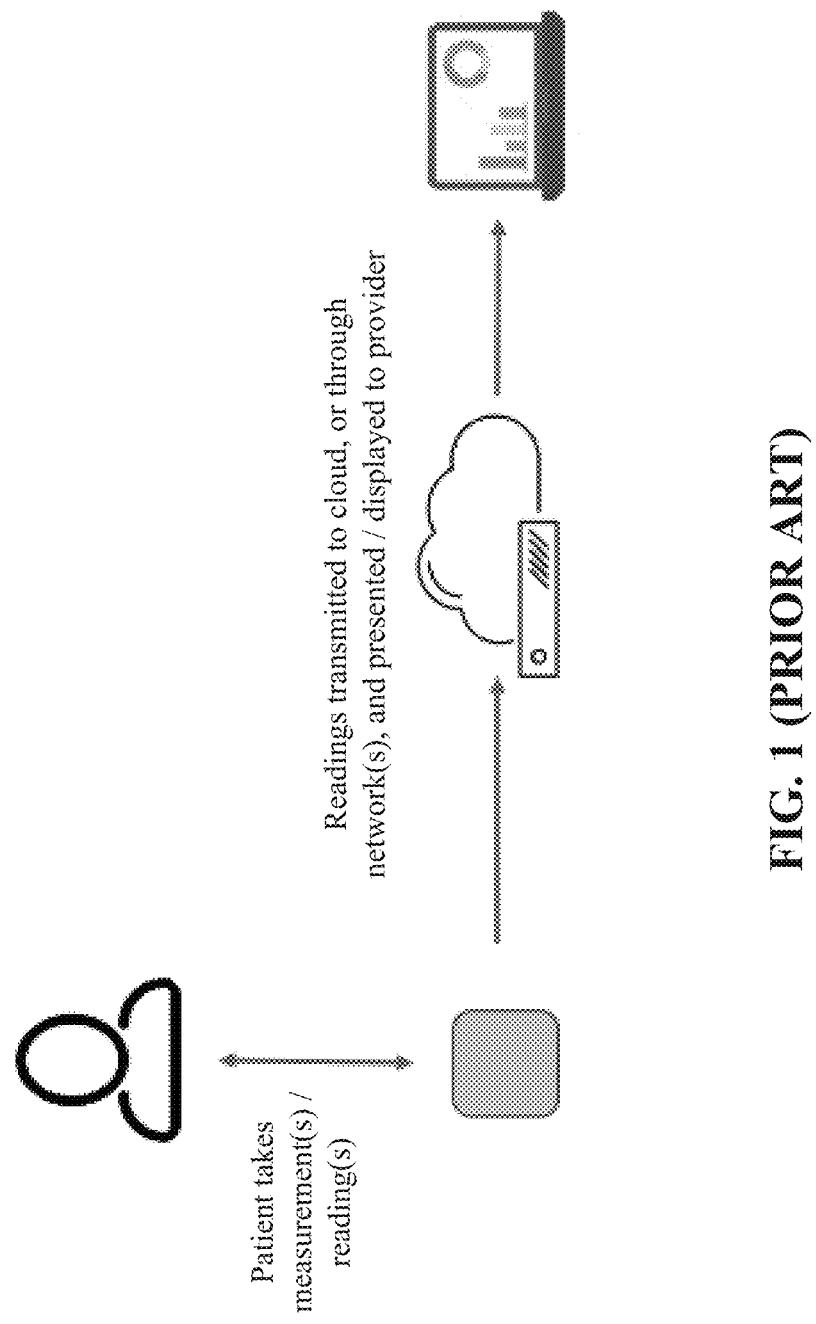
FIG. 1 illustrates aspects of a prior art system for medical information monitoring.

In this specification, unless the context stipulates or requires otherwise, any use of the word "comprise," and variations thereof such as "comprises" or "comprising," imply the inclusion of a stated element or operation or group of elements or operations, but not the exclusion of any other element or operation or group of elements or operations.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavor to which this specification relates.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in An Introduction to Mathematical Reasoning: Numbers, Sets, and Functions "Chapter 11: Properties of Finite Sets" (e.g., as indicated on p. 140), by Peter J. Eccles, Cambridge University Press (1998)). Thus, a set includes at least one element. In general, an element of a set can include or be one or more portions of a system, an apparatus, a device, a structure, an object, a process, a physical parameter, or a value depending upon the type of set under consideration.

Herein, reference to one or more embodiments, e.g., as various embodiments, many embodiments, several embodiments, multiple embodiments, some embodiments, certain embodiments, particular embodiments, specific embodiments, or a number of embodiments, need not or does not mean or imply all embodiments.

The FIGs. included herewith show aspects of non-limiting representative embodiments in accordance with the present disclosure, and particular elements shown in the FIGs. may be representative in nature, in that they are not shown to scale or precisely to scale relative to each other, and/or can be implemented in different or multiple manners. The depiction of a given element or consideration or use of a particular element number in a particular FIG. or a reference thereto in corresponding descriptive material can encompass the same, an equivalent, an analogous, categorically analogous, or similar element or element number identified in another FIG. or descriptive material associated therewith. The presence of "/" in a FIG. or text herein is understood to mean "and/or" unless otherwise indicated. The recitation of a particular numerical value or value range herein is understood to include or be a recitation of an approximate numerical value or value range, for instance, within +/−20%, +/−15%, +/−10%, +/−5%, +/−2.5°%, +/−2%, +/−1%, +/−0.5%, or +/−0%. The term "essentially all" can indicate a percentage greater than or equal to 90% fix instance, 92.5%, 95%, 97.5%, 99%, or 100%.

Herein, the term "hardware" can include integrated circuitry, and the term "software" can include one or more program instruction sets that can be stored on or in a computer-readable or electronically-readable medium, and which are executable by a processing unit (e.g., integrated circuitry configured as a set of microprocessors or microcontrollers). The term software can encompass or include firmware, in a manner readily understood by individuals having ordinary skill in the art. While particular elements may be embodied as or primarily as hardware or software, such elements can alternatively be embodied as or primarily as software or hardware, respectively, or a combination thereof, depending upon the type of element under consideration and/or embodiment details, in a manner readily understood by individuals having ordinary skill in the relevant art. The term "processing unit" can include integrated circuitry configured for performing automated data processing operations or implementing an automated data processor, such as a microprocessor or microcontroller that can execute stored program instructions to perform specific types of functions or operations, such as transforming input information or data into output information or data, in a manner readily understood by individuals having ordinary skill in the relevant art. The term "memory" can include one or more forms of random access memory (RAM) and/or read-only memory (ROM), in which data and/or program instructions can reside, in a manner readily understood by individuals having ordinary skill in the relevant art.

Overview

Embodiments in accordance with the present disclosure are directed to automated systems, sub-systems, apparatuses, devices, and processes for security-enhanced, privacy-enhanced, and/or trust-enhanced acquisition, analysis, communication, monitoring, and/or management of wellness-related, health-related, medically-related, medically-relevant, or medical information, signals, or data associated with one or more individuals, users, subjects, or patients and their wellness, health, or medical care providers, practitioners, or professionals. Embodiments in accordance with the present disclosure can additionally or alternatively be directed to automated systems, sub-systems, apparatuses, devices, and processes for wellness, health, and/or medical care/treatment plan or prescription management for one or more individuals, users, subject, or patients and their wellness, health, or medical care providers, practitioners, or providers, including semi-autonomous, essentially autonomous, generally autonomous, or autonomous care/treatment plan or prescription distribution; care/treatment plan or prescription related information or data analysis and provision of feedback or guidance based thereon; and/or care/treatment plan or prescription compliance support, monitoring, or management.

Wellness-related, health-related, medically-related, medically-relevant, or medical information, signals, or data (e.g., data in digital form) can correspond to, include, or be based on, represented by, or derived or derivable from particular physiological or physiological correlate parameters, bio-data, bio-signals, biomarkers, and/or vital signs of one or more individuals, users, subjects, or patients. Non-limiting representative examples of physiological or physiological correlate parameters, bio-data, bio-signals, biomarkers, or vital signs correspond to or include measures or estimates of one or more of weight, height, body fat percentage, body temperature, blood pressure, blood glucose level, blood lipid level, peripheral capillary oxygen saturation (SpO2) level, forced expiratory volume (e.g., obtained by way of spirometer measurements), electroencephalography (EEG) state, electrocardiography (ECG) state, and/or other bodily parameters, in a manner readily understood by individuals having ordinary skill in the relevant art. Physiological or physiological correlate parameters, bio-data, bio-signal s, bio-markers, or vital signs can also include or be based upon or derived from the results of mathematical or statistical operations performed upon sequences or series of such acquired signals or data, as also understood by individuals having ordinary skill in the relevant art.

Embodiments in accordance with the present disclosure can operate in association with, involve, include, or be directed to essentially any type of apparatus, device, or piece of equipment that is configured for monitoring, measuring, or sensing such physiological or physiological correlate parameters, bio-data, bio-signals, biomarkers, and/or vital signs of one or more individuals, users, subjects, or patients, and which is or can be configured for supporting or operating in accordance with information or data security, privacy, and/or trust computational protocols and processes such as set forth herein, and/or which is or can be configured for supporting or operating in accordance with treatment plan or prescription management computational protocols and processes such as set forth herein. Such apparatuses, devices, and pieces of equipment can be present in or across one or more user home environments, community centers, workplace environments, care provider offices or facilities, acute care clinics, emergency medical response vehicles, hospitals, assisted living facilities, hospices, and/or other environments (e.g., community or private exercise facilities), in a manner that will be readily understood by individuals having ordinary skill in the relevant art.

For purpose of simplicity and brevity, physiological or physiological correlate parameters, bio-data, bio-signals, biomarkers, or vital signs may be referred to herein as biomarkers, which are represented, exist, or stored as biomarker data; an apparatus, device, or piece of equipment configured or configurable for acquiring, measuring, or monitoring biomarkers or generating and storing biomarker data may be referred to herein as a biomarker monitoring device; an individual, user, subject, or patient for whom a biomarker monitoring device has acquired, is acquiring, or is configured to acquire biomarker data may be referred to as a patient; a wellness, health, or medical care provider, practitioner, or professional (e.g., a physician) as well as a designated representative thereof (e.g., a nurse) associated with the patient (who in some situations may further act on behalf of the patient in undertaking certain activities) may each be referred to as a care provider or provider and a team of such individuals may be referred to as a care team; and a care/treatment plan or prescription provided to a patient by way of a care provider may be referred to as a prescription.

A prescription can be generated or defined by an appropriately approved or authorized care provider assigned to or associated with the patient for purpose of guiding, instructing, assisting, or aiding the patient in managing one or more types of wellness, health, or medical situations or conditions that the patient is experiencing or has recently or recurrently experienced, e.g., on an acute or chronic basis, in a manner readily understood by individuals having ordinary skill in the relevant art. More particularly, in the context of the present disclosure, a current prescription corresponding to a patient includes a current set of instructions and/or recommendations directed to the patient, which can be referred to or defined as a current prescription protocol. The prescription protocol can identify, indicate, or specify one or more types of activities, behaviors, therapies, and/or medications for the patient, plus a corresponding schedule therefor; and/or one or more biomarkers that the patient has been directed or needs to monitor (e.g., by way of a particular type of biomarker monitoring device), plus a corresponding schedule therefor.

Furthermore, in various embodiments a current prescription is associated with or implemented by way of an automated or semi-autonomous prescription management agent (e.g., a prescription management state machine) corresponding or transferrable to a patient system, apparatus, or device (e.g., a patient mobile computing device such as a smartphone or mobile phone, or a biomarker monitoring device in the patient's home). The prescription management agent can be configured for presenting instructions, coaching, guidance, reminders, or recommendations relating to the current prescription protocol to the patient; performing biomarker data analysis and prescription compliance support processes, including confirming or requesting patient confirmation of compliance with their current prescription protocol; possibly adaptively providing the patient with feedback and/or guidance based on patient input and/or biomarker data and/or prescription compliance analysis (e.g., to aid or encourage the patient in successfully complying with their current prescription); and possibly adaptively adjusting particular aspects of the current prescription protocol. In various embodiments, the prescription management agent is communicated from a care provider system, apparatus, or device (e.g., a provider computing device such as a smartphone/mobile phone or a tablet, laptop, or desktop computer) to the patient system, apparatus, or device for execution thereby, and the prescription management agent performs biomarker data analysis and prescription compliance support processes, without unnecessary or undesirable medical information or data communication back to the care provider system, apparatus, or device in the absence of an appropriate trigger condition or event such as the detection of a possible medical emergency situation, as further detailed below.

In various embodiments, the prescription management agent operates according to a state machine, such that the prescription management agent can identify, determine, or know a current prescription-related state of the patient, and can transition to another prescription-related state of the patient based on logic derived from one or more of timing; biomarker data received from a set of biomarker monitoring devices in use by the patient; additional data generated by or received from a set of additional devices that are in use by the patient (where such additional data can be automatically transmitted by the additional device(s), or manually entered by the patient); and/or further information or data directly entered by the patient. These prescription-related state transitions may be accompanied by outputs which can be communicated conveyed to the patient, a server, and/or the patient's care provider or care team. Such outputs can include prescription actions directed to the patient, which can encompass the communication or presentation of information or educational material to the patient; instructions to participate in one or more activities, behaviors, or therapies, and/or take measurements or medications; encouragement to conduct exercise or engage socially; or instructions to contact their care provider or team. Hence, prescription management encompasses and facilitates an entire care plan for the patient.

In the context of the present disclosure, information or data security relates to or encompasses a likelihood that at any given time or time interval, information or data that is communicated from an information or data origin or source, and which is intended for delivery to a particular information or data destination, contains actual medical information or data corresponding to a patient. As such, data security relates to or encompasses a likelihood that a data leak or breach, (e.g., due to a data interception or data theft event) contains (or excludes) a patient's actual medical information or data. Various embodiments in accordance with the present disclosure are configured for enhanced security or highly secure medical information or data communication, and thus for purpose of simplicity and brevity, such embodiments may be referred to herein as providing secure medical information or data communication.

Information or data privacy in the context of the present disclosure relates to or encompasses patient medical information or data confidentiality and access control, and particularly whether actual medical information or data corresponding to a patient is managed and kept confidential, (e.g., acquired, communicated, stored, accessed, used, viewed, retained, and deleted only by appropriately authorized parties) in accordance with one or more governmental data privacy acts or regulations. Various embodiments in accordance with the present disclosure are configured for confidentially managing medical information or data in accordance with one or more governmental data privacy acts or regulations, and thus for purpose of simplicity and brevity, such embodiments may be referred to herein as providing private medical information management.

Information or data trust in the context of the present disclosure relates to data integrity, for example, ensuring that improper changes to or corruption of data which could be related to the inputs or outputs of the prescription management agent are prevented or disallowed. Improper changes to data values are not allowed, whether the data values correspond to biomarker monitoring device readings, other data that could be related to biomarker measurements, inputs received from the patient, alarm messages, instructions form the patient's care provider or team, medication dosage levels, etc.

Embodiments in accordance with the present disclosure can assure data security, data privacy, and data integrity by way of one or more techniques. More particularly, embodiments in accordance with the present disclosure provide independent checking of data attributes by way of automated checkbots, which operate or execute in the scope or context of a trusted computing base, e.g., as part of a Personal Identity and Information Manager (PIIM or PI$^2$M) corresponding to the patient as further detailed below, and which perform independent and uncoupled assertion checking processes to assure data security, data privacy, and data integrity, thereby facilitating or assuring patient safety.

It can be noted that information or data trust in the context of the present disclosure additionally relates to or encompasses a likelihood that medical information or data associated with or corresponding to (a) a given patient; (b) a specific biomarker monitoring device, in view of the manufacturer and/or type of biomarker monitoring device and its capabilities and a current or most-recent operational status or configuration of the biomarker monitoring device; and (c) a particular care provider assigned to or associated with the patient actually or accurately reflects (i) the true identity of the patient; (ii) the true, intended, or expected identity, capabilities, and operational status or configuration of the specific biomarker monitoring device; and (iii) the true identity of this particular care provider, respectively, which collectively establish a high level of trust that the medical information or data exhibits integrity (e.g., is not fraudulent). Various embodiments in accordance with the present disclosure are configured for enhanced trust or highly trusted patient identity authentication or validation; biomarker monitoring device manufacturer/model, capability, and operational status or configuration validation; and care provider identity authentication or validation and associated care provider prescription validation, and for purpose of simplicity and brevity, such embodiments may be referred to herein as trusted.

Figure 2:
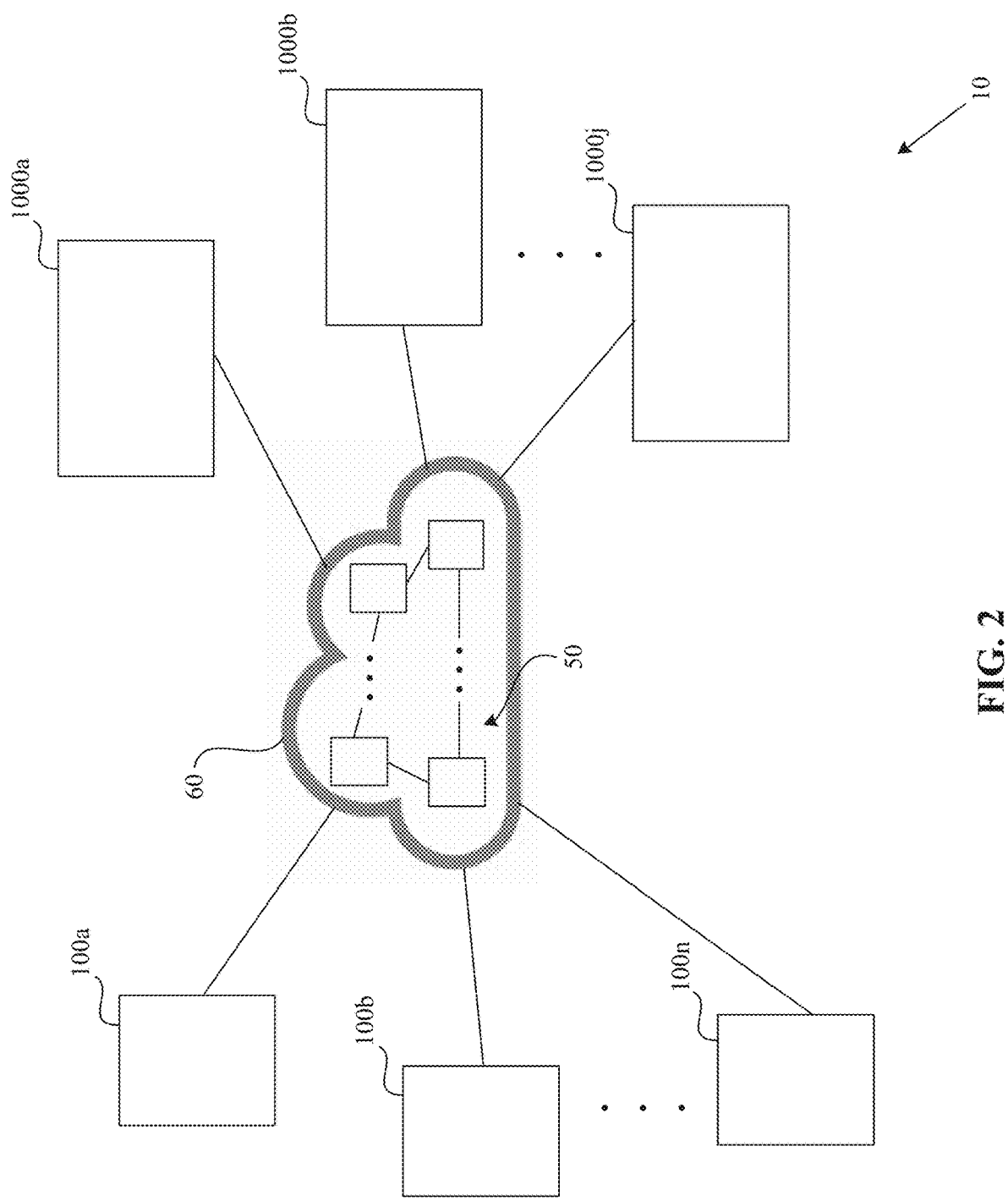
FIG. 2 is a schematic illustration showing aspects of a system for secure, private, trusted medical information monitoring and semi-autonomous, substantially-autonomous, or essentially-autonomous patient prescription management in accordance with an embodiment of the present disclosure.

Aspects of Representative Systems, Apparatuses, and Devices FIG. 2 is a schematic illustration showing aspects of a system 10 for secure, private, trusted medical information monitoring and semi-autonomous, substantially-autonomous, or essentially-autonomous patient prescription management in accordance with an embodiment of the present disclosure. In general, the system 10 includes multiple types of automated resources 50, 100, 1000 (e.g., hardware and/or software resources, systems, sub-systems, apparatuses, devices, units, or elements) including data processing, computation, or computing resources (e.g., processing units configured for executing stored program instructions, and/or finite automata) configured for secure, private, and trusted medical information management and semi-autonomous prescription management in accordance with particular embodiments of the present disclosure. More particularly, in various embodiments the system 10 includes at least one set of automated patient-facing, patient-based, or patient-side data processing/computing resources 100a-n corresponding to a set of patients, which for purpose of brevity can be referred to as patient-side resources 100a-n; at least one set of automated provider-facing, provider-based or provider-side data processing/computing resources 1000a-j corresponding to a set of care providers, which for purpose of brevity can be referred to as provider-side resources 1000a j; and at least one set of network-based data processing/computing resources 50, which in some embodiments at least partially resides in or across one or more private and/or public computing clouds 60, and which can be referred to hereafter as network-based resources 50. Patient-side resources 100a-n, provider-side resources 1000a-j, and network-based resources 50 are selectively coupled or couplable by way of one or more data communication networks, e.g., including the Internet and possibly one or more other types of networks such as wide area networks (WANs), local area networks (LANs), and cellular communication networks, in a manner readily understood by individuals having ordinary skill in the relevant art.

Patient-side resources 100 include, correspond to, or can be defined as hardware and/or software resources, including data processing, computation, or computing resources that are used by one or more patients as part of complying with their current prescription(s). In various embodiments, patient-side resources 100 include or are hardware and/or software that one or more patients can access and use without requiring their care provider(s) to be present, for instance, in a manner that is generally independent, essentially independent, or independent of the presence of their care provider(s). For instance, patient-side resources 100 can exist or be located or operate in a patient's home environment, a community center environment, and/or another type of environment (e.g., a pharmacy or shopping center).

A given set of patient-side resources 100 includes at least one biomarker monitoring device (e.g., which includes a biomarker acquisition interface by which biomarker data is acquirable from the patient, and a processing unit such as a microprocessor or microcontroller configured or configurable for executing memory-resident program instruction for sets acquiring, obtaining, or receiving, processing, and storing biomarker data corresponding to one or more types of biomarkers such as set forth above). However, it can be noted that in accordance with some embodiments, a biomarker monitoring device can be included as a standard portion, function, or feature of a consumer device such as a smartphone; for instance, a consumer device providing or configurable/configured for operating as a biomarker monitoring device can include an accelerometer/gyroscope unit that detects and records patient movement or activity (e.g., which can indicate the presence or absence of a movement-related patient state or condition, such as tremor), in a manner that individuals having ordinary skill in the relevant art will readily comprehend. Depending upon embodiment details, a biomarker monitoring device can include additional types of hardware and/or software resources or elements, such as user interface resources (e.g., a display screen), possibly data encryption resources (e.g., an encryption engine), and data communication resources (e.g., a network interface unit), as will be readily understood by individuals having ordinary skill in the relevant art. Depending upon embodiment and/or situational details, a given patient-side biomarker monitoring device can be provided to the patient by their care provider, or the patient can access or obtain the biomarker monitoring device by way of a third party source (e.g., the patient can purchase the biomarker monitoring device over-the-counter). As elaborated upon below, a given set of patient-side resources 100 additionally includes hardware and/or software resources configured or configurable for performing particular types of processes or operations in support of secure, private, and trusted medical information management and semi-autonomous prescription management.

Provider-side resources 1000 include, correspond to, or can be defined as hardware and/or software resources, including data processing, computation, or computing resources, which one or more care providers can utilize to generate and distribute prescriptions to their patients, analyze information or data corresponding to their patients, and/or selectively exchange information or data with their patients. A set of provider-side resources 1000 thus typically includes at least one provider computing device, such as set forth above. However, the possibility that essentially all or all provider-related computation is provided in the cloud is not precluded (e.g., is encompassed in at least some embodiments), and that the provider-side merely has devices that behave as dumb terminals. Provider-side computing devices can be located at a provider's office or facility, and/or in a data center or other server environment, in a manner readily understood by individuals having ordinary skill in the relevant art. A set of provider-side resources 1000 can also include one or more biomarker monitoring devices that are under the control (e.g., direct control) of a care provider (e.g., located at the care provider's office), which the care provider themselves can use to measure or monitor patient biomarker data during an in-person or direct interaction between the care provider and the patient (e.g., when the patient is at the care provider's facility or office), or which the care provider can permit the patient to use in association with a patient visit to the care provider. Patient access to and usage of such provider-side biomarker monitoring devices 1000 is typically not independent of their care provider's office/facility, presence, or direct control, in a manner readily understood by individuals having ordinary skill in the relevant art.

Information or data communication from a set of patient-side resources 100 to external or remote systems, subsystems, apparatuses, or devices, including provider-side resources 1000, can be directed or sent to or routed through the network-based resources 50; and similarly, information or data communication from a set of provider-side resources 1000 to external or remote systems, subsystems, apparatuses, or devices, including patient-side resources 100, can be directed or sent to or routed through the network-based resources 50. The network-based resources 50 can thus serve as an information or data intermediary, gatekeeper, and/or repository with respect to information or data transfer or exchange involving patient-side resources 100 and provider-side resources 1000. Thus, medical information or data acquired by a given biomarker monitoring device that resides at a particular physical location and which is to be communicated to a remote location can be directed or sent to or routed through the network-based resources 50. Network-based resources 50 can include a set of network-based computing systems, and a set of network-based information or data storage systems (e.g., for storing sets of program instructions executable by network-based or other computing systems, and storing information or data corresponding to or received from patient-side resources 100 and provider-side resources 1000).

Further Aspects of Patient-Side Resources

Figure 3A:
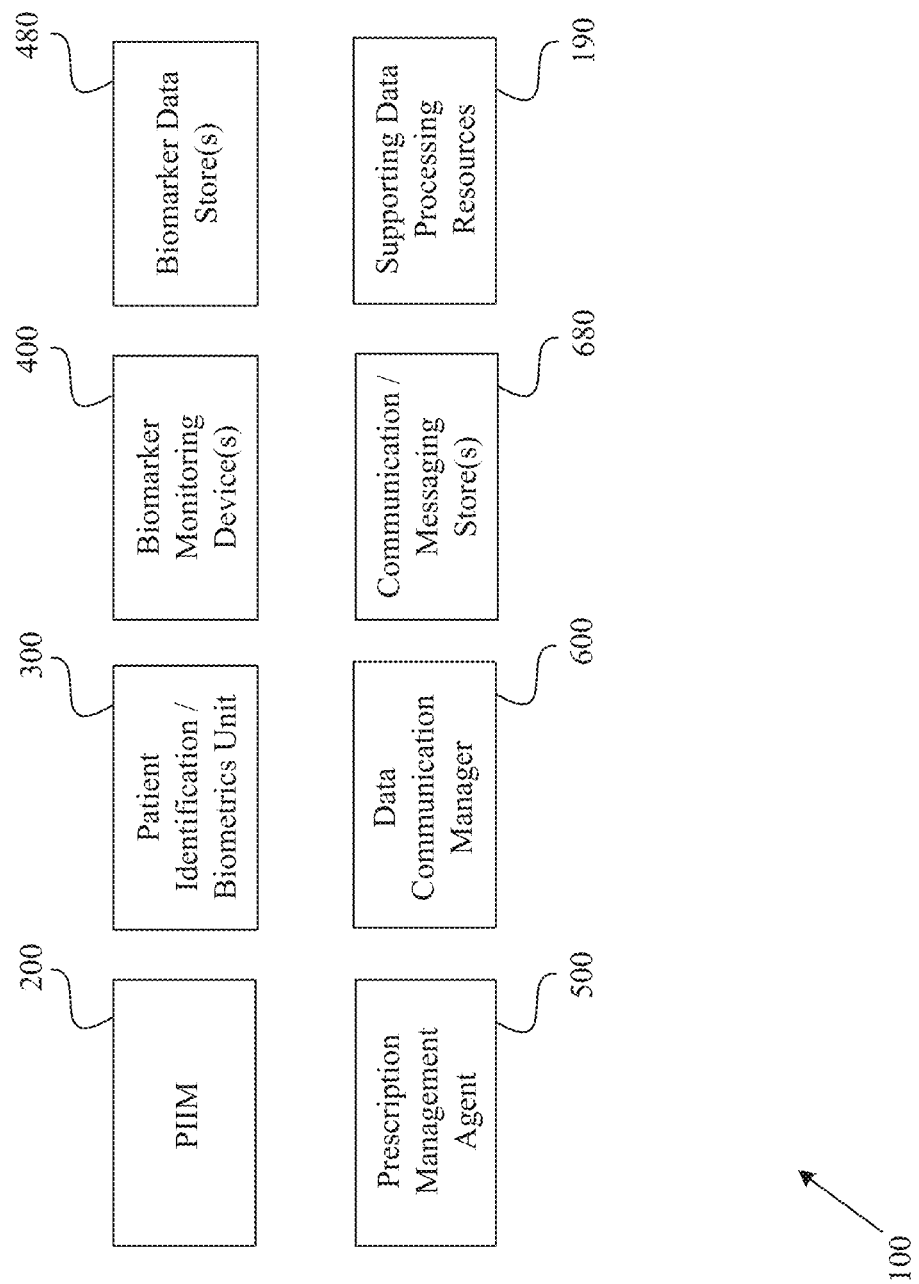
FIG. 3A is a block diagram showing aspects of a non-limiting representative configuration of patient-side resources in accordance with certain embodiments of the present disclosure.

FIG. 3A is a block diagram showing aspects of a non-limiting representative configuration of patient-side resources 100 in accordance with certain embodiments of the present disclosure. As indicated above, a given set of patient-side resources 100 includes or is implemented by way of one or more types of data processing, computation, or computing systems, apparatuses, or devices, including or such as one or more processing units (e.g., microprocessors or microcontrollers configured for executing memory-resident program instructions) coupled to computer-readable media (e.g., memories and/or data storage devices) and associated circuitry (e.g., integrated circuitry). As illustrated in FIG. 3A, in various embodiments a set of patient-side resources 100 corresponding to and usable/used by a specific patient includes a personal identity and information manager (PIIM or PI$^2$M) 200 corresponding to this patient, and with which this patient is registered and by which the patient's identity can be authenticated, authorized, and/or validated; a patient identification/biometrics unit 300 configured for receiving, capturing, or generating patient identification-related information or data such as a patient password or personal identification number (PIN) that the patient can enter, and/or patient biometric information or data to support or perform patient identity authentication processes or operations; at least one patient-side biomarker monitoring device 400 accessible to and usable by the patient (e.g., directly accessible to and usable by the patient, without their care provider's presence or direct control over the biomarker monitoring device 400), and which is also registered with the PIIM 200 and which can be validated thereby; at least one biomarker data memory or store 480, in which patient biomarker data can reside (e.g., in encrypted form); at least one patient-side prescription management agent 500 that is associated with a specific care provider, which can be validated by the PIIM 200, and which is configured for implementing or executing a current prescription or prescription protocol corresponding to the patient, and performing prescription compliance support operations such as tracking or analyzing the patient's biomarker data and/or other prescription-related data in view of a current prescription protocol established by this care provider, and guiding or assisting the patient in understanding and complying with their current prescription protocol; a patient-side data communication manager 600, which manages or controls how and when patient-related data, including patient biomarker data, is communicated external to the set of patient-side resources 100; at least one communication/messaging memory or store 680, in which externally directed/outgoing and externally received/incoming communications or messages relating to the set of patient-side resources 100 can be stored (e.g., on a selective or programmatically determined basis), including outgoing messages that may contain patient prescription-related data (e.g., patient biomarker data and/or prescription compliance data); and supporting, associated, auxiliary, or adjunctive patient-side data processing, computation, or computing resources 700 that are coupled or couplable to, used or usable by, associated with, or corresponding to each of the PIIM 200, the patient identification/biometrics unit 300, the patient-side biomarker monitoring device(s) 400, the patient-side prescription management agent 500, and the patient side biomarker data communication manager 600.

The patient identification/biometrics unit 300 can be coupled to or include one or more input devices such as a keypad or keyboard for receiving a password or PIN number corresponding to the patient (e.g., in response to patient input, or input by a patient-authorized delegate such as a caretaker or nurse); and/or a fingerprint identification unit, a facial recognition unit, a retinal scan unit, a voice print recognition unit, a handwriting recognition unit, and/or other type of hardware and/or software configured for capturing or generating patient biometric data, and possibly analyzing such biometric data as part of patient identity authentication processes or operations. Depending upon embodiment details, one or more portions of a patient identification/biometrics unit 300 can be coupled to or be carried by a biomarker monitoring device 400 and/or the supporting patient-side data processing or computing resources 700. A biomarker data store 480 can include or be a portion of the PIIM 200, a biomarker monitoring device 400, and/or the supporting patient-side data processing or computing resources 700. The supporting patient-side data processing or computing resources 700 can include hardware and/or software including one or more processing units (e.g., microprocessors and/or microcontrollers), memories for storing program instructions and data, data communication/network interface units, user input devices, output devices such as display devices, etc. . . . in a manner readily understood by individuals having ordinary skill in the relevant art. In a number of embodiments, the supporting patient-side data processing, computation, or computing resources 700 include a patient computing device such as a mobile phone or tablet computer configured to execute one or more patient-side apps (e.g., a patient care app) that support or perform secure, private, and trusted medical information management and semi-autonomous prescription management processes.

Figure 3B:
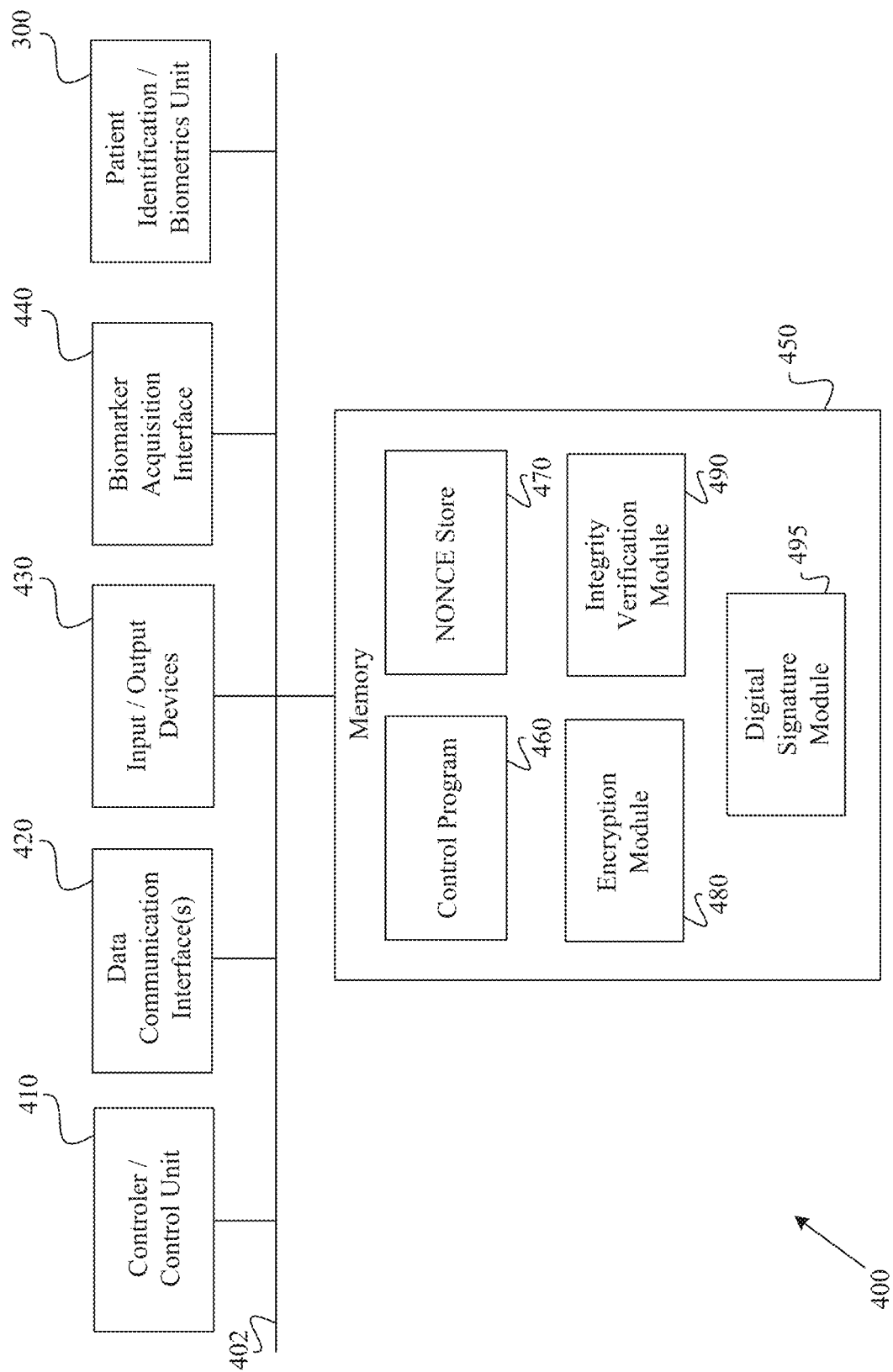
FIG. 3B is a block diagram showing aspects of a non-limiting representative biomarker monitoring device in accordance with an embodiment of the present disclosure.

FIG. 3B is a block diagram showing aspects of a non-limiting representative biomarker monitoring device 400 in accordance with an embodiment of the present disclosure. In an embodiment, the biomarker monitoring device 400 includes a controller or control unit (e.g., at least one microcontroller or microprocessor) 410, which can be configured for executing stored program instructions; at least one data communication interface 420, which can include a network communication interface by which the biomarker monitoring device 400 can establish data communication with one or more types of computer networks such as the Internet, and possibly a cellular data network; a set of input/output devices 430, which can provide one or more visual or graphical user interfaces to the patient; at least one biomarker acquisition interface 440, which is configurable or configured for acquiring or receiving biomarker signals and/or data from a portion of the patient's body (e.g., by way of direct or indirect coupling to a portion of the patient's body), and a memory 450 in which a biomarker monitoring device control program 460 resides. The memory 450 can further include one or more data stores that facilitate secure data communication, such as a cryptographic number-used-once (NONCE) store 470. The memory 450 can additionally include an encryption module 480, which enables the biomarker monitoring device 400 to perform cryptographic operations; plus an integrity verification module 490, and a digital signature module 495, which enable the biomarker monitoring device 400 to perform hardware/software integrity checking/validation operations, e.g., by way of a secure boot protocol operations (e.g., analogous to or associated with the secure boot standard), in a manner individuals having ordinary skill in the art will comprehend. As indicated above, the biomarker monitoring device 400 can include one or more portions of the patient identification/biometrics unit 300. Each of the foregoing elements can be configured for communication or coupled by way of a particular data transfer or communication pathways 402.

Depending upon biomarker monitoring device configuration, the capabilities of the biomarker monitoring device control program 460, and the type(s) of data communication interfaces 420 under consideration, the biomarker monitoring device 400 can be configured for communicating data to a patient computing device such a smart phone executing a patient care app; or a network destination or address, in which case the biomarker monitoring device 400 can be a direct-to-client and direct-to-cloud (D2C2) device configurable or configured for acting as a client with respect to receiving data from a network-based source or address, and sending data to a network-based destination or address, in a manner readily understood by individuals having ordinary skill in the relevant art.

Further Aspects of Provider-Side Resources

Figure 4A:
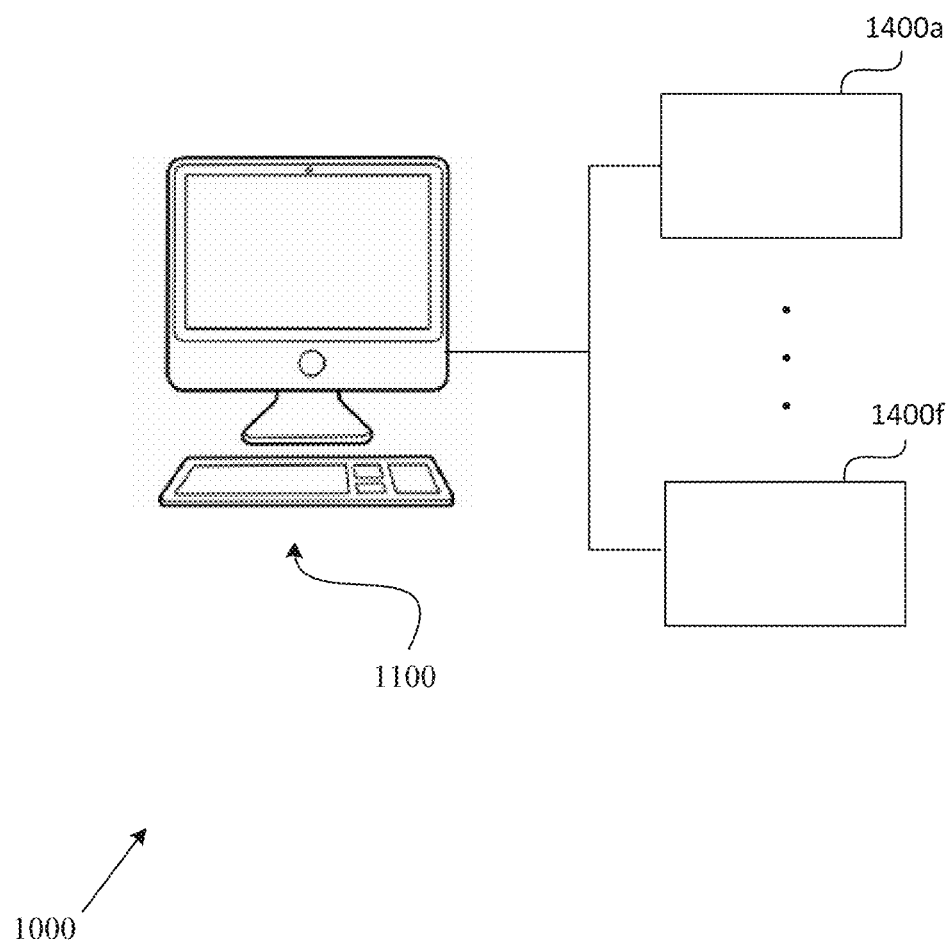
FIGS. 4A-4B show aspects of representative sets of provider-side resources in accordance with particular embodiments of the present disclosure.
Figure 4B:
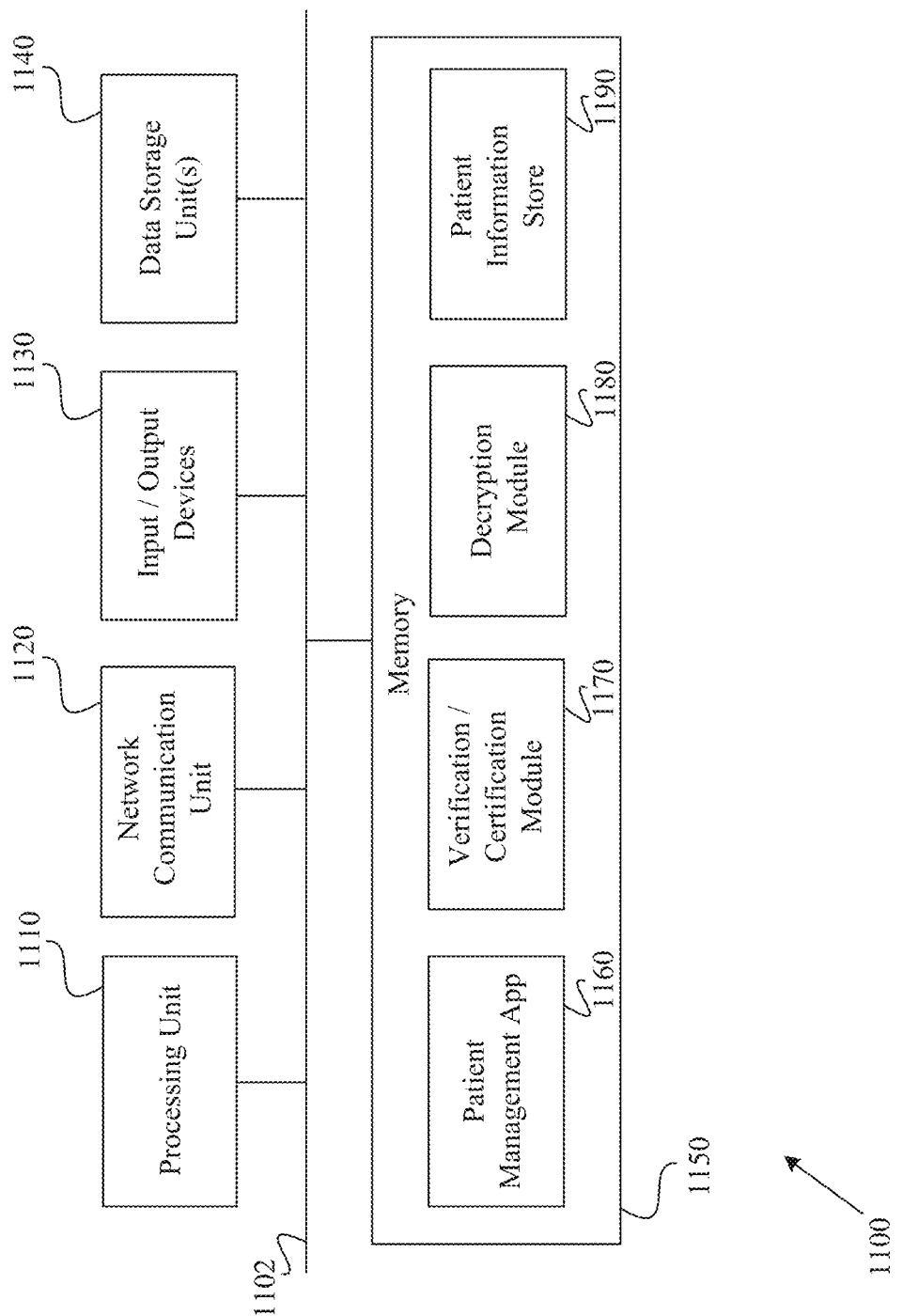

FIGS. 4A-4B are schematic illustrations showing aspects of a non-limiting representative configuration of provider-side resources 1000 in accordance with certain embodiments of the present disclosure. In an embodiments, a set of provider-side resources 1000 corresponding to a specific provider includes at least one care provider computing system or device 1100, such as a provider server, desktop, or laptop computer system and/or possibly a provider smartphone/mobile phone, which includes at least one processing unit 1110 (e.g., a microprocessor); at least one network communication unit 1120; a set of input/output devices 1130; and one or more computer-readable media including at least one data storage unit 1140 (e.g., a disk drive) and at least one memory 1150 (e.g., including random access memory (RAM) and read-only memory (ROM)) for storing data and program instructions executable by the processing unit 1110, in a manner readily understood by individuals having ordinary skill in the relevant art. The memory 1150 includes a patient management application program or app 1160; a verification/certification module 1170; a decryption module 1180; and a patient information or data store 1190. The memory 1150 also includes additional elements, such as an operating system, in a manner readily understood by individuals having ordinary skill in the relevant art. Each of the foregoing elements can be configured for communication or coupled by way of a particular data transfer or communication pathways 1102.

The verification/certification module 1170 includes program instruction sets which when executed facilitate or enable the identity of the provider under consideration to be verified or authenticated, and facilitate or enable the provider to verify, authenticate, and authorize data generated by a particular set of patient side resources 100. For instance, the verification/configuration module 1170 can be configured for performing digital signature operations, such as associating the provider's digital signature with messages, patient prescriptions, and data files, as individuals having ordinary skill in the relevant art will readily comprehend. The verification/certification module 1170 can also be configured for performing additional or other types of single factor or multi-factor authentication operations, in a manner also understood by individuals having ordinary skill in the relevant art.

The set of provider-side resources 1000 is configured for executing the patient management application program or app 1160. The patient management application or app 1160 typically includes each of a prescription management module by which the provider can generate/enter, distribute, and manage prescriptions corresponding to their patients; and a patient data management module by which the care provider can selectively access, review, and analyze data, including biomarker data, corresponding to their patients. The prescription management module includes program instruction sets which when executed can receive and process care provider input (e.g., directed to a visual or graphical user interface) that can establish or define a current prescription protocol for the patient, which can define or include a set of biomarker monitoring instructions (e.g., indicating a type of biomarker monitoring device 400 and a biomarker monitoring schedule) for a particular patient, and which can associate or link the current prescription protocol with a prescription management agent 500 for the patient. Taken together, the current prescription protocol and the prescription management agent 500 linked thereto can be defined as this patient's current prescription. The prescription management module can initiate or control the communication of the patient's current prescription to the patient, for instance, by way of a push process (e.g., in which the current prescription is pushed to the network-based resources 50, which further push the current prescription to a particular set of patient-side resources 100 corresponding to the patient under consideration).

In addition to the foregoing, a set of provider-side resources 1000 can include one or more provider-side biomarker monitoring devices 1400, in a manner indicated above, which can be configured for transferring or communicating biomarker data to the provider computing system or device 1100. Individuals having ordinary skill in the relevant art will recognize that multiple configurations of provider-side resources 1000 can exist in accordance with embodiments of the present disclosure, and provider-side resources 1000 are not limited to the representative configuration shown in FIG. 4A-4B.

Aspects of Trust Relationships

Figure 5:
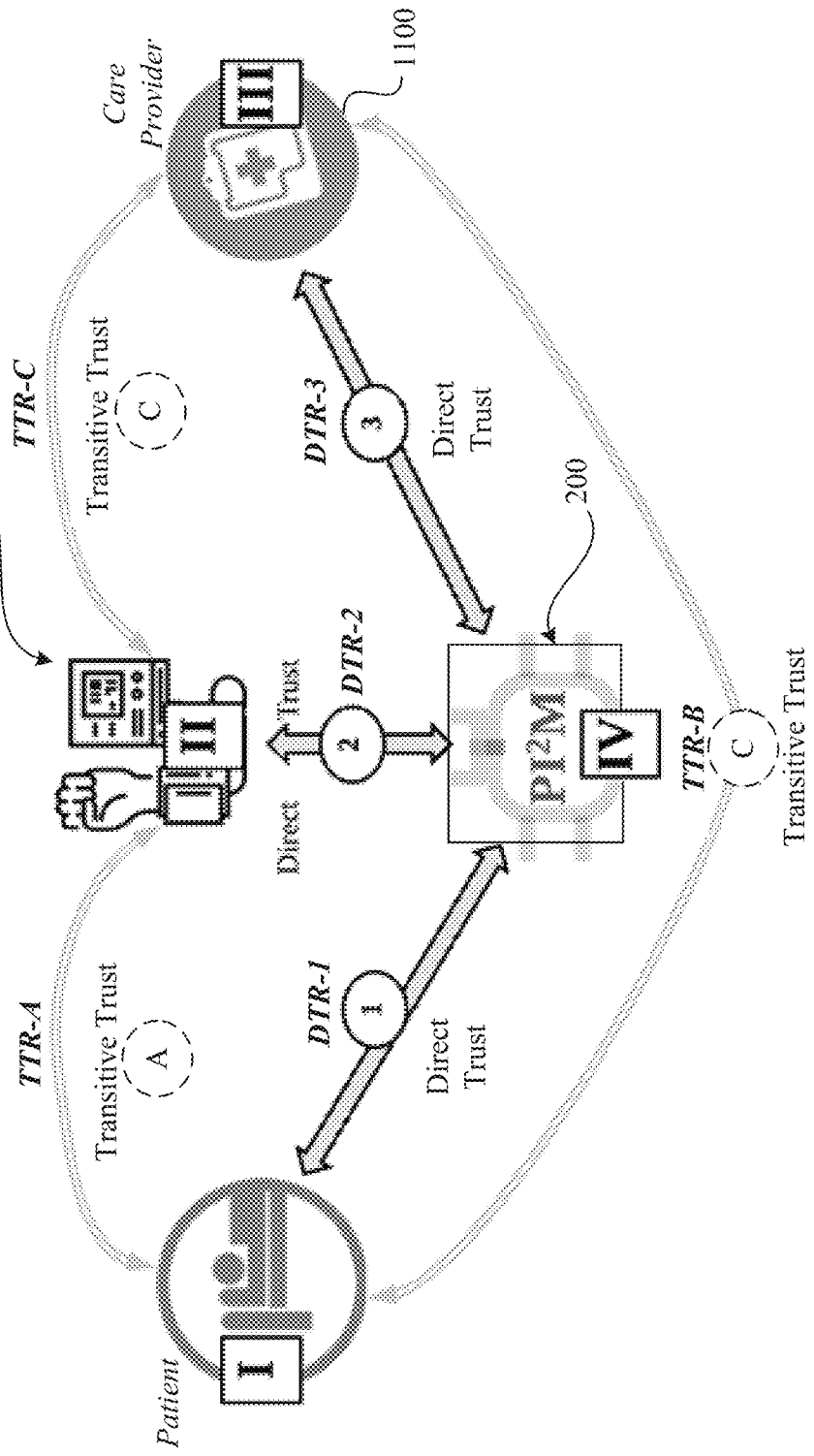
FIG. 5 illustrates a trust matrix in which direct and indirect trust relationships are established between four actors or parties, where such trust relationships are established by way of a Personal Identity and Information Manager (PIIM) in accordance with various embodiments of the present disclosure.

Referring again to FIG. 3A, the PIIM 200 corresponds to, serves as, or can be defined as a multi-actor or multi-entity trust gatekeeper with respect to a given patient, a particular patient-side biomarker monitoring device 400 or set of biomarker monitoring devices 400 usable by this patient, and a specific care provider that generates a current prescription for this patient. More particularly, in various embodiments the PIIM 200 is configured for performing direct trust processes or operations that establish direct or electronically/computationally verified trust relationships or assertions between itself and (1) the patient; (2) at least one biomarker monitoring device 400 usable or used by the patient (e.g., as part of biomarker data acquisition operations in accordance with the current prescription for this patient); and (3) the patient's care provider and a current prescription received therefrom. In addition to these direct trust relationships or assertions, the PIIM 200 enables the establishment of transitive trust relationships between (a) this patient and the biomarker monitoring device 400 under consideration; (b) this patient and the specific care provider under consideration; and (c) this care provider and the biomarker monitoring device 400 under consideration. This set of direct trust relationships or assertions and indirect trust relationships can be represented or defined as a four actor or four party trust matrix or model, which is illustrated in FIG. 5. The PIIM 200 can store and manage validated and/or authenticated identities and direct trust assertions, such as by way of proof-carrying authorization processes, thereby implementing the four actor trust model of FIG. 5. Herein, in accordance with FIG. 5, a direct trust relationship (DTR) between the PIIM 200 and the patient can be designated as DTR-1; a direct trust relationship between the PIIM 200 and a given biomarker monitoring device 400 can be designated as DTR-2; and a direct trust relationship between the PIIM 200 and the patient's care provider can be designated as DTR-3. Also in accordance with FIG. 5, a transitive trust relationship (TTR) between the patient and this biomarker monitoring device 400 can be designated as TTR-A; a transitive trust relationship between the patient and their care provider can be designated as TTR-B; and a transitive trust relationship between the care provider and this biomarker monitoring device 400 can be designated as TTR-C.

In a number of embodiments, the establishment of trust relationships or assertions, and hence the implementation of the four actor trust matrix or model shown in FIG. 5, can involve computational lambda calculus operations, in a manner individuals having ordinary skill in the art will comprehend.

In several embodiments, direct trust between the PIIM 200 and the patient is established by way of patient identity authentication or validation processes or operations, which can involve authenticating the patient's identity by way of patient input of a password or PIN, and/or the capture or generation of patient biometrics data by the patient identification/biometrics unit 300. Direct trust can also be established by the patient delegating to one or more entities (such as a nurse, hospital staff member, or other care provider) the right to authenticate (through assertions) on the patient's behalf using techniques or processes based on or corresponding to proof carrying authorization. Yet another technique can be a provider (e.g. such as a hospital staff member) asserting the identity of the patient prior to acting on the patient's behalf. The assertions are necessary to maintain the four actor trust model integrity and auditability of collected biometric information for traceability to the correct patient.

Direct trust between the PIIM 200 and a specific patient-side biomarker monitoring device 400 is established by way of PIIM 200 validation and registration of the biomarker monitoring device 400, which can be performed in association with or include the performance of biomarker monitoring device hardware and/or software validation operations to establish the hardware and/or software integrity of the biomarker monitoring device 400. The biomarker monitoring device hardware and/or software validation operations can be similar or analogous to or be based on or include secure boot protocol operations (e.g., associated with the secure boot security standard), in a manner readily understood by individuals having ordinary skill in the relevant art. Direct trust between the PIIM 200 and a specific patient care provider includes PIIM-mediated or PIIM-based validation of the care provider's identity; PIIM-mediated or PIIM-based granting of a patient data decryption key to provider-side resources 1000 associated with this provider (e.g., such that patient biomarker data can be decrypted and processed/analyzed/used by the provider-side resources 1000); and PIIM-based validation of the prescription(s) sent or distributed by this provider to the patient. In association with the foregoing, the PIIM can employ techniques, processes, or operations similar or analogous to or based on or including proof-carrying authorization, in a manner readily understood by an individual having ordinary skill in the relevant art.

The PIIM 200 can exist in the context of a given set of patient-side resources 100 in multiple manners or forms depending upon embodiment details. For instance, in an embodiment a PIIM 200 can be insertable into, carried by, or provided or integrated with a biomarker monitoring device 400. Alternatively, a PIIM 200 can be in the form of integrated circuitry carried by a physical card, such as a smart card or a patient identification/identity card (e.g., a national ID card) that can be communicatively coupled to one or more biomarker monitoring devices 400, and supporting data processing resources 700 can include hardware and/or software configured for securely communicating with the PIIM 200 in association with PIIM-based direct trust processes or operations. In another embodiment, a PIIM 200 can be implemented by way of program instructions (e.g., software) executable on a patient's mobile phone or other patient computing device for performing PIIM-based direct trust processes or operations, where the mobile phone or other patient computing device includes a tamper-evident or tamper-proof memory or data store for PIIM use (e.g., exclusive PIIM use). In still another embodiment, a PIIM 200 can correspond or be analogous to a customized or specialized Subscriber Identity Module (SIM) card that can be inserted into a patient's mobile phone, and which can perform direct trust processes or operations as set forth herein, where the mobile phone includes a tamper-evident or tamper-proof memory or data store for PIIM use (exclusive PIIM use). In a number of embodiments, the PIIM 200 is configurable or configured for performing one or more types of direct trust operations in accordance with an embedded tamper-evident or tamper-proof software and/or hardware module providing assurances of a hardware security module, in a manner that individuals having ordinary skill in the relevant art will readily comprehend.

Further Aspects of the PIIM and PIIM-Based Trust Processes or Operations

Figure 6:
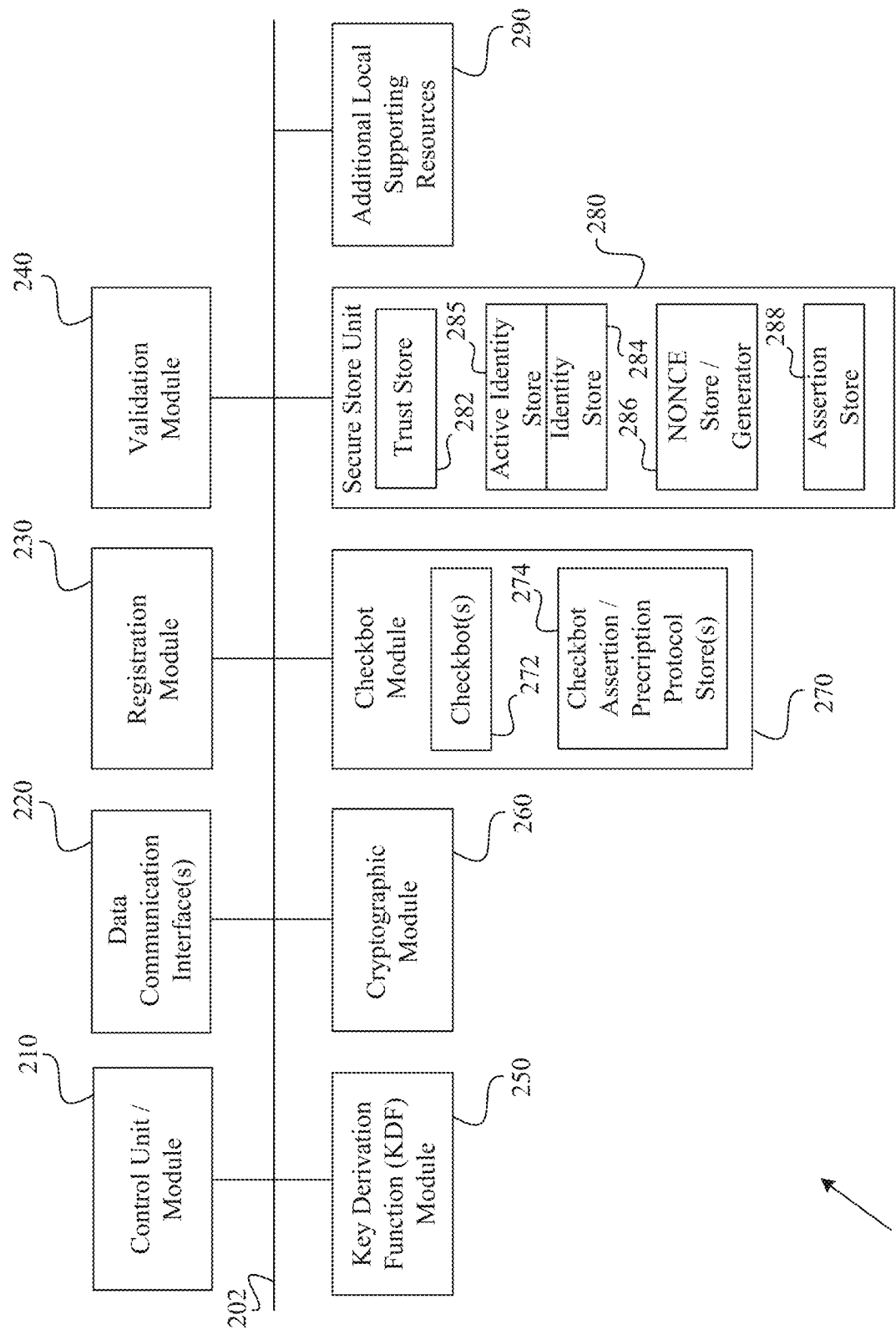
FIG. 6 is a block diagram showing aspects of a PIIM in accordance with various embodiments of the present disclosure.

FIGS. 6 and 7A-7H indicate or illustrate non-limiting representative aspects of a PIIM 200 and particular direct trust processes or operations performed thereby in accordance with an embodiment of the present disclosure. As shown in FIG. 6, in an embodiment a PIIM 200 is coupled to or includes a control unit/module, controller, or control circuitry 210, and a data communication interface 220. The PIIM 200 further includes a registration module 230; a validation module 240; a key derivation and/or generation function (KDF) module 250; a cryptographic module 260; a checkbot module 270 that provides a set of checkbots 272 as well as at least one secure checkbot assertion/prescription protocol store 274; and a secure store unit 280 that provides a trust store 282, an identity store 284 coupled to or including an active identity store 285, a NONCE store and/or generator (e.g., a random number generator) 286, and an assertion store 288. The PIIM 200 can further include additional and/or other local supporting or associated hardware and/or software resources 290, such as data processing, computation, or computing resources, and/or data storage resources. Each of the foregoing elements can be configured for communication or coupled by way of a particular data transfer or communication pathways 202. Depending upon embodiment details, particular portions of a given PIIM 200 can be implemented in hardware and/or software (e.g., at least portions of at least some of the registration module 230, the validation module 240, the KDF module 250, the cryp-tographic module 260, the checkbots 272, and the NONCE generator 286 can be implemented by way of program instruction sets that are executable by the control unit/module 210).

The control unit/module 220 includes a processing unit (e.g., integrated circuitry configured as a microcontroller or microprocessor, and at least one memory associated therewith) configured for coordinating, controlling, and/or performing PIIM operations, such as by way of the execution of program instructions (e.g., a PIIM control program) stored in a PIIM-based memory. The data communication interface 220 includes conventional circuitry for managing data communication between the PIIM 200 and external systems, apparatuses, or devices.

The registration module 230 is configured for registering one or more unique identities corresponding to the patient, where each unique patient identity is generated in association with the cryptographic module 260 and the KDF module 250; and storing each such unique patient identity in the identity store 284. Individuals having ordinary skill in the relevant art will understand that the cryptographic module 260 can include a random number generator and one or more auxiliary modules (e.g., program instruction sets) which when executed perform operations in accordance with cryptographic protocols. A given patient identity within the identity store 284 can become an active patient identity within the active identity store 285 by way of patient interaction with the validation module 240, which in response to patient input and/or patient actions manages or performs patient identity validation, authentication, and/or authorization operations based on patient input (e.g., a password or PIN) and/or patient biometric data. The patient can also de-register or revoke a previously-registered identity. Once a given registered patient identity itself is revoked, that instance of the patient identity cannot be regenerated, and thus the revocation of this patient identity is privacy preserving. Moreover, the patient's care provider can no longer decrypt future biomarker monitoring device readings or data corresponding to the specific four-actor-relationship (i.e., trust relationship) based on or linked with this revoked patient identity; rather, a new re-registration and authorization of the care provider must be performed under another/new active patient identity to re-establish full trust and functionality across the four-actor trust model.

Once a specific patient identity is confirmed as the active patient identity (e.g., a previously generated and stored specific patient identity is validated, authenticated, and/or authorized in response to patient input, and/or input by their designated delegate(s)), the PIIM 200 can perform operations in the context of this specific patient identity. More particularly, the registration module 230 is configured for managing the registration or enrollment of one or more biomarker monitoring devices 400 corresponding to the active patient identity, if they were not previously registered or enrolled for the active patient identity; and the validation module 240 and checkbot module 270 are configured for validating the identity and hardware/software integrity of a given biomarker monitoring device 400 under consideration in the context of the active patient identity.

Further to the foregoing, after an active patient identity has been confirmed, the PIIM 200 can establish a communication session with a particular biomarker monitoring device 400 (e.g., in response to patient action or input). As part of this communication session, a PIIM checkbot 272 can validate the identity of this biomarker monitoring device 400 and its hardware and/or software integrity (or lack thereof). For instance, in association with secure boot protocol validation operations corresponding to the biomarker monitoring device 400, the checkbot 272 can authenticate and authorize at least one digital signature, key hashed message authentication code, or message authentication code received from the biomarker monitoring device 400. In various embodiments, multiple biomarker monitoring device trust authorities are pre-programmed into the trust store 282 (e.g., in association with or at the time of PIIM manufacture), such that the checkbot 272 can perform a lookup operation in the trust store 272 to determine whether a set of digital signatures, key hashed message authentication codes, or message authentication codes received from the biomarker monitoring device 400 under consideration have been generated by a trusted authority or one of the trusted authority's delegates in a chain of trust, in accordance with well-known techniques in the cryptographic arts, indicating whether this biomarker monitoring device 400 comes from a trusted manufacturer or source. If so, and the biomarker monitoring device's hardware and/or software integrity are validated during the communication session under consideration, this particular biomarker monitoring device 400 can be trusted during this communication session. If this biomarker monitoring device 400 had not been previously registered or enrolled, the registration module 230 can receive or determine a unique device identity corresponding to this biomarker monitoring device 400, and store the unique device identity in the identity store 284. In certain embodiments, the unique device identity includes a biomarker monitoring device manufacturer designation, a unique biomarker monitoring device serial number, and possibly a biomarker monitoring device manufacture date; and/or a unique code generated by the cryptographic module 260 (e.g., which can be based upon such manufacturing-related information).

Once the PIIM 200 has validated a registered or enrolled biomarker monitoring device 400 under consideration, the PIIM's cryptographic module 260 can generate an ephemeral encryption key and communicate it to the biomarker monitoring device 400, which the biomarker monitoring device 400 can use to encrypt patient biomarker data during an associated biomarker acquisition or monitoring session corresponding to the currently active patient identity. Alternatively, during this biomarker acquisition or monitoring session, the biomarker monitoring device 400 can delegate biomarker data encryption tasks directly to the PIIM's cryptographic module 260.

Following the storage of a unique device identity corresponding to a newly registered or enrolled biomarker monitoring device 400 in the identity store 284, the registration module 230, in association with the cryptographic module 260, is additionally configured for generating or making accessible a biomarker data decryption key corresponding to the active patient identity and this biomarker monitoring device 400. More particularly, a one-time biomarker data decryption code corresponding to the active patient identity and this biomarker monitoring device 400 can be associated with a one-time use code, which can be encoded or incorporated in a digital, visual, or graphical object such as a matrix barcode or a Quick Response (QR) code. The PIIM 200 or the patient can communicate the one-time code, or a visual or graphical object corresponding thereto, over a secure communication channel to a specific provider associated with the patient, such that the provider can validate this one-time code, and a provider computing device corresponding to this provider can use the validated one-time code as part of an encryption scheme/protocol used in obtaining or deriving the biomarker data decryption key corresponding to the currently active patient identity and this biomarker monitoring device 400, thereby enabling the provider computing device to decrypt biomarker data corresponding to the currently active patient identity and this biomarker monitoring device 400 (e.g., after any biomarker data generated in association with a biomarker acquisition or monitoring session corresponding to this patient identity and the biomarker monitoring device 400 under consideration has been received by the provider computing device). As part of provider validation of the one-time code, data communication between a provider computing device and the PIIM 200 can occur, such that the validation module 240 can correspondingly validate the provider's identity. This can involve communication of an assertion signed by the provider's digital signature to the PIIM 200, and validation module determination of whether the assertion was signed by a trusted authority or the trusted authority's delegate by looking up an entry corresponding to this provider in the trust store 282.

Typically, a biomarker data decryption key can correspond to or is generated from (i) a key pair based on a first key corresponding to the active patient identity, and a second key corresponding to a specific biomarker monitoring device 400; or (ii) a key triplet based on a first key corresponding to the active patient identity, a second key corresponding to a specific biomarker monitoring device 400, and a third key corresponding to a specific validated care provider identity, depending upon embodiment details. The key triplet can thus correspond to or be generated from the aforementioned key pair and a third provider-specific key. The aforementioned ephemeral key can optionally be encrypted with the key pair, or the key triplet, in which case the specific provider corresponding thereto is the only party who can decrypt the one-time use code (e.g., in accordance with best practices in the cryptographic art) in a manner that individuals having ordinary skill in this art will comprehend.

In view of the foregoing, once a specific provider has obtained or received a biomarker data decryption key, this provider (e.g., by way of a provider computing device) can decrypt biomarker data associated with the patient and the specific biomarker monitoring device 400 corresponding to the biomarker data decryption key. Moreover, this provider can digitally sign and/or encrypt data or messages sent back to one or more of the PIIM 200, a patient computing device (e.g., a mobile phone), and/or this biomarker monitoring device 400. Additionally, the provider can negotiate future ephemeral keys with the PIIM 200 in accordance with standard or best practices in the cryptographic art, in a manner that individuals having ordinary skill in this art will comprehend. It can be noted that if a patient identity associated with a biomarker decryption key is revoked or de-registered from the PIIM 200, then any future biomarker data linked to this patient identity cannot be decrypted by the provider (as the decryption key will no longer be valid).

A provider computing device 100 can transfer a current prescription intended for a specific patient to a patient computing device, a PIIM 200, or a patient-side biomarker monitoring device 400 associated with the patient. In some embodiments, the current prescription's protocol can be stored in a checkbot assertion/prescription protocol store 274 of the checkbot module 270; and in other embodiments, the current prescription protocol can be stored in another memory or data store (e.g., which is accessible to or associated with the prescription management agent 500). A prescription checkbot 272 is configured for validating, authenticating, and/or authorizing that the current prescription using the currently active patient identity and provider digital signature information associated with or incorporated into the current prescription was generated by a trusted authority or that trusted authority's delegate. The prescription checkbot 272 can access the trust store 282 in association with validating or authenticating this provider's current prescription.

A given current prescription is executable or executed by the prescription management agent 500, in association with a prescription checkbot 272 performing prescription protocol review operations using information from the checkbot assertion/prescription protocol store 274 and/or the assertion store 288, which contain a customizable set of assertions that can be updated by the patient's care provider or other trusted authority, such that the prescription checkbot 272 can validate prescriptions and/or measurements associated therewith to identify/recognize prescription-related error, contraindication, and/or alert conditions relevant to patient safety. More particularly, the prescription checkbot 272 processes information or data associated with each prescription-related state and correspondingly accesses the checkbot assertion/ prescription protocol store 274 and/or the assertion store 288 to determine whether any aspects of the prescription fall outside of or too closely approach recognized or established guidelines or contraindications for patient safety. If so, the prescription checkbot 272 can limit, restrict, or prevent the presentation of particular instructions, recommendations, or information to the patient, and/or the prescription management agent's adaptive (e.g., auto-adaptive) adjustment of particular prescription protocol parameters (e.g., increases or decreases in one or more patient activities, behaviors, therapies, and/or medications outside of a recognized safe range, or a likely assured safe range for the patient under consideration).

Particular aspects of certain PIIM-based trust processes or operational sequences are further detailed with respect to FIGS. 7A-7H.

Figure 7A:
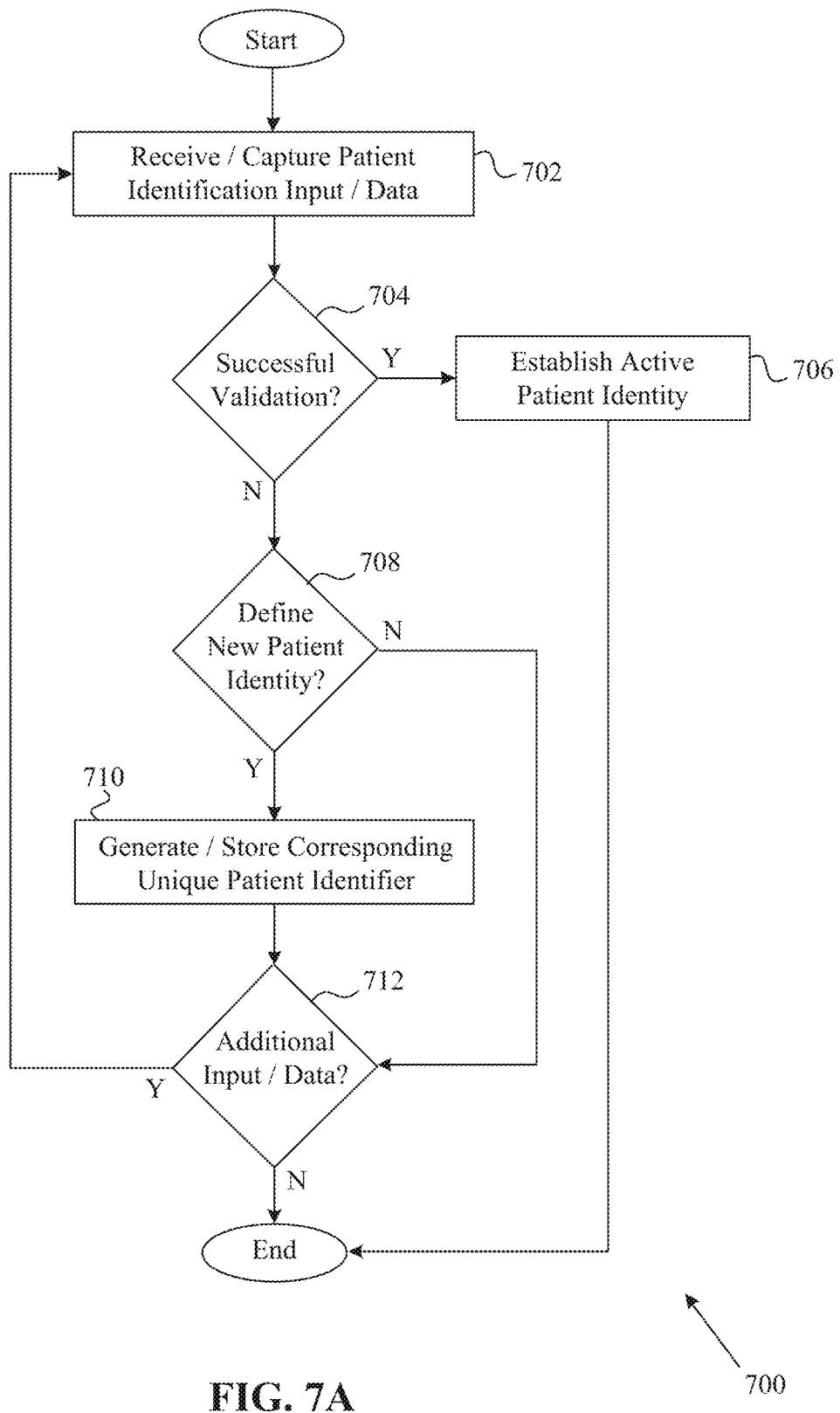
FIGS. 7A-7H illustrate aspects of a PIIM and particular direct trust processes or operations performed thereby in accordance with certain embodiments of the present disclosure.
Figure 7B:
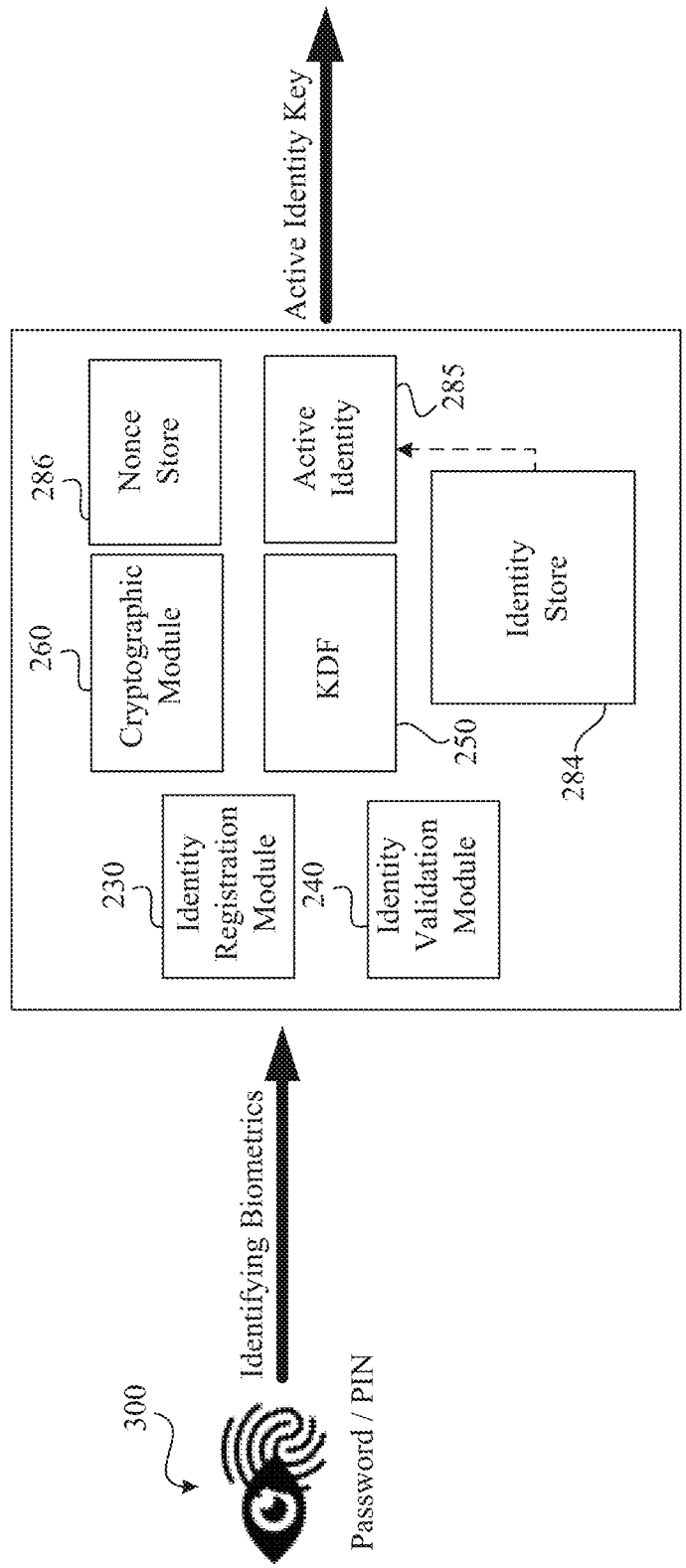

FIG. 7A is a flow diagram illustrating aspects of a non-limiting representative PIIM-based patient identity process or operational sequence 700 in accordance with an embodiment of the present disclosure, and FIG. 7B is a PIIM element diagram corresponding to FIG. 7A, indicating particular PIIM elements that can be involved in performing portions of such a process 700. In an embodiment, the process 700 includes a first process portion 702 involving receiving or capturing patient identification input from a patient identification unit/biometrics unit 300, which can include a patient password or PIN, and/or patient biometric data. A second process portion 704 involves attempting to validate this patient identifying information with respect to an already-existing patient identity within the identity store 284. If the patient identifying information can be validated, the corresponding patient identity within the identity store 284 is selected or established as the active patient identity in the active identity store 285. Otherwise, a new patient identity can be generated and stored in association with third and fourth process portions 708, 710; or additional patent information receipt or capture can be considered in association with a fifth process portion 712 (e.g. as in a situation in which the patient may want to delegate authority to a care provider), in which case the process 700 returns to the first process portion 702, or otherwise the process 700 ends.

Figure 7C:
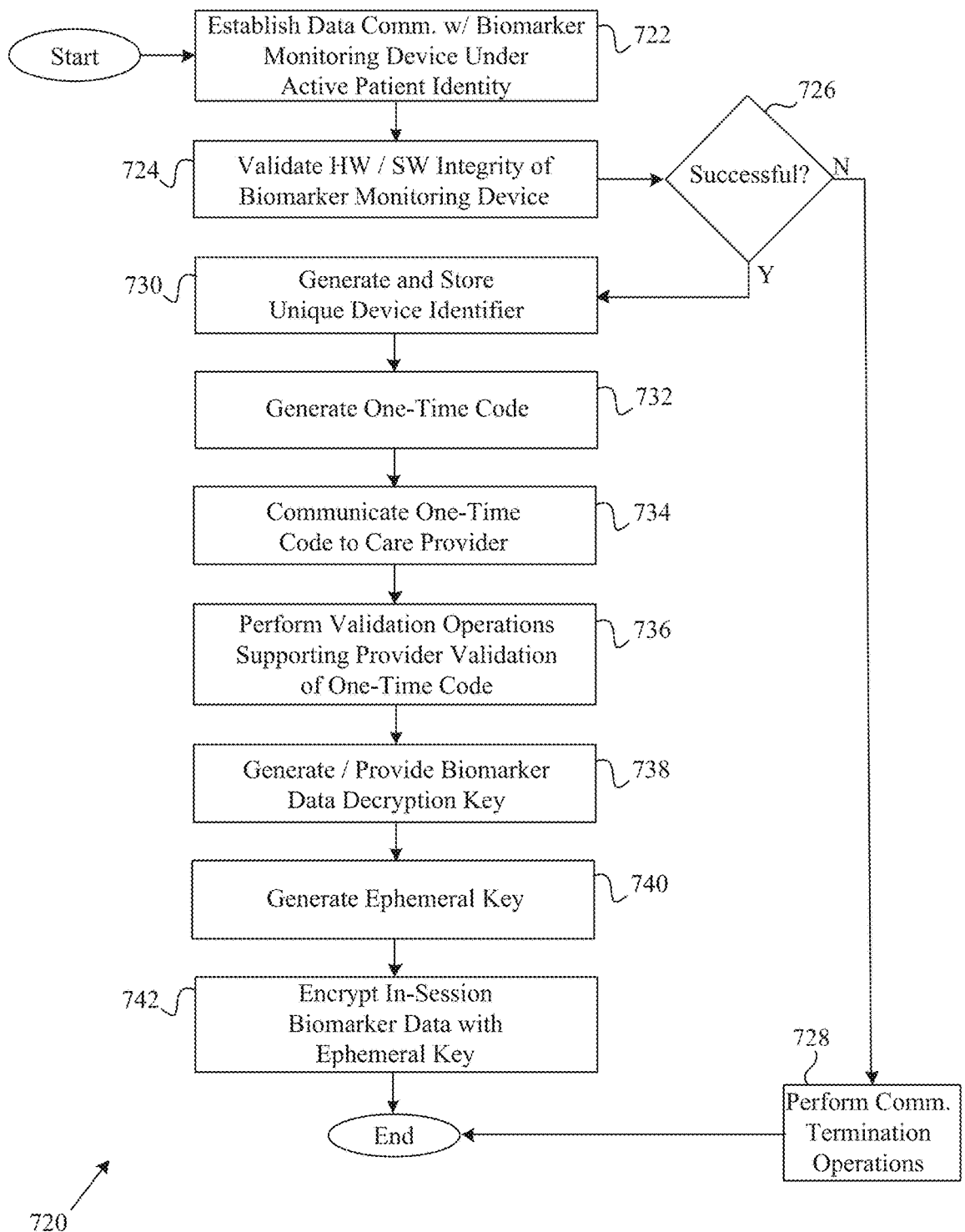
Figure 7D:
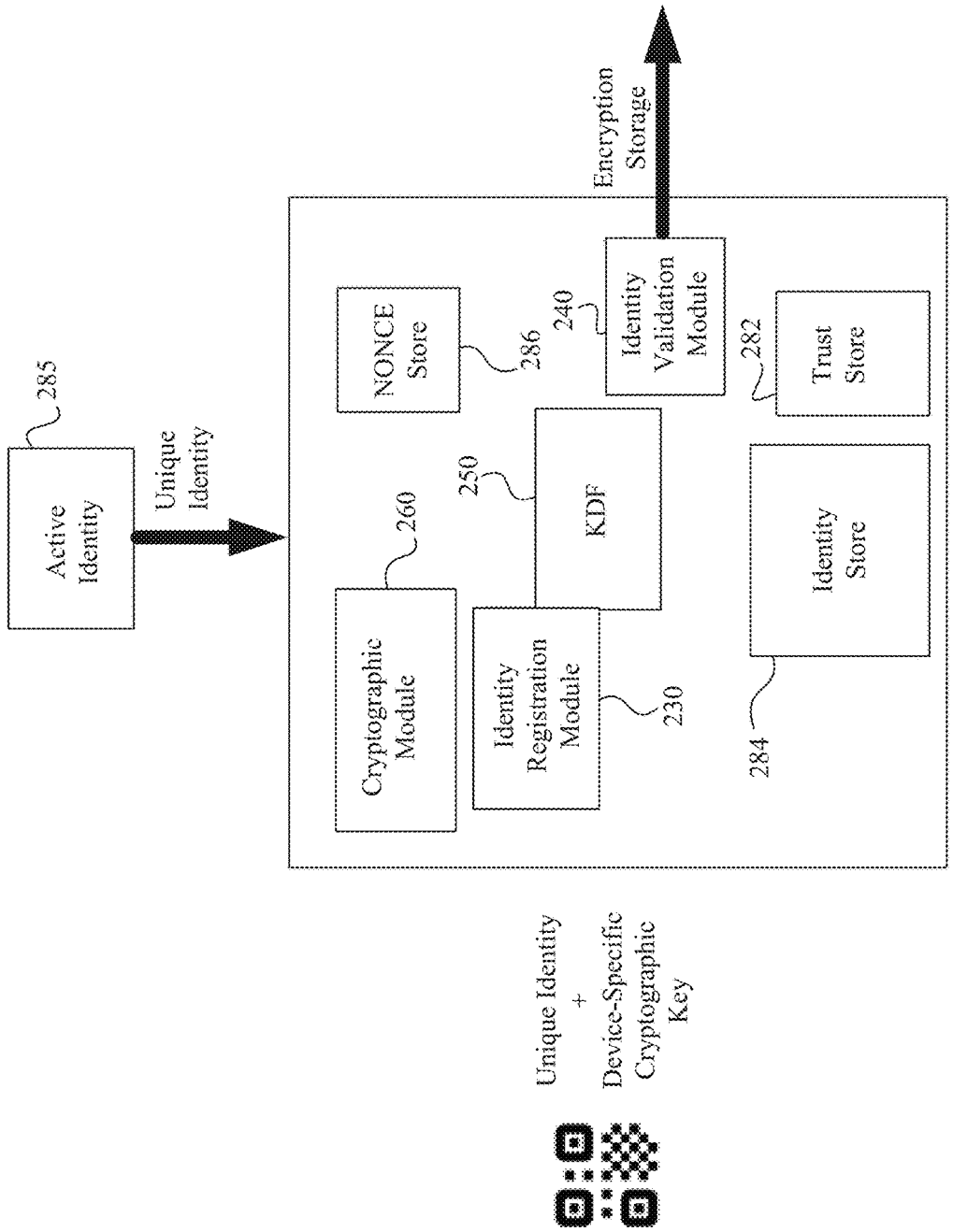
Figure 7E:
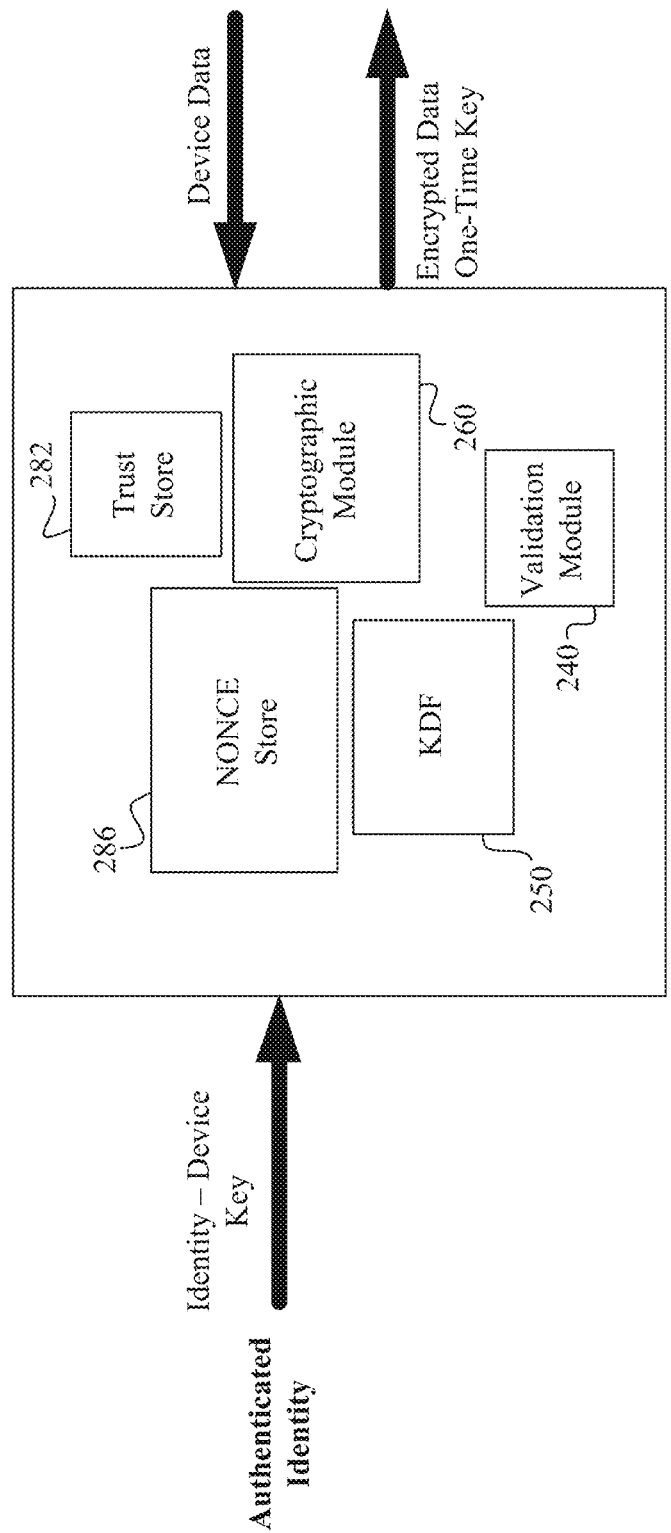

FIG. 7C is a flow diagram illustrating aspects of how the four-actor trust matrix or model of FIG. 5, and the trust relationships or trust assertions thereof or corresponding thereto, can be established or implemented for a non-limiting representative PIIM based biomarker monitoring device registration, care provider registration, and biomarker data encryption process or operational sequence 720 in accordance with an embodiment of the present disclosure; and FIGS. 7D and 7E are PIIM element diagrams corresponding to FIG. 7C, indicating particular PIIM elements that can be involved in performing portions of such a process 720. In an embodiment, the process 720 includes a first process portion 722 involving establishing, under an active patient identity, data communication with a particular biomarker monitoring device 400 that does not yet have a unique device identity stored in the identity store 284, to initiate or as part of establishing DTR-1 shown in FIG. 5. A second process portion 724 involves validation (e.g., attempting validation) of this biomarker monitoring device's hardware and/or software integrity, such as by way of receipt and validation of a set of digital signatures generated as part of a secure boot protocol process corresponding to the biomarker monitoring device 400. The second process portion 724 can involve cooperative operation between the validation module 240 and a checkbot 272. As part of such validation, the checkbot 272 can access an appropriate trust store 282 that contains valid and trusted biomarker monitoring device trust authorities. A third process portion 726 involves determining whether validation of the biomarker monitoring device's hardware and/or software integrity was successful, as part of establishing or attempting to establish DTR-2 shown in FIG. 5; and if successful, DTR-2 shown in FIG. 5 is established or effectively established. If the set of digital signatures cannot be successfully validated, the process 720 can transition to a fourth process portion 728 corresponding to data communication termination operations, which may involve the generation and presentation of a device validation failure message to the patient, such as "device not validated—not trusted," and/or the generation and transmission of a device validation failure message to the network-based resources 50 and/or an appropriate set of provider resources 1000. After the fourth process portion 728, the process 720 can end, or can be restarted (e.g., a predetermined limited number of times).

If the hardware and/or software integrity of this biomarker monitoring device 400 was successfully validated, thereby also establishing TTR-A shown in FIG. 5, a fifth process portion 730 can involve the generation of a unique device identity corresponding to the biomarker monitoring device 400, which may involve the cryptographic module 260, the KDF module 250, and the nonce store/generator 286, and storing this unique device identity in the identity store 284.

A sixth process portion 732 can involve the use or generation of a unique code (e.g., the one-time code as set forth above, or a different one-time code) based at least on the active patient identity and the unique biomarker monitoring device identity, where the one-time code can be encoded or embedded in or represented as a computer readable or electronically readable object, such as a digital, visual, or graphical object (e.g., a matrix bar code). A seventh process portion 734 can involve presentation or communication of the unique code or its visual representation to a particular care provider (e.g., by way of communication with a care provider computing device 1100) associated with the patient. If the identity of this care provider is known prior to the generation of the unique code, such that a corresponding unique care provider identity already exists in the identity store 284, the one-time code can be generated based on the active patient identity, the unique biomarker monitoring device identity, and the unique care provider identity.

An eighth process portion 736 can involve performing validation operations that support or enable care provider validation of the unique code, which can include data communication between a care provider computing device 1100 and the validation module 240.

It is important to note that execution or completion of the eighth process portion 736 facilitates the establishment of or establishes DTR-3, TTR-C, and TTR-B shown in FIG. 5, thereby implementing or completing the implementation of the four actor trust matrix model between the patient, the PIIM 200, the biomarker monitoring device 400, and the patient's care provider, thereby facilitating or enabling secure, authenticated, authorized, confidential, privacy-preserving, and integrity-preserving bi-directional communication of patient biometric information, biomarker data, and prescriptions.

Following care provider validation of the unique code, a ninth process portion 738 can involve the generation of a biomarker data decryption key for the care provider under consideration, and/or the provision of the biomarker data decryption key to this care provider. A tenth process portion 740 can involve the generation of an associated ephemeral key for encrypting the patient's biomarker data during the next biomarker data acquisition or monitoring session, and the transfer of the ephemeral key to the biomarker monitoring device 400 under consideration. Alternatively, the PIIM 200 can use the ephemeral key to encrypt the patient's biomarker data. An eleventh process portion 742 involves encrypting patient biomarker data using the ephemeral key during the next biomarker data acquisition or monitoring session.

It can be noted that in some embodiments, after the fourth or eleventh process portions 728, 742, the process 720 can return to the first process portion 722, for instance, as part of operations directed to establishing delegated trust.

Figure 7F:
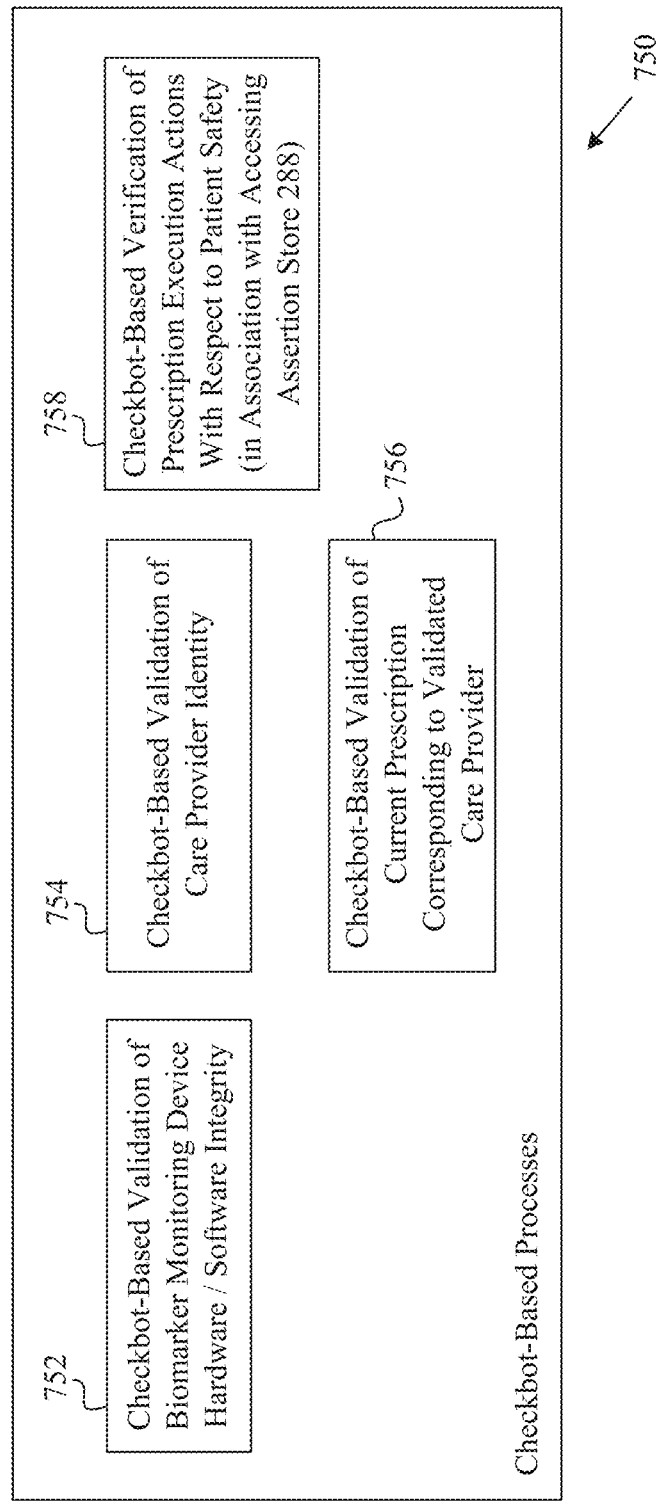
Figure 7G:
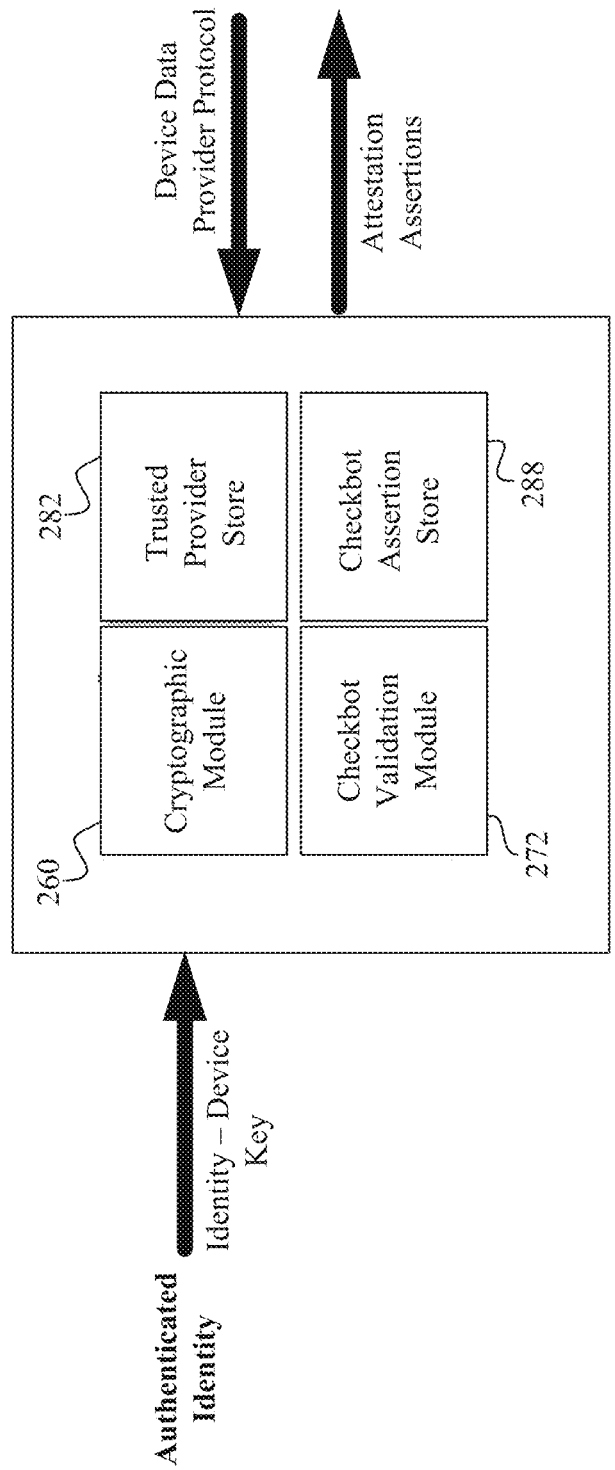

FIG. 7F is a flow diagram illustrating a set of non-limiting representative PIIM checkbot processes or operational sequences 750 performed by the checkbot module 272 in accordance with an embodiment of the present disclosure, and FIG. 7G is a PIIM element diagram corresponding to FIG. 7F, indicating particular PIIM checkbot-related elements that can be involved in such processes. In an embodiment, a first checkbot process 752 involves checkbot-based validation of biodata monitoring device hardware and/or software integrity (e.g., in a manner indicated herein). A second checkbot process 754 involves checkbot-based validation of one or more care provider identities (e.g., in a manner indicated herein). A third checkbot process 756 involves checkbot-based validation of each current prescription received from a validated care provider (e.g., in a manner indicated herein). A fourth checkbot process 758 involves checkbot-based verification of prescription execution actions using the checkbot assertion/prescription protocol store 274 and/or the assertion store 288 with respect to ensuring patient safety corresponding to prescription execution by the prescription management agent 500, including prescription execution actions associated with the communication of data to one or more patient computing devices 100 for the provision or presentation of feedback, instructions, coaching, guidance/advice, reminders, and/or recommendations to the patient (e.g., in a manner indicated herein). As indicated above, the checkbot assertion/prescription protocol store 274 and/or the assertion store 288 can contain a customizable set of assertions, which can be updated by the provider and/or other trusted authority, and which a checkbot 272 can access as part of each state transition by the prescription management agent 500 to validate prescriptions and measurements associated therewith for errors and/or alert conditions relevant to patient safety.

Figure 7H:
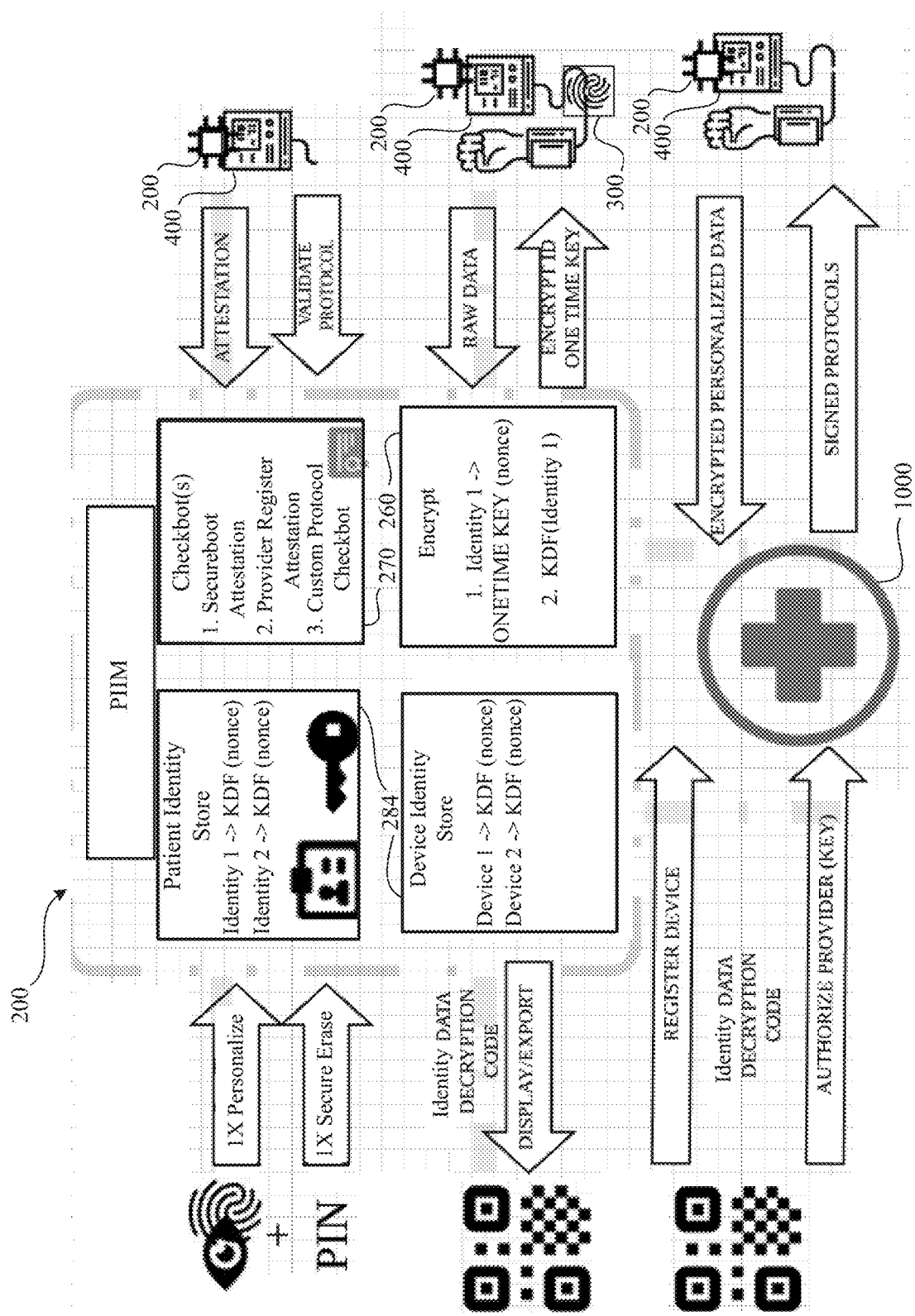

FIG. 7H is a PIIM element diagram indicating various operational sequences performed by particular PIIM elements in order to establish/implement and operate under the four actor trust model of FIG. 5, in association with patient registration and validation; biomarker monitoring device registration and validation; care provider registration and validation; prescription communication; biomarker data decryption key provision; and secure/encrypted biomarker data acquisition or generation and communication. Various aspects of FIG. 7H correspond to PIIM structure(s) and operation(s) described in detail above, by which direct trust relationships and transitive trust relationships are established in accordance with an implementation (e.g., a physical implementation or instantiation) of the four actor trust model shown in FIG. 5.

Additional aspects of certain non-limiting representative types of PIIM and biomarker monitoring device configurations are detailed with respect to FIGS. 8A-8E.

Figure 8A:
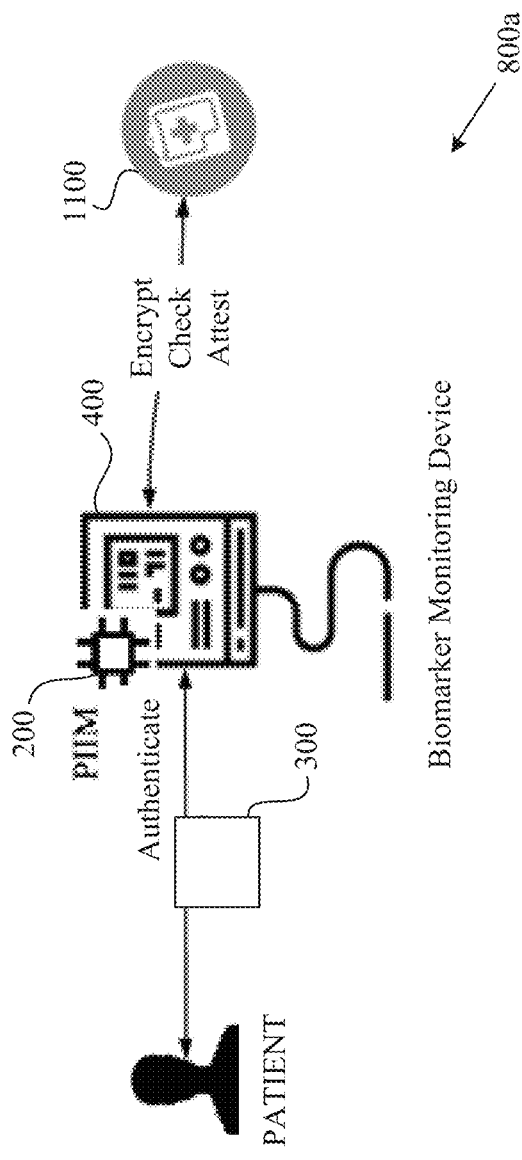
FIG. 8A is a block diagram showing a PIIM-biomarker monitoring device operational configuration in accordance with an embodiment of the present disclosure.

FIG. 8A is a block diagram showing a PIIM-biomarker monitoring device operational configuration 800a in accordance with an embodiment of the present disclosure. As indicated in FIG. 8A, a biomarker monitoring device 400 can be equipped with a PIIM 200, and a specific patient can be associated with that PIIM 200 by way of a patient password/PIN and/or patient biometric information using a corresponding patient identification/biometrics unit 300.

Figure 8B:
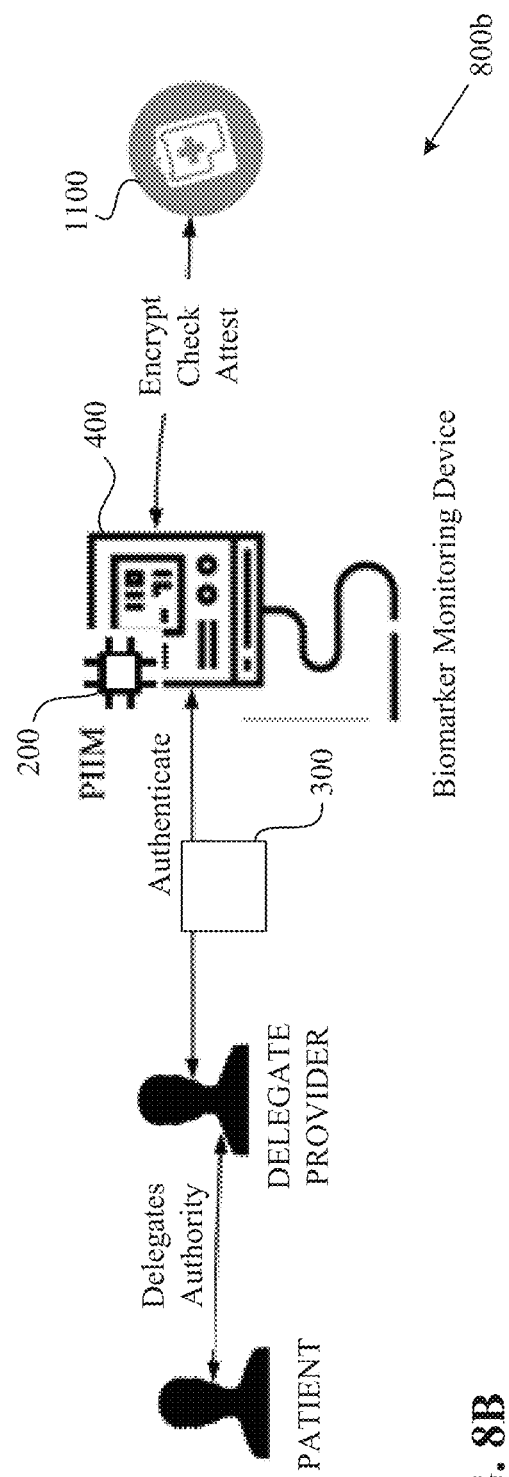
FIG. 8B is a block diagram showing a PIIM-biomarker monitoring device operational configuration in accordance with another embodiment of the present disclosure.

FIG. 8B is a block diagram showing a PIIM-biomarker monitoring device operational configuration 800b in accordance with another embodiment of the present disclosure, which is an alternative embodiment analogous to that shown in FIG. 8A. As indicated in FIG. 8B, a patient can delegate, as described elsewhere herein, their identity authentication or validation to a (trusted) third party, such as a caretaker or nurse, and this third party can be associated with the PIIM 200 by way of a password/PIN and/or biometric information corresponding to the third party using the patient identification/biometrics unit 300.

Figure 8C:
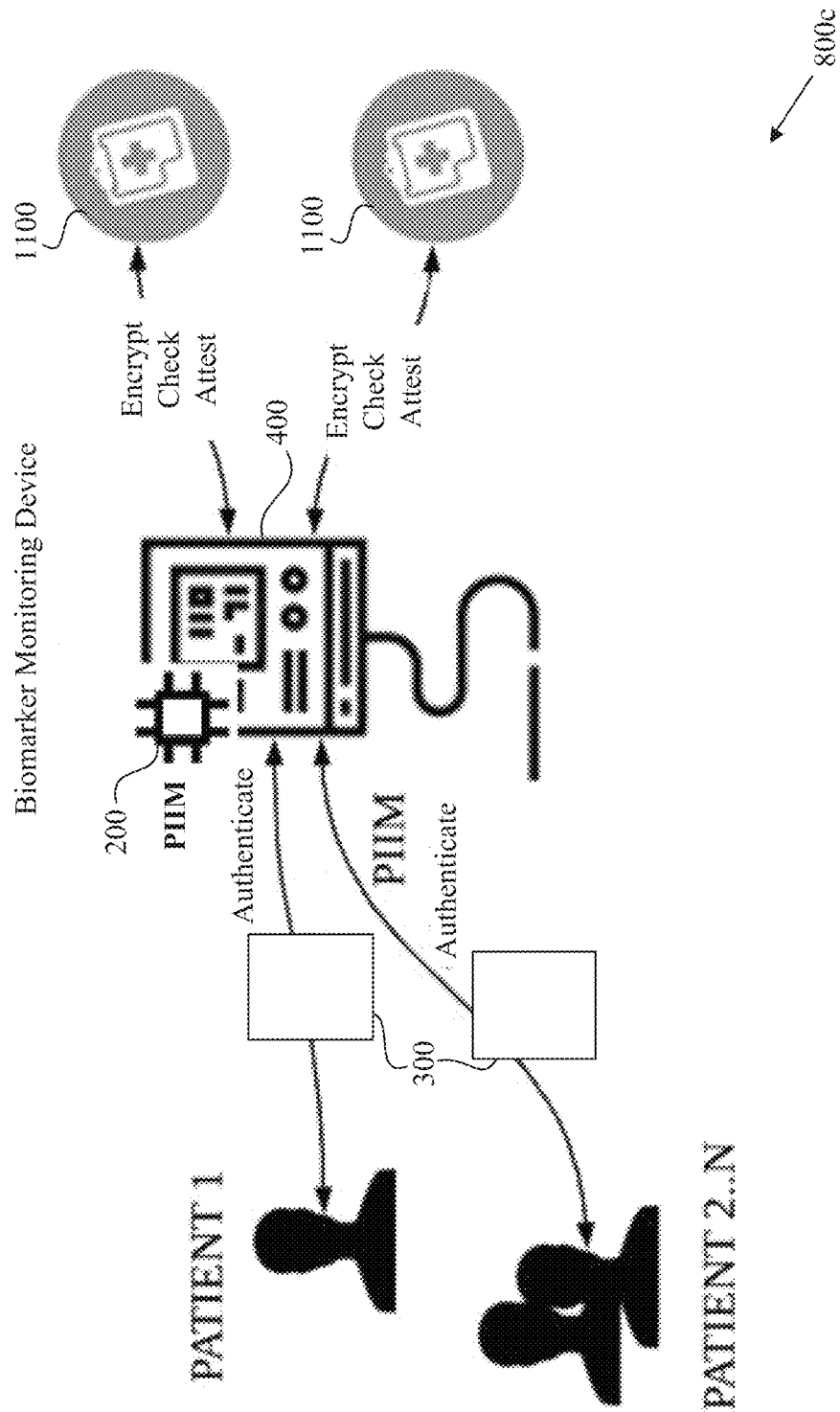
FIG. 8C is a block diagram showing a PIIM-biomarker monitoring device operational configuration in accordance with a further embodiment of the present disclosure.

FIG. 8C is a block diagram showing a PIIM-biomarker monitoring device operational configuration 800c in accordance with a further embodiment of the present disclosure. As indicated in FIG. 8C, a single biomarker monitoring device 400 and a single PIIM 200 (e.g., incorporated into the biomarker monitoring device 400) can operate across multiple distinct patients that each are associated with the PIIM 200 by way of passwords/PINs and/or biometric information corresponding to each of such patients using a patient identification/biometrics unit 300. The PIIM 200 can authenticate the identity of each individual patient, and can register each patient; validate the identity of a care provider corresponding to each patient; receive from such care providers current prescriptions corresponding to their PIIM-registered patients, and validate such prescriptions; execute such prescriptions on a patient-specific basis; and selectively communicate patient-specific data to the appropriate care providers. Thus, FIG. 8C illustrates a multiple/many patient to single biomarker monitoring device 400/single PIIM 200 to multiple care provider operational configuration.

Figure 8D:
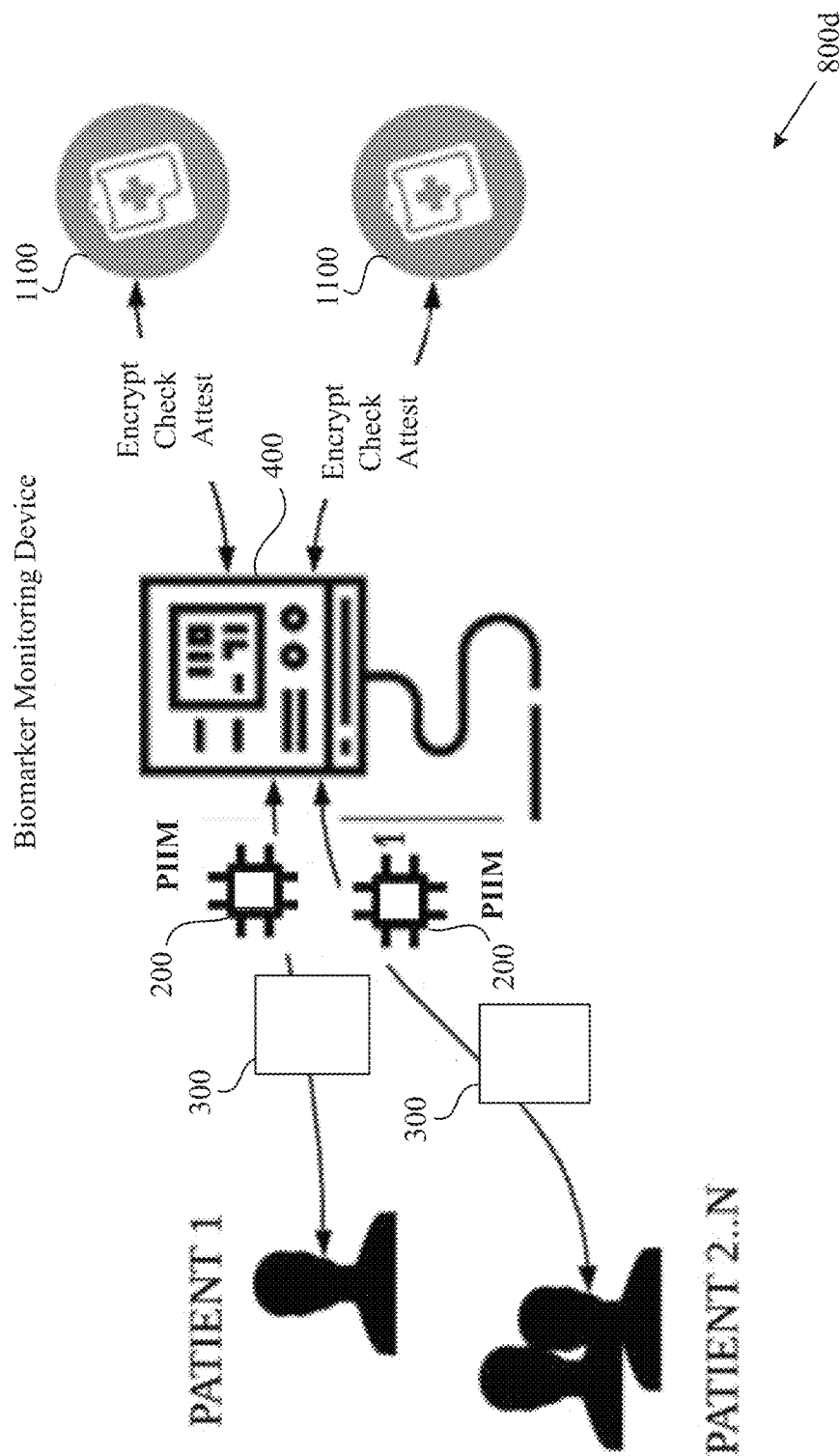

FIG. 8D is a block diagram showing a PIIM-biomarker monitoring device operational configuration 800d in accordance with yet another embodiment of the present disclosure. As indicated in FIG. 8D, among multiple patients, each patient can have a distinct PIIM 200 and a distinct patient information/biometric unit 300 (e.g., which are carried by a distinct patient computing device corresponding to each patient), and each patient can interact with a single biomarker monitoring device 400. The biomarker monitoring device and each patient computing device can handle care provider identity validation, prescription validation, and biomarker data communication corresponding to the patient's care provider. Hence, FIG. 8D illustrates a multiple/many patient and associated multiple/many patient identity authentication/PIIM 200 devices to single biomarker monitoring device 400 to multiple care provider operational configuration.

Figure 8E:
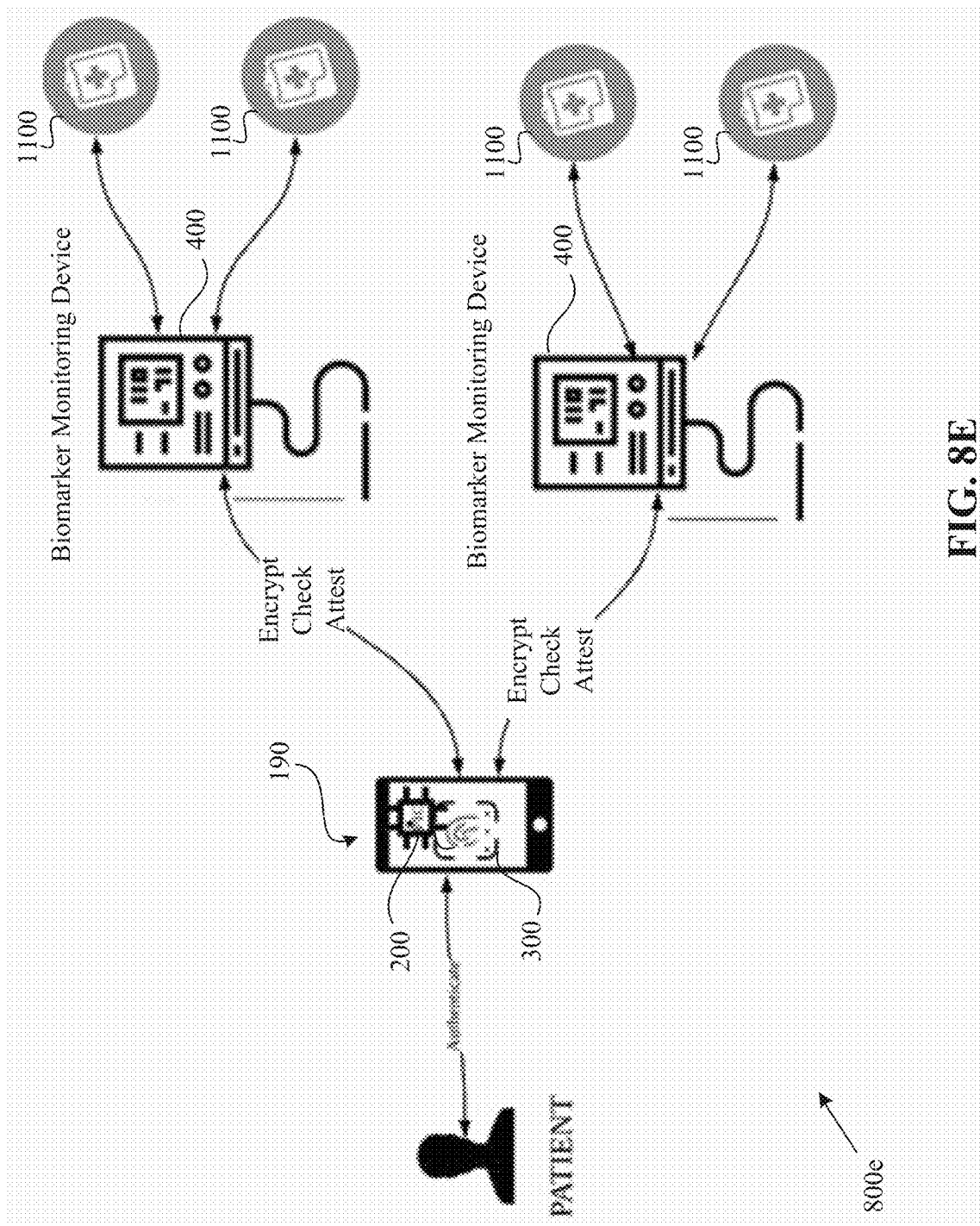

FIG. 8E is a block diagram showing a PIIM-biomarker monitoring device operational configuration 800*e* in accordance with an additional embodiment of the present disclosure. As indicated in FIG. 8E, a given patient's PIIM 200 and patient identity/biometric unit 300 can be implemented by way of a patient computing device 190, which can communicate with any of multiple registered biomarker monitoring devices 400, which can validate the identities of, receive and validate current prescriptions from, and communicate patient biomarker data to any of multiple care providers associated with the patient. FIG. 8D thus illustrates a single PIIM-enabled and patient identification/biometric unit enabled patient computing device to multiple/many biomarker monitoring device to multiple care provider operational configuration.

It can be noted that embodiments in accordance with the present disclosure are not limited to only the operational configurations shown in FIGS. 8A-8E, and additional/other operational configurations can exist which fall within the scope of the present disclosure.

Aspects of Self-Contained Prescription Management
With reference again to FIGS. 3A and 6, the prescription management agent 500 in association with a prescription checkbot 272 and the checkbot assertion/prescription protocol store 274 and/or the assertion store 288 can manage the performance of, execute, carry out, or implement a current prescription verification protocol. The prescription management agent 500 can be configured for automatically generating, communicating, and/or presenting feedback, instructions, coaching, guidance/advice, reminders, and/or recommendations relating to the current prescription protocol to the patient (e.g., by way of data communication with a set of patient computing devices); performing biomarker data analysis and prescription compliance support processes, including determining, confirming, or requesting patient confirmation of compliance with their current prescription protocol; possibly adaptively or dynamically providing the patient with feedback and/or guidance based on patient input and/or biomarker data and/or prescription compliance analysis (e.g., to aid or encourage the patient in successfully complying with their current prescription); and possibly adaptively or dynamically adjusting particular aspects of the current prescription protocol, e.g., based on a determination of an extent of patient prescription compliance in view of acquired or analyzed patient biomarker data. The prescription checkbot 272 can be configured for performing patient safety verification processes or operations for various prescription management agent processes or operations, such as presenting instructions, coaching, guidance, reminders, recommendations, and/or feedback to the patient, and/or adaptively adjusting one or more aspects of the current prescription protocol. For instance, the prescription checkbot 272 can be configured for verifying patient safety with respect to information that the prescription management agent 500 intends to communicate to the patient in association with one or more or each state transition.

In association with executing the current prescription protocol, the prescription management agent 500 can communicate, deliver or send messages to the patient by way of in-app social media messaging (e.g., using WhatsApp or an additional/other social media app), simple messaging service (SMS) messages, and/or phone calls. The prescription management agent 500 may transition to or generate states that require that the patient be consulted or queried, such that additional contextual information can be obtained from or submitted by the patient (e.g., by way of patient input, such as patient response(s) to a question/questionnaire or survey). While the majority or vast majority of data communication relating to prescription management occurs between the prescription management agent 500 and particular patient-side electronic/computing devices by which information can be presented to the patient, and thus the majority or vast majority of data communication involving the prescription management agent is self-contained with respect to a given set of patient-side resources 100, the prescription management agent 500 may in certain situations transition to or generate states that require the communication or transmission of patient-related data to the patient's care provider or one or more members of the patient's care team (e.g., particular clinical staff), which can result in provider-side communication with the prescription management agent 500 and/or the patient (e.g., by way of messaging and/or a phone call).

It can be noted that the prescription management agent 500 efficiently and effectively enables or provides continuous, uninterrupted, generally continuous, or generally uninterrupted prescription management services or operations, including patient monitoring and advisory services or operations, even when data communication networks external to the set of patient-side resources 100 with which the prescription management agent 500 is associated are experiencing data communication slowdowns or interruptions.

Figure 9:
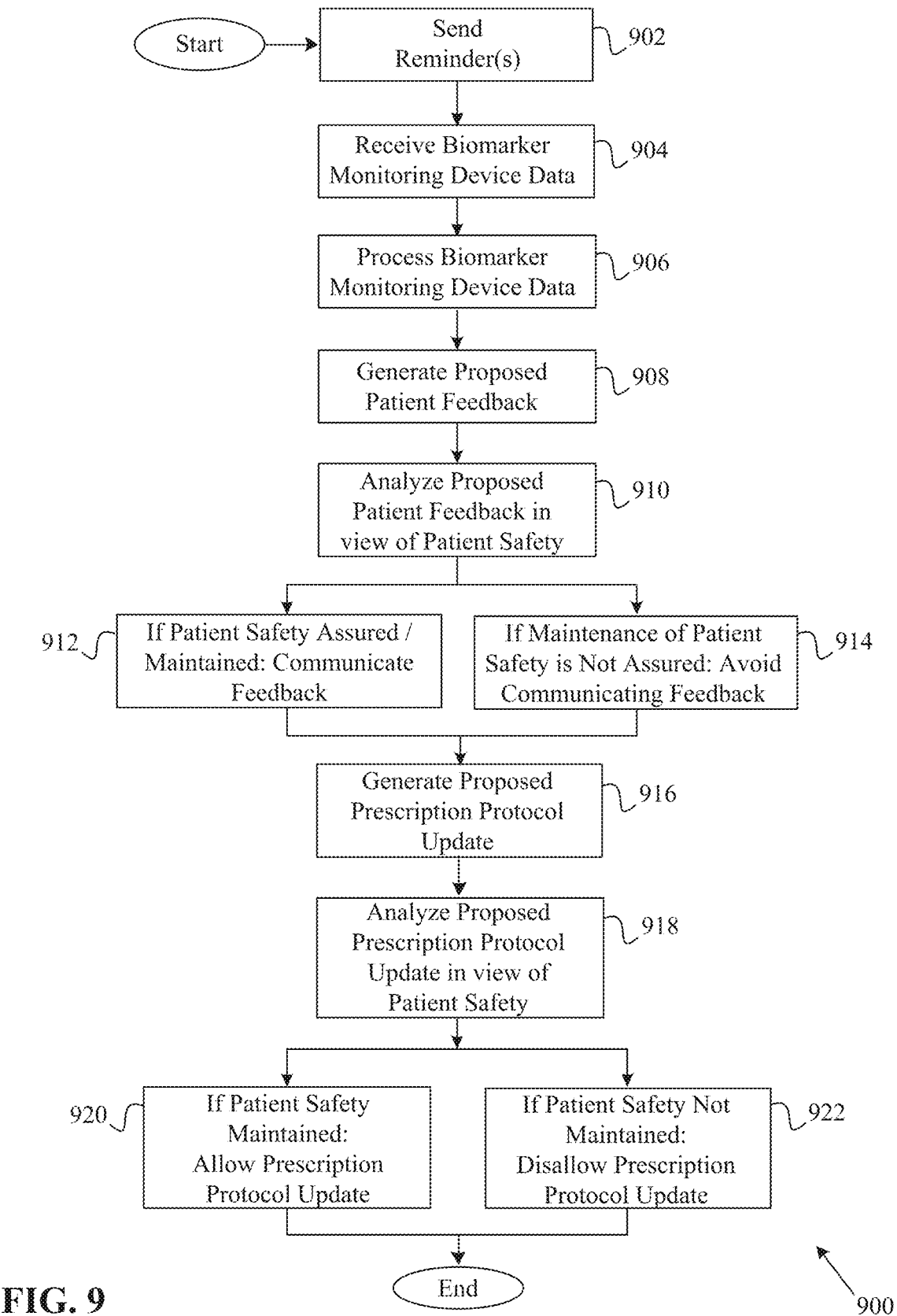
FIG. 9 is a flow diagram showing aspects of a current prescription protocol execution process in accordance with an embodiment of the present disclosure.

FIG. 9 is a flow diagram showing aspects of a current prescription protocol execution process 900 in accordance with an embodiment of the present disclosure. In an embodiment, the process 900 includes a first process portion 902 involving sending one or more biomarker data acquisition or monitoring session reminders and/or invitations (e.g., calendar invitations) to a set of patient computing devices; a second process portion 904 involving receiving or obtaining and storing patient biomarker data during one or more biomarker data acquisition or monitoring sessions; a third process portion 906 involving processing or analyzing such biomarker data; a fourth process portion 908 involving generating proposed feedback, instructions, coaching, guidance/advice, reminders, and/or recommendations for the patient; a fifth process portion 910 involving processing and verification of such feedback, instructions, coaching, guidance/advice, reminders, and/or recommendations with respect to patient safety by a prescription checkbot 272 and its accessing the assertion store 272; a sixth process portion 912 involving communication of such feedback, instructions, coaching, guidance/advice, reminders, and/or recommendations to one or more patient computing devices 190 if patient safety is assured, maintained, or ensured; and a seventh process portion 914 involving limiting/restricting, avoiding, or preventing the communication of such feedback, instructions, coaching, guidance/advice, reminders, and/or recommendations to such patient computing devices 190 if patient safety may not be, is likely not, or is not assured or maintained (e.g., if assurance/maintenance of patient safety may be questionable). A possible eighth process portion 916 can involve generating a proposed prescription protocol update or revision based on processing or analysis of patient biomarker data (e.g., where the proposed prescription protocol update can correspond to a revision of a biomarker data monitoring schedule, an exercise routine, a set of dietary recommendations, a medication schedule, and/or a medication dosage for the patient); a ninth process portion 918 can involve prescription checkbot processing and verification of the proposed prescription protocol update with respect to patient safety; a tenth process portion 920 can involve updating or revising the prescription protocol in accordance with the proposed prescription protocol update in the event that patient safety is maintained or ensured; and an eleventh process portion 922 can involve preventing prescription protocol update in the event that patient safety is not maintained or ensured.

Aspects of Data Communication Privacy

In view of the foregoing, the prescription management agent 500 facilitates, enables, or performs prescription management services or operations without or in the absence of unnecessary or unwanted communication of patient-related data to network-based resources 50 and provider-side resources 1000, and thus the prescription management operations can be referred to or defined as primarily, majority, substantially, or effectively self-contained (e.g., more than approximately 50%, 60%, 70%, 75%, 80%, 85%, 90%, 95%, or 97.5% depending upon embodiment and/or situational details) with respect to the set of patient-side resources 100 with which the prescription management agent 500 is associated. More particularly, the majority of or nearly all prescription management agent data communication operations (e.g., more than approximately 50%, 60%, 70%, 75%, 80%, 85%, 90%, 95%, or 97.5% of such operations depending upon embodiment or situational details) typically solely involve the set of patient-side resources 100 (e.g., in association with information transfer or exchange solely between the prescription management agent 500 and one or more patient computing devices) rather than involving network-based and/or provider-side resources 50, 1000 external or non-local to the set of patient side resources 100. For instance, in various embodiments more than 50% (e.g., 60%, 70%, 75%, 80%, 85%, 90%, 95%, or 97.5%) of prescription management agent data communication operations occur between the prescription management agent 500 and the set of patient-side resources 100, rather than involving network-based and/or provider-side resources 50, 1000 external or non-local to the set of patient-side resources.

Consequently, the amount of data communication that the prescription management agent 500 directs to network-based and/or provider-side resources 50, 1000 external to the set of patient side resources 100 is limited, reduced, greatly reduced, or minimized compared to conventional automated patient monitoring systems and techniques that communicate significantly more or much larger quantities of data, such as significant or large amounts of patient biomarker data acquired during a given biomarker acquisition or monitoring session and/or patient prescription compliance data, from a conventional biomarker monitoring device or a computing device associated therewith to non-local network-based or cloud-based systems and/or provider computing systems. Hence, self-contained prescription management operations in accordance with various embodiments of the present disclosure keep the majority or vast majority of patient-related data private with respect to a specific set of patient-side resources 100, which can reduce a likelihood that a patient data interception or beach event will occur (or reduce a frequency of such an occurrence) in association with prescription management operations.

Furthermore, the patient-side data communication manager 600 can manage, coordinate, or control (e.g., in a cooperative manner with the prescription management agent 500) the communication of patient-side data (e.g., which can include limited or small amounts of patient biomarker data, and/or notifications or alerts corresponding thereto) external to the set of patient-side resources 100. More particularly, the patient-side data communication manager 600 can manage or control, or further manage or control, the communication of patient-side data (e.g., contained in messages) to external or non-local destinations (e.g., systems, apparatuses, or devices external to a set of patient-side resources 100 under consideration, such as network-based computing resources 50, and/or a particular set of provider computing devices). In various embodiments, the data communication manager 600 manages or controls, or further manages or controls, the types of data that can (or cannot) or will (or will not) be communicated; data communication timing; and communicated data content with respect to the communication of data to external or non-local destinations. Patient-side data that can or which is intended to be communicated to one or more external destinations can include at least some acquired patient biomarker data and/or processed patient biomarker data corresponding to acquired patient biomarker data; specific types of patient health or medical condition data and/or corresponding indications (e.g., in the context of a medical emergency alert generated in response to the detection of a possible or likely medical emergency situation or event); and possibly some generated patient prescription compliance data, such as in the form of a monthly, quarterly, or annual summary (e.g., statistical summary), where such patient-related data can be stored in the communication/messaging store(s) 680 prior to such data communication. Patient-side data that can or which is intended to be communicated to one or more external destinations can omit or exclude normal, routine/ordinary, or non-emergency situation patient biomarker data (e.g., biomarker data that falls within an expected or typical/normal range or an expected population average for the patient), and/or non-summary data. Patient-side data that can or which is intended to be communicated to one or more external destinations can include dummy data, as further detailed below. Several embodiments in accordance with the present disclosure can mask or obscure the time at which patient biomarker data is acquired or generated, and/or communicated to external or non-local destinations following its acquisition or generation.

Figure 10A:
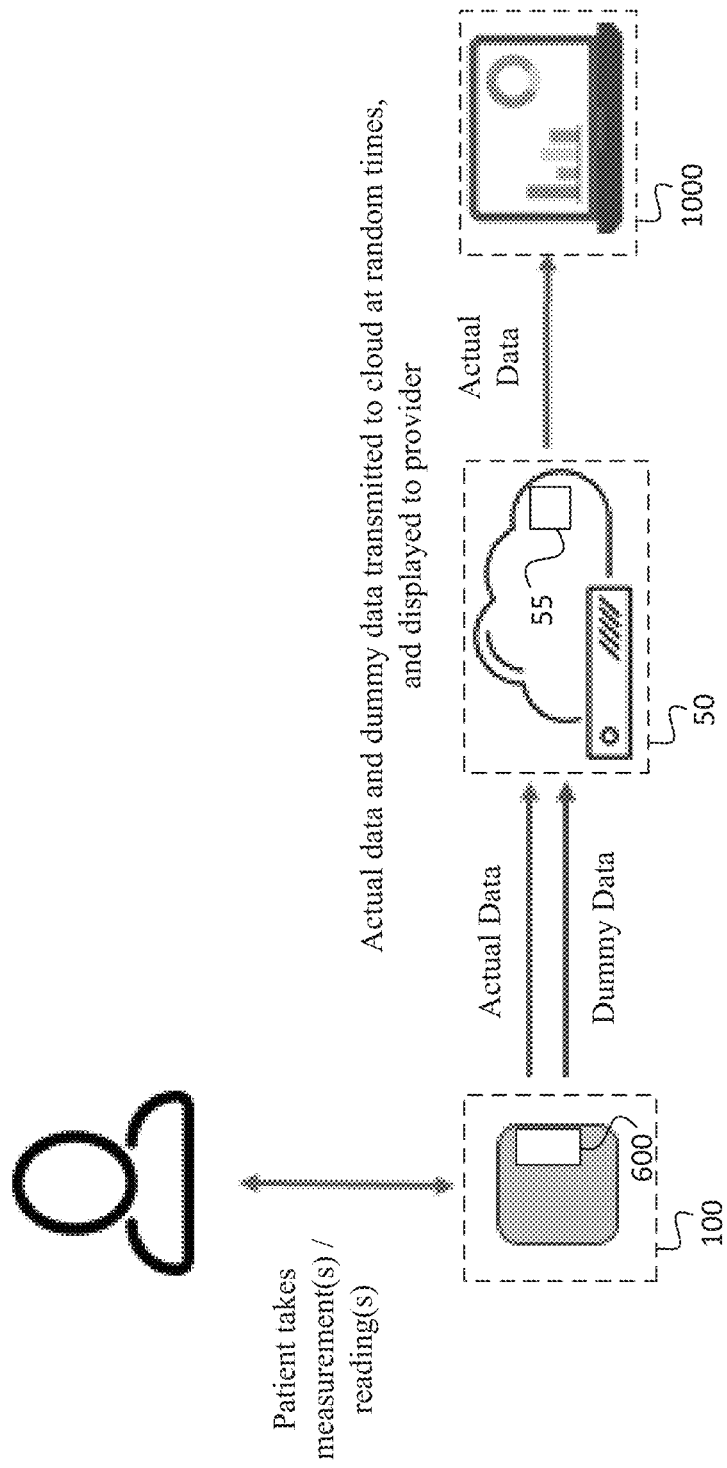
FIGS. 10A-10C illustrate particular aspects of data communication, including patient-data communication, from a set of patient-side resources to network-based resources and/or a set of provider-side resources in accordance with certain embodiments of the present disclosure.
Figure 10B:
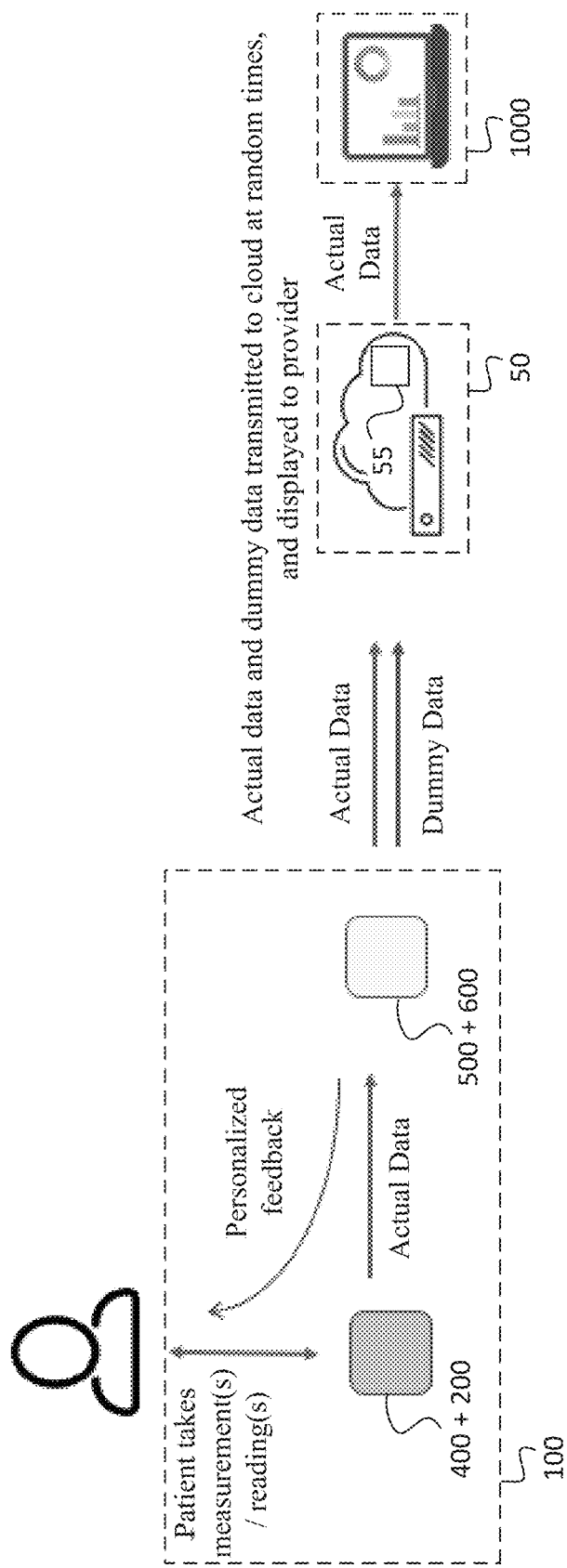
Figure 10C:
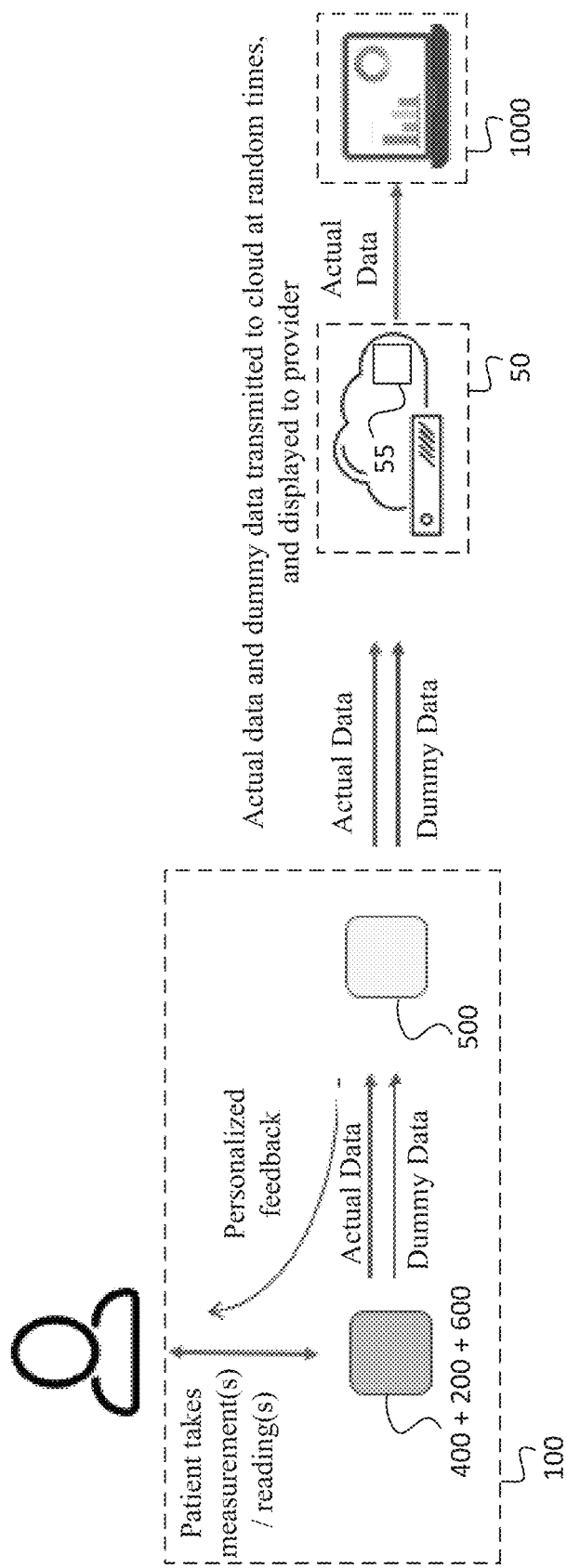

FIGS. 10A-10C illustrate particular aspects of data communication, including patient-data communication, from a set of patient-side resources 100 to network-based resources 50 and/or a set of provider-side resources 1000 in accordance with certain embodiments of the present disclosure. In multiple embodiments, as indicated in FIG. 10A the patient-side data communication manager 600 is configured for coordinating the sending or sending both dummy data (e.g., which is not actual patient data, or which excludes actual patient data) and actual patient data to such external or non-local resources 50, 1000 at random times. As also indicated in FIG. 10A, in some embodiments a network-based or cloud-based bot (e.g., software-based automaton) can manage or control the communication of data (e.g., actual patient data) from the network-based resources 50 to a given set of provider-side resources 1000.

Moreover, in certain embodiments the patient-side data communication manager 600 can be configured for coordinating, managing, or controlling the communication of dummy data to external or non-local resources 1000 the majority or vast majority of the time, and sending specific types and/or limited amounts of patient-related data, such as patient biomarker data corresponding to or obtained during a set of patent biomarker acquisition or monitoring sessions, or patient biomarker data that falls outside of expected or typical/normal range for the patient, or which deviates by more than a threshold amount away from a population average, or notifications/alerts corresponding to such types of patient biomarker data, to the external or non-local resources 50, 1000 much less frequently than the dummy data is sent to the external or non-local resources 50, 1000. For instance, dummy data can be sent to the external or non-local resources 50, 1000 more than 50%, 60%, 70%, 75%, 80%, 85%, 90%, 95%, or 97.5% of the time relative to the times during which actual patient data (e.g., patient biomarker data, statistical analyses thereof, and/or notifications or alerts corresponding thereto) is sent to such external or non-local resources 50, 1000, depending upon embodiment and/or situational details (e.g., associated with the patient's current medical condition, state, or status).

As indicated in an embodiment shown in FIG. 10B, in the context of a specific set of patient-side resources 100 a biomarker monitoring device 400 in association with a PIIM 200 corresponding thereto can communicate actual patient data, such as patient biomarker data obtained during one or more patient biomarker acquisition or monitoring sessions, to the prescription management agent 500. Based on actual patient data received, the prescription management agent 500 can provide customized or personalized prescription-related feedback, guidance, advice, instructions, coaching, etc. . . . to the patient (e.g., in a manner indicated above, without requiring or needing further data communication with external or non-local resources 50, 1000). The prescription management agent 500 operates cooperatively with the data communication manager 600, which sends dummy data to external or non-local resources 50, 1000 at particular random times, and which sends particular actual patient data and/or summary data corresponding thereto to the external or non-local resources 50, 1000 as necessary/at other times (e.g., only as needed/required). Moreover, the data communication manager 600 can be or typically is configured for sending dummy data much more frequently than sending actual patient data to the external or non-local resources 50, 1000.

As indicated in another possible embodiment in FIG. 10C, a patient biomarker monitoring device 400, a corresponding PIIM 200, and the data communication manager 600 can cooperatively operate such that both dummy data and actual patient data is communicated to the prescription management agent 500. Based on or using the actual patient, the data prescription management agent 500 can perform prescription management services or operations, including patient monitoring and advisory services or operations; and the prescription management agent 500 can communicate the dummy data to external or non-local resources 50, 100 at particular random times, and can communicate at least some of the actual patient data to the eternal or non-local resources 50, 100 at other random times.

In association with or further to the foregoing, individuals having ordinary skill in the relevant art will recognize that the emergence of 4G and 5G technologies have greatly lowered the cost of data transmission, and modern telecommunications therefore facilitates or enables the use of "stuffing messages" which contain encrypted payloads that may or may not represent an actual reading, e.g., actual patient biomarker data. In various embodiments of the present disclosure, actual patient biomarker data communication or transmission external or non-local to a set of patient-side resources 100 (e.g., by way of a patient biomarker monitoring device 400, which can be a D2C2 device 400) occurs in accordance with any point process, for example, a discrete Poisson process. More particularly, actual patient biomarker data or biomarker readings acquired or generated by a given patient biomarker monitoring device 400 are queued and may only be transmitted to network-based and/or provider-side resources 50, 1000 at a next actual transmission event, unless the patient biomarker data corresponds to or is designated as an emergency event, in which case it is immediately transmitted to such external or non-local resources 50, 1000. In multiple embodiments, this is implemented by generating a random variable periodically, and only if the random variable is less than a certain value is the data transmission to external or non-local resources 50, 1000 made. A further test is performed, such that if the random variable lies in a further certain range, dummy data or a dummy reading is created and sent. This conserves power/battery life and transmission costs, while disguising the transmission time, since nothing can be inferred from the actual times of transmission or content of the encrypted message. The stuffing of dummy messages that are sent to external or non-local resources 50, 1000 also serves a secondary purpose of providing a "heartbeat" which assures that a malfunctioning or unserviceable biomarker monitoring device 400 is eventually detected and diagnosed, and measures can be taken to advise the patient to have the device's battery changed/charged, or the biomarker monitoring device 400 otherwise serviced/repaired.

In association with the acquisition or generation or patient biomarker data or a biomarker reading, a "salt" variable (a random string of variable length) can also be generated and appended, together with a fixed "cohort message" and an ID code corresponding to the user; and an entire message can then be encrypted with a given key (e.g., a public key), of which only the counterpart key (e.g., private key of the pair) has been lodged with the patient's care provider. The message is then sent to the network-based resources 50 and/or a specific set of provider-side resources 1000. If dummy data or a dummy reading is being transmitted, then a string corresponding to a "dummy message", which could be a random string or number, is transmitted. The general format of such a message is thus:

$C_{pub}$[cohort, dummy message, salt, patient ID obtained from patient biometric device(s), biomarker monitoring device reading, time of reading]

In some embodiments, the patient's care provider can use an application program or app (e.g., an app that is executable/executed on the set of provider-side resources 1000 corresponding to the provider) that periodically downloads all messages which have been sent regarding a patient cohort for which he or she is responsible. Each message can be decoded with every private key of all patients in the cohort, and only those messages having a clear and correct cohort message are retained, i.e., garbled messages corresponding to the use of an incorrect private key, or a transmission showing the dummy message are all discarded at the care provider's end-point. Thus, the care provider processes only the intended and identified biomarker data or readings from the desired patient, in a manner that disguises who is sending such data or readings and at what times.

In many cases it is time-consuming and expensive for a care provider to examine every message, and it can be desirable for an additional, adjunctive, or auxiliary automaton such as a network-based bot 55 indicated above, to also be checking/analyzing messages received at or by the network-based resources 50, and determining whether or ensuring that the patient is compliant in acquiring their biomarker data or taking their biomarker readings, and that the biomarker data or readings do not indicate that prompt intervention by the patient's care provider is desired or required. Thus, in some embodiments the network-based bot 55 can assist or further assist a prescription management unit 500 in the communication of prescription-related messages to the patient, and/or the communication of alerts to the patient's care provider. While such a process can be conducted at the care provider's premises manually or by way of automation, the network-based bot 55 can be uploaded to the network-based resources 50 and run in a privacy-preserving manner. This has an advantage in that it retains the reliability of network-based (e.g., cloud-based) operations, and does not depend on typically less-reliable on-premises operations that might, for example, be dependent on the connectivity of a care provider's desktop computer or a small server in the care provider's facility or office. The ability to carry out required basic checks regarding patient prescription compliance and an acceptable range of patient biomarker readings can be accomplished using rudimentary concepts of homomorphic encryption, such as Order Preserving Encryption (OPE). As individuals having ordinary skill in the relevant art will readily comprehend, OPE can be simply thought of as a random mapping of value which preserves order. Hence, the bot 55 can check that the patient has taken a given biomarker reading (e.g., a blood pressure reading) within the current week, without knowing the day/date or the time, and check that the value of the biomarker reading is within a certain acceptable or expected range without disclosing the actual value thereof. This enables the network-based bot 55 to send or coordinate the sending of reminder messages to the patient, and for selected alarms or events to be forwarded to the appropriate set of provider-side resources 1000 without the patient's care provider having to scan through, monitor, or eyeball every biomarker data value. It should be noted that OPE used by itself is not highly secure, but when used in combination with other security safeguards it can be a useful added safety factor, in a manner understood by individuals having ordinary skill in the art of cryptography and data security, and would be effective in preserving privacy as well as facilitating care.

Further to the foregoing, to summarize certain aspects of particular data privacy enhancing or preserving operations performed by particular non-limiting representative embodiments in accordance with the present disclosure:

1. The patient activates a given biomarker monitoring device 400, which receives, acquires, or generates patient identification information (e.g., patient-specific biometric data);
2. The patient identification information is authenticated and identified as a hashed and salted user number PATid; and
3. The prescription management agent 500 is activated, and computes a start transmission into a next state. This could involve the delivery of a message or a query privately to the patient, or the transmission of a message, denoted Message, possibly containing biomarker measurement data or readings, to the network-based resources 50. Messages to be communicated to the network-based resources 50 can be queued in a buffer.

At periodic intervals, a random floating point value $v \in [0, 1]$ is generated, and message content and message communication to external or non-local resources 50, 1000 is correlated with this value, such as in accordance with the following:

a. If $v \leq a1$, Packet=NULL
   b. If $a1 < v \leq a2$, Packet=Cpub[dummy cohort name, salt, dummy patient ID, OPE(dummy message), dummy reading time]
   c. If $a2 < v \leq 1$, Packet=Cpub[cohort name, salt, PATid, OPE(Message), time of message generation]
   If Packet !=NULL then transmit Packet If a network-based bot 55 is not available or currently in use that automatically processes/reads messages received at or by the network-based resources 50, and which appropriately handles, processes, or forwards dummy messages and actual messages containing actual patient biomarker data or readings, then message packets (which contain either dummy data values or readings or actual patient data values or readings) can simply be stored on the network-based resources 50. When the time comes for the packets to be retrieved by the care provider, all packets corresponding to a time duration of interest can be downloaded to the care provider's workstation or mobile device. All packets are sequentially decoded using Cpri, the private key corresponding to Cpub. All downloaded packets are discarded except those with the correct cohort name. The inverse of OPE is also applied and the readings are examined by the care provider and normal clinical processes are followed.

In case a network-based bot 55 is used, it also decodes the packet using Cpri, but only knows the encrypted ID of the user and the OPE'd device readings and time of readings. Nevertheless, it can provide reminders if no dummy readings have been received (device out of order), or expected patient biomarker readings are delayed or missing. It can also provide (e.g., automatically provide) other advice or instructions if actual patient biomarker readings are received, based on processing/analysis of patient biomarker data or reading range tests on the OPE values.

Figure 11A:
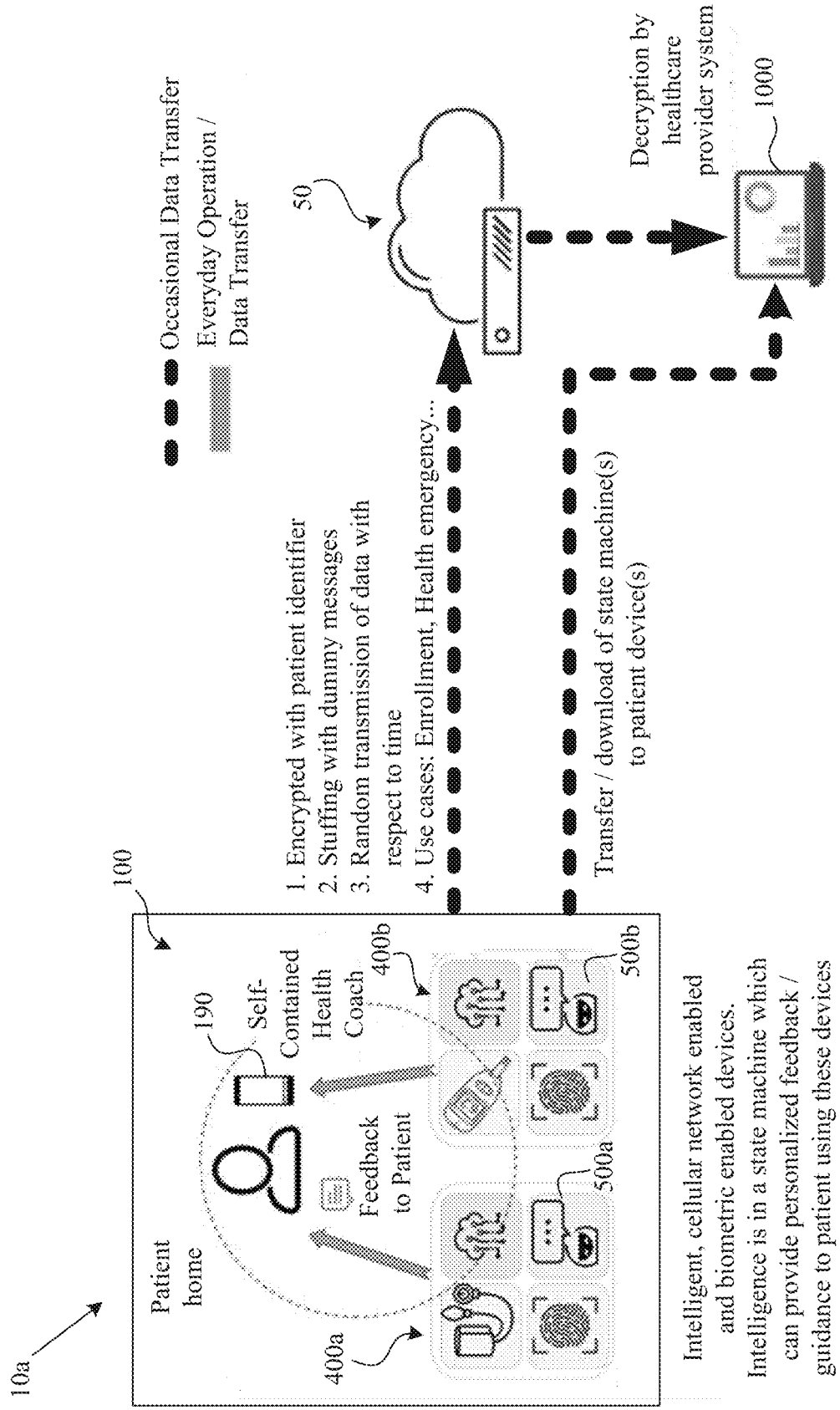
FIGS. 11A-11B show aspects of private medical data communication provided by a system for in-home patient monitoring in accordance with certain embodiments of the present disclosure.
Figure 11B:
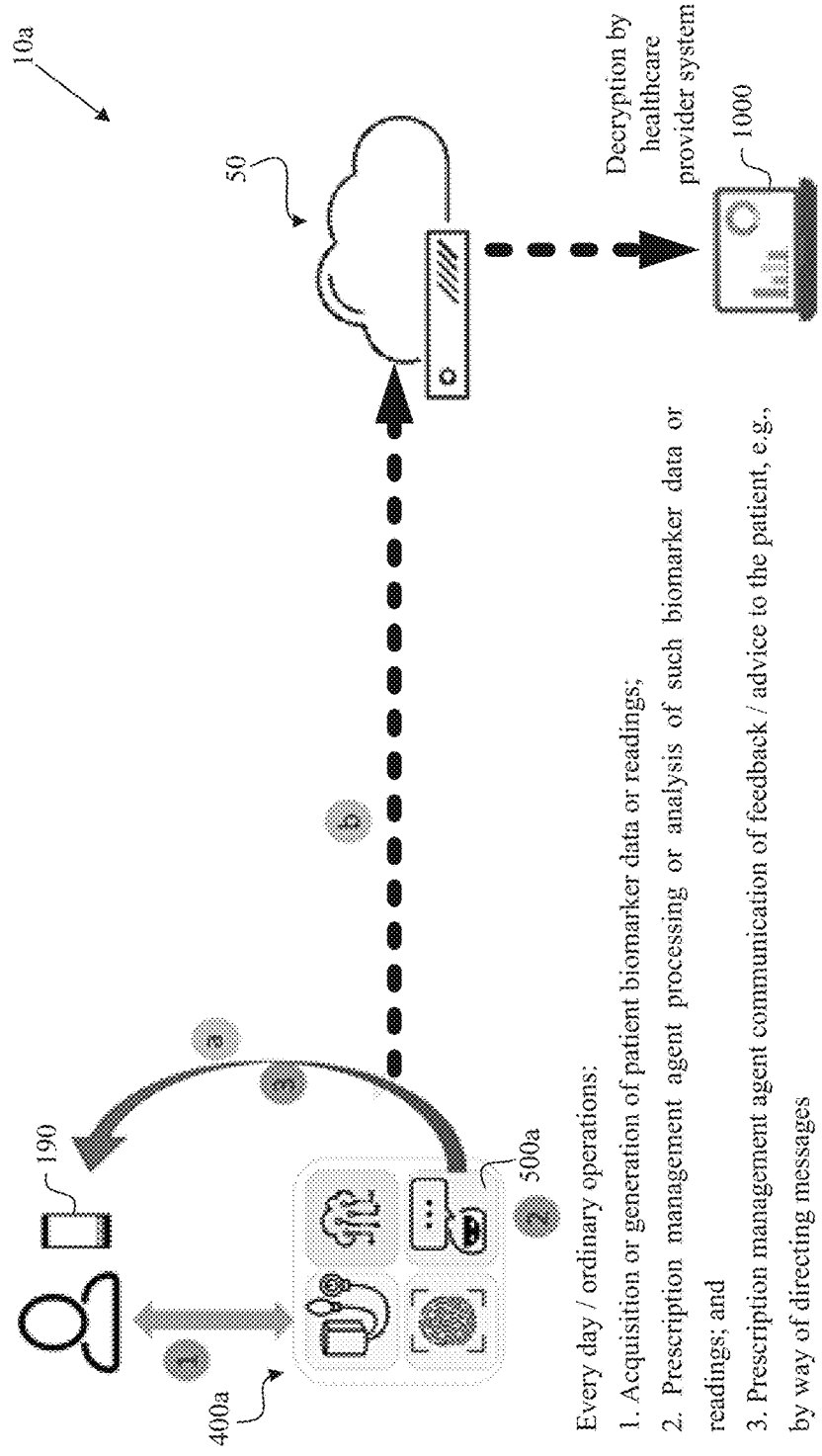

Still further to the foregoing, FIGS. 11A-11B show aspects of a system 10a for in-home patient monitoring in accordance with a non-limiting representative embodiment of the present disclosure. In such a system 10a, a set of patient-side resources includes one or multiple biomarker monitoring devices 400a,b configured for biometric-based patient authentication, data network communication including cellular network communication, a prescription management agent 500, and a patient computing device 190. In several (though not necessarily all) embodiments, a given biomarker monitoring device 400a,b can also have associated therewith or include a PIIM 200 (e.g., in a manner described above). As indicated in FIG. 11A, every day or ordinary operation or data communication occurs in the context of the set of patient-side resources 100, whereas occasional data transfer corresponds to the transfer of each of messages corresponding to actual patient biomarker data and dummy messages to the network-based resources 50; and the transfer of a current prescription from a set of provider-side resources 1000 to the set of patient-side resources 100.

As indicated in FIG. 11B, prescription management services that occur in association with every day or ordinary operation or data communication can involve or include the following:

1. Acquisition or generation of patient biomarker data or readings;
2. Prescription management agent processing or analysis of such biomarker data or readings; and
3. Prescription management agent communication of feedback/advice to the patient, e.g., by way of directing messages to a patient computing device 190.

Additionally, time triggered actions that occur in association with every day or ordinary operation or data communication include the issuance of prescription-related notifications, reminders, or advice (e.g., relating to medication, exercise, or food) to the patient computing device 190.

Figure 12:
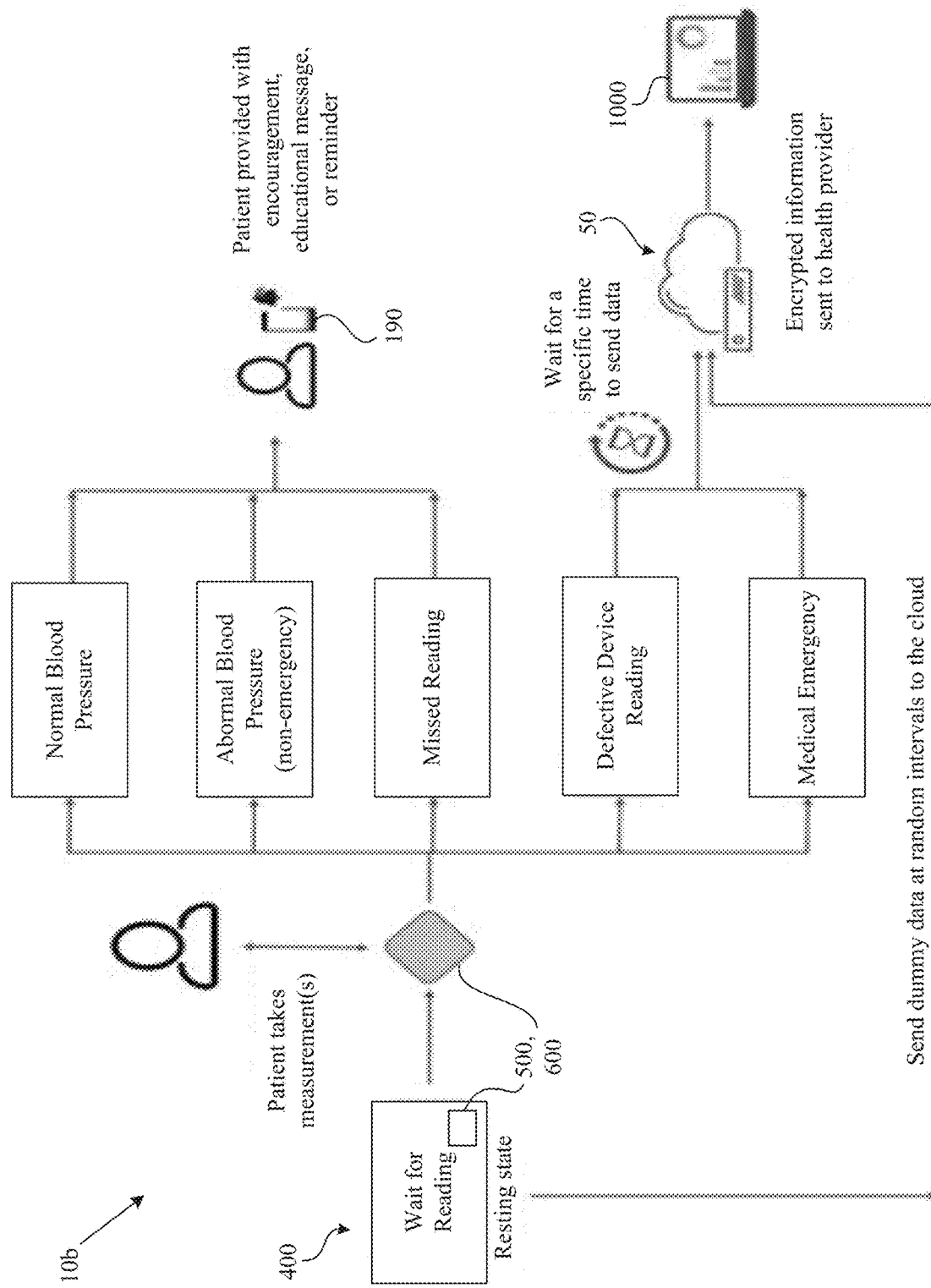
FIG. 12 illustrates aspects of biomarker data processing and data communication performable or performed by an in-home patient monitoring system in accordance with an embodiment of the present disclosure.

Event triggered actions that occur in association with occasional data communication include the transfer of data (e.g., in the form of messages or packets) to network-based resources 50, and the transfer or data (e.g., in the form of one or more messages or packets) to a set of provider-side resources in response to the detection of a possible or likely medical complication or emergency. Yet further to the foregoing, FIG. 12 illustrates non-limiting representative aspects of biomarker data processing and data communication performable or performed by an in-home patient monitoring system or device 10*b* configured for monitoring patient blood pressure (e.g., a blood pressure cuff device) in accordance with an embodiment of the present disclosure. As indicated in FIG. 12, after the patient takes a set of biomarker measurements or readings, which in this case includes at least one blood pressure measurement or reading, if the blood pressure measurement(s) or reading(s) indicate that the patient's blood pressure is normal, or abnormal but not a medical emergency, or if the patient missed or skipped taking a blood pressure measurement or reading at an expected or scheduled date/time, the prescription management agent 500 in association with or using the data communication manager 600 communicates a corresponding type of message to the patient computing device 190 (e.g., an encouragement message if the blood pressure measurement(s) or reading(s) were normal; an educational message if the blood pressure measurement(s) or reading(s) were abnormal but not indicative of a medical emergency; and a reminder if the patient missed or skipped taking a blood pressure measurement or reading).

If a set or series of blood pressure measurement or reading values indicates that the blood pressure cuff device 10*b* is defective, the prescription management agent 500 in coordination with the data communication manager 600 generate a defective device message, which is sent to the network-based resources 50 at a particular time, such as after a specific wait time, such that the network-based resources 50 can forward the defective device message to the appropriate set of provider-side resources 1000.

If a set of blood pressure measurement or reading values indicates that a current or recent medical emergency is possible or likely, the prescription management agent 500 in coordination with the data communication manager 600 generate an emergency alert message, which is immediately sent to the network-based resources 50, such immediately following receipt of the emergency alert message the network-based resources 50 can transfer or forward the emergency alert message to the appropriate set of provider-side resources 1000.

The above description details aspects of multiple systems, subsystems, apparatuses, devices, techniques, processes, and/or procedures in accordance with particular non-limiting representative embodiments of the present disclosure. It will be readily understood by a person having ordinary skill in the relevant art that modifications can be made to one or more aspects or portions of these and related embodiments without departing from the scope of the present disclosure, which is limited only by the following claims.

The invention claimed is:

1. An automated medical treatment plan and medical data processing, monitoring, and communication method comprising:

providing a system configured to perform secure, private, trusted, and safety-enhanced automated medical treatment plan management and medical data processing, monitoring, and communication operations corresponding to a patient, wherein the system is configured to communicate data over a data communication network, and wherein the system comprises: a trusted computing base configured to operate to assure each of data security, data privacy, data trust, and patient safety; and data processing resources organized as:
  a set of provider-side data processing resources corresponding to a medical care provider associated with the patient, the set of provider-side data processing resources coupled to the data communication network, wherein the set of provider-side data processing resources comprises a provider-side computing system configured to execute a patient management application by which a patient treatment plan comprising a current prescription corresponding to the patient, which includes a current prescription protocol corresponding to the patient, is defined by the care provider, and wherein the current prescription protocol specifies at least one biomarker that is medically relevant to the patient's health that the patient is to monitor in accordance with a biomarker monitoring schedule; and
  a set of patient-side data processing resources, the set of patient-side data processing resources coupled to the data communication network and configured to selectively communicate data over the data communication network, wherein the set of patient-side data processing resources comprises:
    a patient identification/biometrics module configured to generate patient identification/biometrics data corresponding to the patient in response to patient input;
    a biomarker monitoring device associated with the patient, the biomarker monitoring device configured to acquire or monitor a set of patient biomarkers, including the at least one biomarker specified in the current prescription protocol, and store corresponding patient biomarker data in a biomarker data store;
    a patient computing device comprising a processing unit and a memory in which resides an automated prescription management agent that is executable by the processing unit and which when executed automatically performs prescription management operations corresponding to the current prescription protocol; and
    a Personal Identity and Information Manager (PIIM) associated with or corresponding to the patient, wherein the PIIM comprises data processing resources configured as the trusted computing base, including:
      a control module comprising a processing unit configured to perform PIIM based and/or PIIM mediated operations, including storing and managing validated identities and direct trust assertions, by way execution of stored program instructions corresponding to a PIIM control program;
      a data communication manager configured to coordinate or control selective communication of data from the set of patient-side computing resources to one or more destinations external to the set of patient-side data processing resources by way of the data communication network;

a registration module configured to manage the registration one or more unique identities corresponding to the patient, and a unique identity corresponding to the biomarker monitoring device;

a validation module configured to validate data corresponding to a patient identity, data corresponding to a biomarker monitoring device identity, and data corresponding to a care provider identity;

a key derivation and/or generation function module configured to derive and/or generate data encryption keys and data decryption keys;

a cryptographic module configured to encrypt and decrypt data;

a checkbot module providing a set of automated checkbots configured to execute in scope or context of the PIIM trusted computing base and the PIIM based and/or PIIM mediated operations provided thereby, wherein by way of checkbot execution the set of checkbots performs independent and uncoupled assertion checking processes and prescription management agent checking processes to assure data security, data privacy, data integrity, and patient safety, and wherein the set of checkbots includes a prescription checkbot;

a secure prescription protocol store configured to store at least the current prescription protocol; and a secure store unit providing each of: a trust store in which one or more digital signatures and/or authentication codes reside; an identity store configured to store at least one identity corresponding to the patient; a number-used-once (NONCE) store and/or generator configured to store and/or generate cryptographic NONCEs; and an assertion store in which a customizable set of assertions updatable by a trusted authority reside, such that the prescription checkbot can validate the current prescription protocol and/or biomarker data associated therewith to identify/recognize prescription-related error, contraindication, and/or alert conditions relevant to patient safety;

and by way of the system including the trusted computing base thereof and PIIM control module performance of the PIIM based and/or PIIM mediated operations, performing a set of secure, private, trusted, and safety-enhanced automated medical treatment plan management and medical data processing, monitoring, and communication processes corresponding to the patient, the set of patient-side data processing resources including the biomarker monitoring device and the PIIM, the care provider associated with the patient, and the set of provider-side data processing resources, in which the trusted computing base operates to assure each of data security, data privacy, data trust, and patient safety, and which comprises:

attempting to sequentially establish by way of the PIIM in accordance with PIIM performance of the PIIM based and/or PIIM mediated operations, including checkbot execution, a plurality of computationally verified direct trust relationships including:

a computationally verified first direct trust relationship between the PIIM and the patiept by way of: data communication between the PIIM and the patient identification/biometrics module following patient input directed to the patient identification/biometrics module; PIIM performance of patient identity validation operations by which the PIIM attempts to validate patient identification data corresponding to the patient based on data communicated between the PIIM and the patient identification/biometrics module with respect to already-existing data within the identity store; and only if PIIM validation of the patient identification data with respect to already-existing data within the identity store is successful, PIIM establishment of a currently active patient identity;

a computationally verified second direct trust relationship between the PIIM and the biomarker monitoring device following PIIM establishment of the currently active patient identity by way of: data communication between the PIIM and the biomarker monitoring device under the currently active patient identity; PIIM performance of biomarker monitoring device integrity validation operations by which the PIIM attempts to validate biomarker monitoring device integrity data based on data communicated between the PIIM and the biomarker monitoring device, wherein validated biomarker integrity data indicates or corresponds to one or more of an intended or expected identity, capability, operational status, and configuration of the biomarker monitoring device; and only if PIIM validation of the biomarker monitoring device integrity data is successful, each of: generating and storing a unique device identity corresponding to the biomarker monitoring device; and PIIM generation of a biomarker data encryption key by which patient biomarker data acquired by the biomarker monitoring device during a biomarker monitoring session corresponding to the currently active patient identity is encrypted; and a computationally verified third direct trust relationship between the PIIM and the care provider after successful PIIM of biomarker monitoring device integrity by way of: data communication between the care provider computing system and the PIIM; performance of PIIM mien based or PIIM mediated care provider identity validation operations in which the PIIM attempts to validate care provider identity data based on data communication between the PIIM and the care provider computing system; and if PIIM validation of the care provider identity data is successful, each of: PIIM generation of a biomarker data decryption key corresponding to the currently active patient identity and the biomarker monitoring device, by which decryption of encrypted biomarker data corresponding to the currently active patient identity and the biomarker monitoring device occurs; PIIM based or PIIM mediated provision of the biomarker data decryption key to the care provider computing system or a set of network-based data processing resources couplable or coupled to the set of provider-side computing resources by way of the data communication network; and PIIM based validation of the current prescription relative to the currently active patient identity by way of the prescription checkbot,
wherein as part of successfully establishing the first direct trust relationship, the second direct trust relationship, and the third direct trust relationship the PIIM generates and stores unique first direct trust relationship data corresponding to the first direct trust relationship, unique second direct trust relationship data corresponding to the second direct trust relationship, and unique third direct trust relationship data corresponding to the third direct trust relationship; and
after establishing each of the first direct trust relationship, the second direct trust relationship, and the third direct trust relationship:
establishing the biomarker monitoring session corresponding to the currently active patient identity, and acquiring, encrypting by way of the biomarker data encryption key, and storing patient biomarker data acquired during the biomarker monitoring session corresponding to the currently active patient identity;
performing a set of self-contained prescription management operations associated with the biomarker monitoring session corresponding to the currently active patient identity by way of execution of the prescription management agent in association with execution of the prescription checkbot, wherein data communication corresponding to the set of self-contained prescription management operations solely involves the set of patient-side data processing resources rather than involving the data communication network and the provider-side data processing resources, and wherein the set of self-contained prescription management operations include automatically:
communicating biomarker data corresponding to the currently active patient identity to the prescription management agent and/or the PIIM;
performing biomarker data analysis upon biomarker data corresponding to the currently active patient identity in relation to the current prescription protocol;
performing prescription compliance analysis indicating patient compliance with the current prescription protocol;
determining by way of the prescription checkbot whether patient safety is maintained by automatically identifying or recognizing error, contraindication, and/or alert conditions relevant to the safety of the patient in relation to the current prescription protocol; and
prescription checkbot limiting, restricting, or preventing at least one of prescription management agent:
(a) communication of data to the patient computing device corresponding to patient instructions, coaching, guidance, reminders, or recommendations in the event that patient safety is not maintained; and
(b) adaptive adjustment of the current prescription protocol in the event that patient safety is not maintained.

2. The method of claim 1, wherein establishing the first direct trust relationship comprises:

generating the patient identification data by way of the patient identification/biometrics module in response to patient interaction therewith;
provision of the patient identification data to the PIIM;
PIIM performance of the patient identity validation operations using the patient identification data, during which the PIIM attempts to validate the patient identification data;
PIIM generation and storage of a new unique patient identity corresponding to the patient in response to unsuccessful validation of the patient identification data; and
PIIM retrieval of a previously generated and stored unique patient identity as the currently active patient identity in response to successful validation of the patient identification data.

3. The method of claim 2, wherein establishing the second direct trust relationship comprises:
establishing communication between the PIIM and the biomarker monitoring device under the currently active patient identity;
PIIM performance of the biomarker monitoring device integrity validation operations in which the PIIM attempts to validate a hardware identity and/or a software identity of the biomarker monitoring device; and
following successful PIIM validation of the hardware identity and/or the software identify of the biomarker monitoring device:
PIIM generation and storage, or PIIM retrieval, of a unique code corresponding to the biomarker monitoring device; and
PIIM generation of the biomarker data encryption key as an ephemeral biomarker data encryption key.

4. The method of claim 3, wherein as part of the biomarker monitoring device integrity validation operations, the PIIM attempts to validate secure boot protocol data generated by the biomarker monitoring device.

5. The method of claim 3, wherein establishing the third direct trust relationship comprises:
PIIM generation of a biomarker data decryption code corresponding to the active patient identity and the biomarker monitoring device;
PIIM association of the biomarker data decryption code with a unique one-time use code;
communication of the unique one-time use code to the set of provider-side data processing resources;
attempted validation of the one-time use code by way of communication between the set of provider-side data processing resources and the PIIM; and
in response to successful validation of the one-time use code, PIIM generation of the biomarker data decryption key.

6. The method of claim 5, wherein communication of the one-time use code to the set of provider-side data processing resources comprises:
communicating the one-time use code from the PIIM to the patient computing device; and
subsequently communicating the one-time use code from the patient computing device to the set of provider-side data processing resources.

7. The method of claim 6, wherein the one-time use code is encoded in a matrix barcode or a Quick Response (QR) code.

8. The method of claim 5, wherein attempted validation of the one-time use code comprises:
communication of an assertion signed by the care provider's digital signature to the PIIM; and PIIM determination of whether the assertion was digitally signed by a trusted authority or an approved delegate of the trusted authority.

9. The method of claim 1, wherein: (a) the biomarker monitoring device carries the PIIM, and the PIIM comprises integrated circuitry provided as part of the biomarker monitoring device; (b) the PIIM comprises integrated circuitry carried by a smart card or a patient identification card belonging to the patient; (c) the PIIM corresponds to a customized Subscriber Identity Module (SIM) card, and comprises integrated circuitry associated with the customized SIM card, wherein customized SIM card is carried by a smartphone corresponding to the patient and which forms a portion of the patient-side data processing resources; or (d) the PIIM comprises a set of program instructions stored in a memory of and executable by the processing unit of athe patient computing device, wherein the patient computing device includes a tamper-evident or tamper-proof memory or data store configured to be used exclusively by the PIIM.

10. The method of claim 1, further comprising communicating the prescription management agent from the set of provider-side data processing resources to the patient computing device by way of the data communication network.

11. The method of claim 1, wherein the prescription management agent comprises a state machine executable by the processing unit of the patient computing device.

12. The method of claim 11, wherein the method further comprises prescription checkbot analysis of prescription management agent state transitions corresponding to execution of the current prescription protocol, and, prescription checkbot determination of whether aspects of the current prescription protocol fall outside of or too closely approach recognized or established guidelines or contraindications for patient safety.

13. The method of claim 12, wherein the prescription checkbot limiting, restricting, or preventing (a) prescription management agent transfer of data to the patient computing device corresponding to the presentation of particular instructions, recommendations, or information to the patient, and (b) prescription management agent's adaptive adjustment of particular prescription protocol parameters are based on the prescription checkbot's analysis of one or more current prescription protocol state transitions corresponding to execution of the current prescription protocol.

14. The method of claim 1, wherein the patient computing device comprises a smartphone having a memory in which the prescription management agent resides, and a smartphone processing unit configured for executing the prescription management agent.

15. The method of claim 1, further comprising:
performing an additional set of prescription management operations involving data communication between the set of patient-side data processing resources and the data communication network, wherein the additional set of prescription management operations comprises selectively communicating at random times each of dummy data and actual patient data comprising at least one of patient biomarker data, summary data corresponding to patient biomarker data, and an emergency alert to a destination external to the set of patient-side data processing resources and which comprises one of the set of provider-side data processing resources and a set of network based data processing resources couplable or coupled to the set of provider-side data processing resources, wherein the communication of the dummy data to the external destination occurs at least 50% more frequently than the communication of actual patient data to the external destination.

16. A system configured to perform secure, private, trusted, and safety-enhanced automated medical treatment plan management and medical data processing, monitoring, and communication operations by way of a trusted computing base, wherein system data communication occurs by way of a data communication network, wherein system data communication involves data communication with a set of provider-side data processing resources corresponding to a medical care provider associated with the patient, wherein the set of provider-side data processing resources comprises a provider-side computing system configured to execute a patient management application by which a patient treatment plan comprising a current prescription corresponding to the patient, which includes a current prescription protocol corresponding to the patient, is defined by the care provider, wherein the current prescription protocol specifies at least one biomarker that is medically relevant to the patient's health that the patient is to monitor in accordance with a biomarker monitoring schedule, and wherein the system comprises:
a set of patient-side data processing resources associated with or corresponding to the patient, the set of patient-side data processing resources couplable to the data communication network and configured to selectively communicate data over the data communication network, wherein the set of patient-side data processing resources comprises:
a patient identification/biometrics module configured to generate patient identification/biometrics data corresponding to the patient in response to patient input;
a biomarker monitoring device associated with the patient, the biomarker monitoring device configured to acquire or monitor a set of patient biomarkers, including the at least one biomarker specified in the current prescription protocol, and store corresponding patient biomarker data in a biomarker data store;
a patient computing device comprising a processing unit and a memory in which resides an automated prescription management agent that is executable by the processing unit and which when executed automatically performs prescription management operations corresponding to the current prescription protocol; and
a Personal Identity and Information Manager (PHM) associated with or corresponding to the patient, wherein the PIIM comprises data processing resources configured as a trusted computing base, and wherein the PIIM data processing resources comprise:
a control module comprising a processing unit configured to perform PIIM based and/or PIIM mediated operations, including storing and managing validated identities and direct trust assertions, by way execution of stored program instructions corresponding to a PIIM control program;
a data communication manager configured to coordinate or control selective communication of data from the set of patient-side computing resources to one or more destinations external to the set of patient-side data processing resources by way of the data communication network;
a registration module configured to manage the registration one or more unique identities corresponding to the patient, and a unique identity corresponding to the biomarker monitoring device;

a validation module configured to validate data corresponding to a patient identity, data corresponding to a biomarker monitoring device identity, and data corresponding to a care provider identity;

a key derivation and/or generation function module configured to derive and/or generate data encryption keys and data decryption keys;

a cryptographic module configured to encrypt and decrypt data;

a checkbot module providing a set of automated checkbots configured to execute in scope or context of the PIIM trusted computing base and the PIIM based and/or PIIM mediated operations provided thereby, wherein by way of checkbot execution the set of checkbots performs independent and uncoupled assertion checking processes and prescription management agent checking processes to assure data security, data privacy, data integrity, and patient safety, and wherein the set of checkbots includes a prescription checkbot;

a secure prescription protocol store configured to store at least the current prescription protocol; and a secure store unit providing each of: a trust store in which one or more digital signatures and/or authentication codes reside; an identity store configured to store at least one identity corresponding to the patient; a number-used-once (NONCE) store and/or generator configured to store and/or generate cryptographic NONCEs; and an assertion store in which a customizable set of assertions updatable by a trusted authority reside, such that the prescription checkbot can validate the current prescription protocol and/or biomarker data associated therewith to identify/recognize prescription-related error, contraindication, and/or alert conditions relevant to patient safety, wherein:
(a) the PIIM comprises integrated circuitry provided as part of the biomarker monitoring device;
(b) the PIIM comprises integrated circuitry carried by a smart card or a patient identification card belonging to the patient;
(c) the PIIM comprises integrated circuitry associated with a customized Subscriber Identity Module (SIM) card, wherein the customized SIM card is carried by a smartphone corresponding to the patient and forms a portion of the patient-side data processing resources; or
(d) the PIIM comprises a set of program instructions stored in a memory of and executable by the processing unit of the patient computing device, wherein the patient computing device includes a tamper-evident or tamper-proof memory or data store configured to be used exclusively by the PIIM.

17. The system of claim 16, wherein the biomarker monitoring device is an in-home biomarker monitoring device disposed in a home of the patient.

18. The system of claim 16, wherein the PIIM control program when executed, in association with checkbot execution, is configured to attempt to sequentially establish a plurality of computationally verified direct trust relationships including:

a computationally verified first direct trust relationship between the PIIM and the patient by way of: data communication between the PIIM and the patient identification/biometrics module following patient input directed to the patient identification/biometrics module; PIIM performance of patient identity validation operations by which the PIIM attempts to validate patient identification data corresponding to the patient based on data communicated between the PIIM and the patient identification/biometrics module with respect to already-existing data within the identity store; and only if PIIM validation of the patient identification data with respect to already-existing data within the identity store is successful, PIIM establishment of a currently active patient identity;

a computationally verified second direct trust relationship between the PIIM and the biomarker monitoring device following PIIM establishment of the currently active patient identity by way of: data communication between the PIIM and the biomarker monitoring device under the currently active patient identity; PIIM performance of biomarker monitoring device integrity validation operations by which the PIIM attempts to validate biomarker monitoring device integrity data based on data communicated between the PIIM and the biomarker monitoring device, wherein validated biomarker integrity data indicates or corresponds to one or more of an intended or expected identity, capability, operational status, and configuration of the biomarker monitoring device; and only if PIIM validation of the biomarker monitoring device integrity data is successful, each of: generating and storing a unique device identity corresponding to the biomarker monitoring device; and PIIM generation of a biomarker data encryption key by which patient biomarker data acquired by the biomarker monitoring device during a biomarker monitoring session corresponding to the currently active patient identity is encrypted; and a computationally verified third direct trust relationship between the PIIM and the care provider after successful PIIM validation of biomarker monitoring device integrity by way of: data communication between the care provider computing system and the PIIM;

performance of PIIM based or PIIM mediated care provider identity validation operations in which the PIIM attempts to validate care provider identity data based on data communication between the PIIM and the care provider computing system; if PIIM validation of the care provider identity data is successful, each of: PIIM generation of a biomarker data decryption key corresponding to the currently active patient identity and the biomarker monitoring device, by which decryption of encrypted biomarker data corresponding to the currently active patient identity and the biomarker monitoring device occurs; PIIM based or PIIM mediated provision of the biomarker data decryption key to the care provider computing system or a set of network-based data processing resources couplable or coupled to the set of provider-side computing resources by way of the data communication network; and PIIM based validation of the current prescription relative to the currently active patient identity by way of the prescription checkbot, wherein as part of successfully establishing the first direct trust relationship, the second direct trust relationship, and the third direct trust relationship the PIIM generates and stores unique first direct trust relationship data corresponding to the first direct trust relationship, unique second direct trust relationship data corresponding to the second direct trust relationship, and unique third direct trust relationship data corresponding to the third direct trust relationship.

19. The system of claim 18, wherein the prescription management agent and prescription checkbot when executed control a set of self-contained prescription management operations associated with a biomarker monitoring session corresponding to the currently active patient identity, wherein data communication corresponding to the set of self-contained prescription management operations solely involves the set of patient-side data processing resources rather than involving the data communication network and the provider-side data processing resources, and wherein the set of self-contained prescription management operations comprises automatically:

performing biomarker data analysis upon biomarker data corresponding to the currently active patient identity in relation to the current prescription protocol;

performing prescription compliance analysis indicating patient compliance with the current prescription protocol; determining by way of the prescription checkbot whether patient safety is maintained by automatically identifying or recognizing error, contraindication, and/or alert conditions relevant to the safety of the patient in relation to the current prescription protocol; and prescription checkbot limiting, restricting, or preventing at least one of prescription management agent:

(a) communication of data to the patient computing device corresponding to patient instructions, coaching, guidance, reminders, or recommendations in the event that patient safety is not maintained; and (b) adaptive adjustment of the current prescription protocol in the event that patient safety is not maintained.

20. The system of claim 16, wherein the data communication manager is configured to control or manage selective communication of data from the set of patient-side data processing resources to a destination external to the set of patient-side data processing resources by selectively communicating each of dummy data and actual patient data comprising at least one of patient biomarker data, summary data corresponding to patient biomarker data, and an emergency alert to the destination external to the set of patient-side data processing resources by way of a computer network, wherein the communication of the dummy data to the destination external to the set of patient-side data processing resources occurs at least 50% more frequently than the communication of actual patient data to the destination external to the set of patient-side data processing resources.

* * * * *